(12) United States Patent
Feitelson et al.

(10) Patent No.: US 6,656,908 B2
(45) Date of Patent: Dec. 2, 2003

(54) PESTICIDAL TOXINS AND NUCLEOTIDE SEQUENCES WHICH ENCODE THESE TOXINS

(75) Inventors: Jerald S. Feitelson, San Diego, CA (US); H. Ernest Schnepf, San Diego, CA (US); Kenneth E. Narva, San Diego, CA (US); Brian A. Stockhoff, San Diego, CA (US); James Schmeits, San Diego, CA (US); David Loewer, San Diego, CA (US); Charles Joseph Dullum, San Diego, CA (US); Judy Muller-Cohn, Del Mar, CA (US); Lisa Stamp, Del Mar, CA (US); George Morrill, El Cajon, CA (US); Stacey Finstad-Lee, San Diego, CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 09/850,351

(22) Filed: May 7, 2001

(65) Prior Publication Data

US 2002/0100080 A1 Jul. 25, 2002

Related U.S. Application Data

(63) Continuation of application No. 09/073,898, filed on May 6, 1998, now Pat. No. 6,242,669, which is a continuation-in-part of application No. 08/960,780, filed on Oct. 30, 1997, now Pat. No. 6,204,435.
(60) Provisional application No. 60/029,848, filed on Oct. 30, 1996.

(51) Int. Cl.[7] ........................ C07K 14/325; A01N 37/18
(52) U.S. Cl. .............................. 514/12; 514/2; 530/350
(58) Field of Search ............................. 530/350; 514/2, 514/12

(56) References Cited

U.S. PATENT DOCUMENTS

| | | | |
|---|---|---|---|
| 4,448,885 A | 5/1984 | Schnepf et al. | 435/252.33 |
| 4,467,036 A | 8/1984 | Schnepf et al. | 435/320.1 |
| 4,797,276 A | 1/1989 | Herrnstadt et al. | 424/84 |
| 4,853,331 A | 8/1989 | Herrnstadt et al. | 435/252.3 |
| 4,918,006 A | 4/1990 | Ellar et al. | 435/69.1 |
| 4,948,734 A | 8/1990 | Edwards et al. | 514/2 |
| 4,990,332 A | 2/1991 | Payne et al. | 424/93.461 |
| 5,039,523 A | 8/1991 | Payne et al. | 424/93.461 |
| 5,093,120 A | 3/1992 | Edwards et al. | 514/2 |
| 5,126,133 A | 6/1992 | Payne et al. | 424/93.461 |
| 5,151,363 A | 9/1992 | Payne | 435/252.5 |
| 5,164,180 A | 11/1992 | Payne et al. | 424/93.461 |
| 5,169,629 A | 12/1992 | Payne et al. | 424/93.461 |
| 5,204,237 A | 4/1993 | Gaertner et al. | 435/6 |
| 5,236,843 A | 8/1993 | Narva et al. | 435/252.3 |
| 5,262,399 A | 11/1993 | Hickle et al. | 424/93.2 |
| 5,270,448 A | 12/1993 | Payne | 514/2 |
| 5,281,530 A | 1/1994 | Sick et al. | 435/252.3 |
| 5,322,932 A | 6/1994 | Narva et al. | 530/350 |
| 5,350,577 A | 9/1994 | Payne | 424/93.461 |
| 5,426,049 A | 6/1995 | Sick et al. | 435/252.3 |
| 5,439,881 A | 8/1995 | Narva et al. | 514/2 |
| 5,667,993 A | 9/1997 | Feitelson et al. | 435/91.2 |
| 5,670,365 A | 9/1997 | Feitelson | 435/252.3 |
| 5,770,696 A | 6/1998 | Warren et al. | 530/350 |
| 5,840,868 A | 11/1998 | Warren et al. | 536/23.1 |
| 5,849,870 A | 12/1998 | Warren et al. | 530/350 |
| 5,866,326 A | 2/1999 | Warren et al. | 435/6 |
| 5,872,212 A | 2/1999 | Warren et al. | 530/350 |
| 5,877,012 A | 3/1999 | Estruch et al. | 435/252.3 |
| 5,888,801 A | 3/1999 | Warren et al. | 435/252.3 |
| 5,889,174 A | 3/1999 | Warren et al. | 536/23.71 |

FOREIGN PATENT DOCUMENTS

| | | |
|---|---|---|
| EP | 0 359 472 | 3/1990 |
| WO | WO 94/04684 | 3/1994 |
| WO | WO 94/05771 | 3/1994 |
| WO | WO 94/21795 | 9/1994 |
| WO | WO 94/24264 | 10/1994 |
| WO | WO 96/05314 | 2/1996 |
| WO | WO 96/10083 | 4/1996 |
| WO | WO 98/18932 | 5/1998 |

OTHER PUBLICATIONS

Asano, Shoji et al., "A Unique Activity in *Bacillus thuringiensis* Growth Medium," *Appl. Entomol. Zool.*, 1994, pp. 39–45, vol. 29(1).

Beegle, C.C., "Use of Entomogenous Bacteria in Agroecosystems," *Developments in Industrial Microbiology*, 1978, pp. 97–104, vol. 20.

Carozzi, N.B. et al., "Prediction of Insecticidal Activity of *Bacillus thuringiensis* Strains by Polymerase Chain Reaction Product Profiles," *Applied and Environmental Microbiology*, 1991, pp. 3057–3061, vol. 57(11).

Couch, T.L., "Mosquito Pathogenicity of *Bacillus thuringiensis* var. *israelensis*," *Developments in Industrial Microbiology*, 1980, pp. 61–76, vol. 22.

Estruch, J.J. et al., "Vip3A, A Novel *Bacillus thuringiensis* Vegetative Insecticidal Protein with a Wide Spectrum of Activities Against Lepidopteran Insects," *Proc. Natl. Acad. Sci. USA*, pp. 5389–5394, vol. 93.

Feitelson, J.S. et al., "*Bacillus thuringiensis*: Insects and Beyond," *Bio/Technology*, 1992, pp. 271–275, vol. 10.

Gaertner, F.H. and Leo Kim, "Current Applied Recombinant DNA Projects," *TIBTECH*, 1988, pp. 54–57, vol. 6(4).

(List continued on next page.)

*Primary Examiner*—Gabriele Bugaisky
(74) *Attorney, Agent, or Firm*—Saliwanchik, Lloyd & Saliwanchik

(57) ABSTRACT

Disclosed and claimed are novel *Bacillus thuringiensis* isolates, pesticidal toxins, genes, and nucleotide probes and primers for the identification of genes encoding toxins active against pests. The primers are useful in PCR techniques to produce gene fragments which are characteristic of genes encoding these toxins. The subject invention provides entirely new families of toxins from Bacillus isolates.

2 Claims, No Drawings

OTHER PUBLICATIONS

Gaertner, F.H., "Cellular Delivery Systems for Insecticidal Proteins: Living and Non–Living Microorganisms," *Controlled Delivery of Crop Protection Agents*, R.M. Wilkins, ed., 1989, pp. 245–255, Taylor and Francis, New York and London.

Gleave, A.P. et al., "Identification of an Insecticidal Crystal Protein from *Bacillus thuringiensis* DSIR517 with Significant Sequence Differences from Previously Described Toxins," *Journal of General Microbiology*, 1992, pp. 55–62, vol. 138.

Hofte, H. and H.R. Whiteley, "Insecticidal Crystal Proteins of *Bacillus thuringiensis*," *Microbiological Reviews*, 1989, pp. 242–255, vol. 53(2).

Krieg, V.A. et al., "*Bacillus thuringiensis* var. *tenebrionis*, a new pathotype effective against larvae of Coleoptera," *Z. Ang. Ent.*, 1983, pp. 500–508, vol. 96, Abstract.

Lambert, B. et al., "A *Bacillus thuringiensis* Insecticidal Crystal Protein with a High Activity against Members of the Family Noctuidae," *Applied and Environmental Microbiology*, 1996, pp. 80–86, vol. 62(1).

Li, Jade, "Bacterial Toxins," *Current Opinion in Structural Biology*, 1992, pp. 545–556, vol. 2.

Schnepf, H.E. and H.R. Whiteley, "Cloning and Expression of the *Bacillus thuringiensis* Crystal Protein Gene in *Escheria coli*," *Proc. Natl. Acad. Sci. USA*, 1981, pp. 2893–2897, vol. 78(5).

Shevelev, A.B. et al., "Primary Structure of cryX**, the Novel δ–endotoxin–related Gene from *Bacillus thuringiensis spp. galleriae*,"*FEBS*, 1993, pp. 79–82, vol. 336(1).

Smulevitch, S.V. et al., "Nucleotide Sequence of a Novel δ–Endotoxin Gene *crylg* of *Bacillus thuringiensis* ssp. *galleriae*," *FEBS*, 1991, pp. 25–28, vol. 293(1–2).

PESTICIDAL TOXINS AND NUCLEOTIDE SEQUENCES WHICH ENCODE THESE TOXINS

CROSS-REFERENCE TO RELATED APPLICATIONS

This application is a continuation of co-pending application Ser. No. 09/073,898, filed May 6, 1998 now U.S. Pat. No. 6,242,669; which is a continuation-in-part of Ser. No. 08/960,780, filed Oct. 30, 1997, now U.S. Pat. No. 6,204,435; which claims priority from provisional application Ser. No. 60/029,848, filed Oct. 30, 1996.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4–S7). Thus, isolated B.t. endotoxin genes are becoming commercially valuable.

Until the last fifteen years, commercial use of B.t. pesticides has been largely restricted to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *morrisoni* (a.k.a. *tenebrionis*, a.k.a. B.t. M-7, a.k.a. B.t. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of *Bacillus thuringiensis* var. israelensis," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. *tenebrionis*, which is reportedly active against two beetles in the order Coleoptera. These are the Colorado potato beetle, *Leptinotarsa decemlineata*, and *Agelastica alni*.

More recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1): 80–86) describe the characterization of a Cry9 toxin active against lepidopterans. Published PCT applications WO 94/05771 and WO 94/24264 also describe B.t. isolates active against lepidopteran pests. Gleave et al. ([1991] *JGM* 138:55–62), Shevelev et al. ([1993] *FEBS Lett.* 336:79–82; and Smulevitch et al. ([1991] *FEBS Lett.* 293:25–26) also describe B.t. toxins. Many other classes of B.t. genes have now been identified.

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897.). U.S. Pat. Nos. 4,448,885 and 4,467,036 both disclose the expression of B.t. crystal protein in *E. coli*. U.S. Pat. Nos. 4,990,332; 5,039,523; 5,126,133; 5,164,180; and 5,169,629 are among those which disclose B.t. toxins having activity against lepidopterans. PCT application WO96/05314 discloses PS86W1, PS86V1, and other B.t. isolates active against lepidopteran pests. The PCT patent applications published as WO94/24264 and WO94/05771 describe B.t. isolates and toxins active against lepidopteran pests. B.t. proteins with activity against members of the family Noctuidae are described by Lambert et al, supra. U.S. Pat. Nos. 4,797,276 and 4,853,331 disclose *B. thuringiensis* strain *tenebrionis* which can be used to control coleopteran pests in various environments. U.S. Pat. No. 4,918,006 discloses B.t. toxins having activity against dipterans. U.S. Pat. Nos. 5,151,363 and 4,948,734 disclose certain isolates of B.t. which have activity against nematodes. Other U.S. patents which disclose activity against nematodes include U.S. Pat. Nos. 5,093,120; 5,236,843; 5,262,399; 5,270,448; 5,281,530; 5,322,932; 5,350,577; 5,426,049; 5,439,881, 5,667,993; and 5,670,365. As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art.

Isolating responsible toxin genes has been a slow empirical process. Carozzi et al. (Carozzi, N. B., V. C. Kramer, G. W. Warren, S. Evola, G. Koziel (1991) *Appl. Env. Microbiol.* 57(11):3057–3061) describe methods for identifying toxin genes. U.S. Pat. No. 5,204,237 describes specific and universal probes for the isolation of B.t. toxin genes. That patent, however, does not describe the probes and primers of the subject invention.

WO 94/21795, WO 96/10083, and Estruch, J. J. et al. (1996) *PNAS* 93:5389–5394 describe toxins obtained from Bacillus microbes. These toxins are reported to be produced during vegetative cell growth and were thus termed vegetative insecticidal proteins (VIP). These toxins were reported to be distinct from crystal-forming δ-endotoxins. Activity of these toxins against lepidopteran and coleopteran pests was reported. These applications make specific reference to toxins designated Vip1A(a), Vip1A(b), Vip2A(a), Vip2A(b), Vip3A(a), and Vip3A(b). The toxins and genes of the current invention are distinct from those disclosed in the '795 and '083 applications and the Estruch article.

BRIEF SUMMARY OF THE INVENTION

The subject invention concerns materials and methods useful in the control of non-mammalian pests and, particularly, plant pests. In one embodiment, the subject invention provides novel B.t. isolates having advantageous activity against non-mammalian pests. In a further embodiment, the subject invention provides new toxins useful for the control of non-mammalian pests. In a preferred embodiment, these pests are lepidopterans and/or coleopterans. The toxins of the subject invention include δ-endotoxins as well as soluble toxins which can be obtained from the supernatant of Bacillus cultures.

The subject invention further provides nucleotide sequences which encode the toxins of the subject invention. The subject invention further provides nucleotide sequences and methods useful in the identification and characterization of genes which encode pesticidal toxins.

In one embodiment, the subject invention concerns unique nucleotide sequences which are useful as hybridization probes and/or primers in PCR techniques. The primers produce characteristic gene fragments which can be used in the identification, characterization, and/or isolation of specific toxin genes. The nucleotide sequences of the subject invention encode toxins which are distinct from previously-described toxins.

In a specific embodiment, the subject invention provides new classes of toxins having advantageous pesticidal activities. These classes of toxins can be encoded by polynucleotide sequences which are characterized by their ability to hybridize with certain exemplified sequences and/or by their ability to be amplified by PCR using certain exemplified primers.

One aspect of the subject invention pertains to the identification and characterization of entirely new families of *Bacillus thuringiensis* toxins having advantageous pesticidal properties. Specific new toxin families of the subject invention include MIS-1, MIS-2, MIS-3, MIS-4, MIS-5, MIS-6, MIS-7, MIS-8, WAR-1, and SUP-1. These families of toxins, and the genes which encode them, can be characterized in terms of, for example, the size of the toxin or gene, the DNA or amino acid sequence, pesticidal activity, and/or antibody reactivity. With regard to the genes encoding the novel toxin families of the subject invention, the current disclosure provides unique hybridization probes and PCR primers which can be used to identify and characterize DNA within each of the exemplified families.

In one embodiment of the subject invention, Bacillus isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

A further aspect of the subject invention is the use of the disclosed nucleotide sequences as probes to detect genes encoding Bacillus toxins which are active against pests.

Further aspects of the subject invention include the genes and isolates identified using the methods and nucleotide sequences disclosed herein. The genes thus identified encode toxins active against pests. Similarly, the isolates will have activity against these pests. In a preferred embodiment, these pests are lepidopteran or coleopteran pests.

In a preferred embodiment, the subject invention concerns plants cells transformed with at least one polynucleotide sequence of the subject invention such that the transformed plant cells express pesticidal toxins in tissues consumed by target pests. As described herein, the toxins useful according to the subject invention may be chimeric toxins produced by combining portions of multiple toxins. In addition, mixtures and/or combinations of toxins can be used according to the subject invention.

Transformation of plants with the genetic constructs disclosed herein can be accomplished using techniques well known to those skilled in the art and would typically involve modification of the gene to optimize expression of the toxin in plants.

Alternatively, the Bacillus isolates of the subject invention, or recombinant microbes expressing the toxins described herein, can be used to control pests. In this regard, the invention includes the treatment of substantially intact Bacillus cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a forward primer, designated "the 339 forward primer," used according to the subject invention.

SEQ ID NO. 2 is a reverse primer, designated "the 339 reverse primer," used according to the subject invention.

SEQ ID NO. 3 is a nucleotide sequence encoding a toxin from B.t. strain PS36A.

SEQ ID NO. 4 is an amino acid sequence for the 36A toxin.

SEQ ID NO. 5 is a nucleotide sequence encoding a toxin from B.t. strain PS81F.

SEQ ID NO. 6 is an amino acid sequence for the 81F toxin.

SEQ ID NO. 7 is a nucleotide sequence encoding a toxin from B.t. strain Javelin 1990.

SEQ ID NO. 8 is an amino acid sequence for the Javelin 1990 toxin.

SEQ ID NO. 9 is a forward primer, designated "158C2 PRIMER A," used according to the subject invention.

SEQ ID NO. 10 is a nucleotide sequence encoding a portion of a soluble toxin from B.t. PS158C2.

SEQ ID NO. 11 is a forward primer, designated "49C PRIMER A," used according to the subject invention.

SEQ ID NO. 12 is a nucleotide sequence of a portion of a toxin gene from B.t. strain PS49C.

SEQ ID NO. 13 is a forward primer, designated "49C PRIMER B," used according to the subject invention.

SEQ ID NO. 14 is a reverse primer, designated "49C PRIMER C," used according to the subject invention.

SEQ ID NO. 15 is an additional nucleotide sequence of a portion of a toxin gene from PS49C.

SEQ ID NO. 16 is a forward primer used according to the subject invention.

SEQ ID NO. 17 is a reverse primer used according to the subject invention.

SEQ ID NO. 18 is a nucleotide sequence of a toxin gene from B.t. strain PS10E1.

SEQ ID NO. 19 is an amino acid sequence from the 10E1 toxin.

SEQ ID NO. 20 is a nucleotide sequence of a toxin gene from B.t. strain PS31J2.

SEQ ID NO. 21 is an amino acid sequence from the 31J2 toxin.

SEQ ID NO. 22 is a nucleotide sequence of a toxin gene from B.t. strain PS33D2.

SEQ ID NO. 23 is an amino acid sequence from the 33D2 toxin.

SEQ ID NO. 24 is a nucleotide sequence of a toxin gene from B.t. strain PS66D3.

SEQ ID NO. 25 is an amino acid sequence from the 66D3 toxin.

SEQ ID NO. 26 is a nucleotide sequence of a toxin gene from B.t. strain PS68F.

SEQ ID NO. 27 is an amino acid sequence from the 68F toxin.

SEQ ID NO. 28 is a nucleotide sequence of a toxin gene from B.t. strain PS69AA2.

SEQ ID NO. 29 is an amino acid sequence from the 69AA2 toxin.

SEQ ID NO. 30 is a nucleotide sequence of a toxin gene from B.t. strain PS168G1.

SEQ ID NO. 31 is a nucleotide sequence of a MIS toxin gene from B.t. strain PS177C8.

SEQ ID NO. 32 is an amino acid sequence from the 177C8-MIS toxin.

SEQ ID NO. 33 is a nucleotide sequence of a toxin gene from B.t. strain PS177I8.

SEQ ID NO. 34 is an amino acid sequence from the 177I8 toxin.

SEQ ID NO. 35 is a nucleotide sequence of a toxin gene from B.t. strain PS185AA2.

SEQ ID NO. 36 is an amino acid sequence from the 185AA2 toxin.

SEQ ID NO. 37 is a nucleotide sequence of a toxin gene from B.t. strain PS196F3.

SEQ ID NO. 38 is an amino acid sequence from the 196F3 toxin.

SEQ ID NO. 39 is a nucleotide sequence of a toxin gene from B.t. strain PS196J4.

SEQ ID NO. 40 is an amino acid sequence from the 196J4 toxin.

SEQ ID NO. 41 is a nucleotide sequence of a toxin gene from B.t. strain PS197T1.

SEQ ID NO. 42 is an amino acid sequence from the 197T1 toxin.

SEQ ID NO. 43 is a nucleotide sequence of a toxin gene from B.t. strain PS197U2.

SEQ ID NO. 44 is an amino acid sequence from the 197U2 toxin.

SEQ ID NO. 45 is a nucleotide sequence of a toxin gene from B.t. strain PS202E1.

SEQ ID NO. 46 is an amino acid sequence from the 202E1 toxin.

SEQ ID NO. 47 is a nucleotide sequence of a toxin gene from B.t. strain KB33.

SEQ ID NO. 48 is a nucleotide sequence of a toxin gene from B.t. strain KB38.

SEQ ID NO. 49 is a forward primer, designated "ICON-forward," used according to the subject invention.

SEQ ID NO. 50 is a reverse primer, designated "ICON-reverse," used according to the subject invention.

SEQ ID NO. 51 is a nucleotide sequence encoding a 177C8-WAR toxin gene from B.t. strain PS177C8.

SEQ ID NO. 52 is an amino acid sequence of a 177C8-WAR toxin from B.t. strain PS177C8.

SEQ ID NO. 53 is a forward primer, designated "SUP-1A," used according to the subject invention.

SEQ ID NO. 54 is a reverse primer, designated "SUP-1B," used according to the subject invention.

SEQ ID NOS. 55–110 are primers used according to the subject invention.

SEQ ID NO. 111 is the reverse complement of the primer of SEQ ID NO. 58.

SEQ ID NO. 112 is the reverse complement of the primer of SEQ ID NO. 60.

SEQ ID NO. 113 is the reverse complement of the primer of SEQ ID NO. 64.

SEQ ID NO. 114 is the reverse complement of the primer of SEQ ID NO. 66.

SEQ ID NO. 115 is the reverse complement of the primer of SEQ ID NO. 68.

SEQ ID NO. 116 is the reverse complement of the primer of SEQ ID NO. 70.

SEQ ID NO. 117 is the reverse complement of the primer of SEQ ID NO. 72.

SEQ ID NO. 118 is the reverse complement of the primer of SEQ ID NO. 76.

SEQ ID NO. 119 is the reverse complement of the primer of SEQ ID NO. 78.

SEQ ID NO. 120 is the reverse complement of the primer of SEQ ID NO. 80.

SEQ ID NO. 121 is the reverse complement of the primer of SEQ ID NO. 82.

SEQ ID NO. 122 is the reverse complement of the primer of SEQ ID NO. 84.

SEQ ID NO. 123 is the reverse complement of the primer of SEQ ID NO. 86.

SEQ ID NO. 124 is the reverse complement of the primer of SEQ ID NO. 88.

SEQ ID NO. 125 is the reverse complement of the primer of SEQ ID NO. 92.

SEQ ID NO. 126 is the reverse complement of the primer of SEQ ID NO. 94.

SEQ ID NO. 127 is the reverse complement of the primer of SEQ ID NO. 96.

SEQ ID NO. 128 is the reverse complement of the primer of SEQ ID NO. 98.

SEQ ID NO. 129 is the reverse complement of the primer of SEQ ID NO. 99.

SEQ ID NO. 130 is the reverse complement of the primer of SEQ ID NO. 100.

SEQ ID NO. 131 is the reverse complement of the primer of SEQ ID NO. 104.

SEQ ID NO. 132 is the reverse complement of the primer of SEQ ID NO. 106.

SEQ ID NO. 133 is the reverse complement of the primer of SEQ ID NO. 108.

SEQ ID NO. 134 is the reverse complement of the primer of SEQ ID NO. 110.

SEQ ID NO. 135 is a MIS-7 forward primer.

SEQ ID NO. 136 is a MIS-7 reverse primer.

SEQ ID NO. 137 is a MIS-8 forward primer.

SEQ ID NO. 138 is a MIS-8 reverse primer.

SEQ ID NO. 139 is a nucleotide sequence of a MIS-7 toxin gene designated 157C1-A from B.t. strain PS157C1.

SEQ ID NO. 140 is an amino acid sequence of a MIS-7 toxin designated 157C1-A from B.t. strain PS157C1.

SEQ ID NO. 141 is a nucleotide sequence of a MIS-7 toxin gene from B.t. strain PS201Z.

SEQ ID NO. 142 is a nucleotide sequence of a MIS-8 toxin gene from B.t. strain PS31F2.

SEQ ID NO. 143 is a nucleotide sequence of a MIS-8 toxin gene from B.t. strain PS185Y2.

SEQ ID NO. 144 is a nucleotide sequence of a MIS-1 toxin gene from B.t. strain PS33F1.

DETAILED DISCLOSURE OF THE INVENTION

The subject invention concerns materials and methods for the control of non-mammalian pests. In specific embodiments, the subject invention pertains to new *Bacillus thuringiensis* isolates and toxins which have activity against lepidopterans and/or coleopterans. The subject invention further concerns novel genes which encode pesticidal toxins and novel methods for identifying and characterizing Bacillus genes which encode toxins with useful properties. The subject invention concerns not only the polynucleotide sequences which encode these toxins, but also the use of these polynucleotide sequences to produce recombinant hosts which express the toxins. The proteins of the subject invention are distinct from protein toxins which have previously been isolated from *Bacillus thuringiensis*.

B.t. isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the B.t. strains are as follows:

TABLE 1

| Culture | Repository No. | Deposit Date | Patent No. |
|---|---|---|---|
| B.t. PS11B (MT274) | NRRL B-21556 | Apr. 18, 1996 | |
| B.t. PS24J | NRRL B-18881 | Aug. 30, 1991 | |
| B.t. PS31G1 (MT278) | NRRL B-21560 | Apr. 18, 1996 | |
| B.t. PS36A | NRRL B-18929 | Dec. 27, 1991 | |
| B.t. PS33F2 | NRRL B-18244 | Jul. 28, 1987 | 4,861,595 |
| B.t. PS40D1 | NRRL B-18300 | Feb. 3, 1988 | 5,098,705 |
| B.t. PS43F | NRRL B-18298 | Feb. 2, 1988 | 4,996,155 |
| B.t. PS45B1 | NRRL B-18396 | Aug. 16, 1988 | 5,427,786 |
| B.t. PS49C | NRRL B-21532 | Mar. 14, 1996 | |
| B.t. PS52A1 | NRRL B-18245 | Jul. 28, 1987 | 4,861,595 |
| B.t. PS62B1 | NRRL B-18398 | Aug. 16, 1988 | 4,849,217 |
| B.t. PS81A2 | NRRL B-18484 | Apr. 19, 1989 | 5,164,180 |
| B.t. PS81F | NRRL B-18424 | Oct. 7, 1988 | 5,045,469 |
| B.t. PS81GG | NRRL B-18425 | Oct. 11, 1988 | 5,169,629 |
| B.t PS81I | NRRL B-18484 | Apr. 19, 1989 | 5,126,133 |
| B.t. PS85A1 | NRRL B-18426 | Oct. 11, 1988 | |
| B.t. PS86A1 | NRRL B-18400 | Aug. 16, 1988 | 4,849,217 |
| B.t. PS86B1 | NRRL B-18299 | Feb. 2, 1988 | 4,966,765 |

TABLE 1-continued

| Culture | Repository No. | Deposit Date | Patent No. |
|---|---|---|---|
| B.t. PS86BB1 (MT275) | NRRL B-21557 | Apr. 18, 1996 | |
| B.t. PS86Q3 | NRRL B-18765 | Feb. 6, 1991 | 5,208,017 |
| B.t. PS86V1 (MT276) | NRRL B-21558 | Apr. 18, 1996 | |
| B.t. PS86W1 (MT277) | NRRL B-21559 | Apr. 18, 1996 | |
| B.t. PS89J3 (MT279) | NRRL B-21561 | Apr. 18, 1996 | |
| B.t. PS91C2 | NRRL B-18931 | Feb. 6, 1991 | |
| B.t. PS92B | NRRL B-18889 | Sep. 23, 1991 | 5,427,786 |
| B.t. PS101Z2 | NRRL B-18890 | Oct. 1, 1991 | 5,427,786 |
| B.t. PS122D3 | NRRL B-18376 | Jun. 9, 1988 | 5,006,336 |
| B.t. PS123D1 | NRRL B-21011 | Oct. 13, 1992 | 5,508,032 |
| B.t. PS157C1 (MT104) | NRRL B-18240 | Jul. 17, 1987 | 5,262,159 |
| B.t. PS158C2 | NRRL B-18872 | Aug. 27, 1991 | 5,268,172 |
| B.t. PS169E | NRRL B-18682 | Jul. 17, 1990 | 5,151,363 |
| B.t. PS177F1 | NRRL B-18683 | Jul. 17, 1990 | 5,151,363 |
| B.t. PS177G | NRRL B-18684 | Jul. 17, 1990 | 5,151,363 |
| B.t. PS185L2 | NRRL B-21535 | Mar. 14, 1996 | |
| B.t. PS185U2 (MT280) | NRRL B-21562 | Apr. 18, 1996 | |
| B.t. PS192M4 | NRRL B-18932 | Dec. 27, 1991 | 5,273,746 |
| B.t. PS201L1 | NRRL B-18749 | Jan. 9, 1991 | 5,298,245 |
| B.t. PS204C3 | NRRL B-21008 | Oct. 6, 1992 | |
| B.t. PS204G4 | NRRL B-18685 | Jul. 17, 1990 | 5,262,399 |
| B.t. PS242H10 | NRRL B-21439 | Mar. 14, 1996 | |
| B.t. PS242K17 | NRRB B-21540 | Mar. 14, 1996 | |
| B.t. PS244A2 | NRRB B-21541 | Mar. 14, 1996 | |
| B.t. PS244D1 | NRRL B-21542 | Mar. 14, 1996 | |
| B.t. PS10E1 | NRRL B-21862 | Oct. 24, 1997 | |
| B.t. PS31F2 | NRRL B-21876 | Oct. 24, 1997 | |
| B.t. PS31J2 | NRRL B-21009 | Oct. 13, 1992 | |
| B.t. PS33D2 | NRRL B-21870 | Oct. 24, 1997 | |
| B.t. PS66D3 | NRRL B-21858 | Oct. 24, 1997 | |
| B.t. PS68F | NRRL B-21857 | Oct. 24, 1997 | |
| B.t. PS69AA2 | NRRL B-21859 | Oct. 24, 1997 | |
| B.t. PS146D | NRRL B-21866 | Oct. 24, 1997 | |
| B.t. PS168G1 | NRRL B-21873 | Oct. 24, 1997 | |
| B.t. PS175I4 | NRRL B-21865 | Oct. 24, 1997 | |
| B.t. PS177C8a | NRRL B-21867 | Oct. 24, 1997 | |
| B.t. PS177I8 | NRRL B-21868 | Oct. 24, 1997 | |
| B.t. PS185AA2 | NRRL B-21861 | Oct. 24, 1997 | |

TABLE 1-continued

| Culture | Repository No. | Deposit Date | Patent No. |
|---|---|---|---|
| B.t. PS196J4 | NRRL B-21860 | Oct. 24, 1997 | |
| B.t. PS196F3 | NRRL B-21872 | Oct. 24, 1997 | |
| B.t. PS197T1 | NRRL B-21869 | Oct. 24, 1997 | |
| B.t. PS197U2 | NRRL B-21871 | Oct. 24, 1997 | |
| B.t. PS202E1 | NRRL B-21874 | Oct. 24, 1997 | |
| B.t. PS217U2 | NRRL B-21864 | Oct. 24, 1997 | |
| KB33 | NRRL B-21875 | Oct. 24, 1997 | |
| KB38 | NRRL B-21863 | Oct. 24, 1997 | |
| KB53A49-4 | NRRL B-21879 | Oct. 24, 1997 | |
| KB68B46-2 | NRRL B-21877 | Oct. 24, 1997 | |
| KB68B51-2 | NRRL B-21880 | Oct. 24, 1997 | |
| K1B68B55-2 | NRRL B-21878 | Oct. 24, 1997 | |
| PS80JJ1 | NRRL B-18679 | Jul. 17, 1990 | 5,151,363 |
| PS94R1 | NRRL B-21801 | Jul. 1, 1997 | |
| PS101DD | NRRL B-21802 | Jul. 1, 1997 | |
| PS202S | NRRL B-21803 | Jul. 1, 1997 | |
| PS213E5 | NRRL B-21804 | Jul. 1, 1997 | |
| PS218G2 | NRRL B-21805 | Jul. 1, 1997 | |
| PS33F1 | NRRL B-21977 | Apr. 24, 1998 | |
| PS71G4 | NRRL B-21978 | Apr. 24, 1998 | |
| PS86D1 | NRRL B-21979 | Apr. 24, 1998 | |
| PS185V2 | NRRL B-21980 | Apr. 24, 1998 | |
| PS191A21 | NRRL B-21981 | Apr. 24, 1998 | |
| PS201Z | NRRL B-21982 | Apr. 24, 1998 | |
| PS205A3 | NRRL B-21983 | Apr. 24, 1998 | |
| PS205C | NRRL B-21984 | Apr. 24, 1998 | |
| PS234E1 | NRRL B-21985 | Apr. 24, 1998 | |
| PS248N10 | NRRL B-21986 | Apr. 24, 1998 | |
| KB63B19-13 | NRRL B-21990 | Apr. 29, 1998 | |
| KB63B19-7 | NRRL B-21989 | Apr. 29, 1998 | |
| KB68B62-7 | NRRL B-21991 | Apr. 29, 1998 | |
| KB68B63-2 | NRRL B-21992 | Apr. 29, 1998 | |
| KB69A125-1 | NRRL B-21993 | Apr. 29, 1998 | |
| KB69A125-3 | NRRL B-21994 | Apr. 29, 1998 | |
| KB69A125-5 | NRRL B-21995 | Apr. 29, 1998 | |
| KB69A127-7 | NRRL B-21996 | Apr. 29, 1998 | |
| KB69A132-1 | NRRL B-21997 | Apr. 29, 1998 | |
| KB69B2-1 | NRRL B-21998 | Apr. 29, 1998 | |
| KB70B5-3 | NRRL B-21999 | Apr. 29, 1998 | |
| KB71A125-15 | NRRL B-30001 | Apr. 29, 1998 | |
| KB71A35-6 | NRRL B-30000 | Apr. 29, 1998 | |
| KB71A72-1 | NRRL B-21987 | Apr. 29, 1998 | |
| KB71A134-2 | NRRL B-21988 | Apr. 29, 1998 | |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Many of the strains useful according to the subject invention are readily available by virtue of the issuance of patents disclosing these strains or by their deposit in public collections or by their inclusion in commercial products. For example, the B.t. strain used in the commercial product, Javelin, and the HD isolates are all publicly available.

Mutants of the isolates referred to herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

In one embodiment, the subject invention concerns materials and methods including nucleotide primers and probes for isolating, characterizing, and identifying Bacillus genes encoding protein toxins which are active against non-mammalian pests. The nucleotide sequences described herein can also be used to identify new pesticidal Bacillus isolates. The invention further concerns the genes, isolates, and toxins identified using the methods and materials disclosed herein.

The new toxins and polynucleotide sequences provided here are defined according to several parameters. One characteristic of the toxins described herein is pesticidal activity. In a specific embodiment, these toxins have activity against coleopteran and/or lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. The toxins provided herein can also be identified based on their immunoreactivity with certain antibodies.

An important aspect of the subject invention is the identification and characterization of new families of Bacillus toxins, and genes which encode these toxins. These families have been designated MIS-1, MIS-2, MIS-3, MIS-4, MIS-5, MIS-6, MIS-7, MIS-8, WAR-1, and SUP-1. Toxins within these families, as well as genes encoding toxins within these families, can readily be identified as described herein by, for example, size, amino acid or DNA sequence, and antibody reactivity. Amino acid and DNA sequence characteristics include homology with exemplified sequences, ability to hybridize with DNA probes, and ability to be amplified with specific primers.

The MIS-1 family of toxins includes toxins from isolates PS68F and PS33F1. Also provided are hybridization probes and PCR primers which specifically identify genes falling in the MIS-1 family.

A second family of toxins identified herein is the MIS-2 family. This family includes toxins which can be obtained from isolates PS66D3, PS197T1, and PS31J2. The subject invention further provides probes and primers for the identification of MIS-2 toxins and genes.

A third family of toxins identified herein is the MIS-3 family. This family includes toxins which can be obtained from B.t. isolates PS69AA2 and PS33D2. The subject invention further provides probes and primers for identification of the MIS-3 genes and toxins.

Polynucleotide sequences encoding MIS-4 toxins can be obtained from the B.t. isolate designated PS197U2. The subject invention further provides probes and primers for the identification of genes and toxins in this family.

A fifth family of toxins identified herein is the MIS-5 family. This family includes toxins which can be obtained from B.t. isolates KB33 and KB38. The subject invention further provides probes and primers for identification of the MIS-5 genes and toxins.

A sixth family of toxins identified herein is the MIS-6 family. This family includes toxins which can be obtained from B.t. isolates PS196F3, PS168G1, PS196J4, PS202E1, PS10E1, and PS185AA2. The subject invention further provides probes and primers for identification of the MIS-6 genes and toxins.

A seventh family of toxins identified herein is the MIS-7 family. This family includes toxins which can be obtained from B.t. isolates PS157C1, PS205C, and PS201Z. The subject invention further provides probes and primers for identification of the MIS-7 genes and toxins.

An eighth family of toxins identified herein is the MIS-8 family. This family includes toxins which can be obtained from B.t. isolates PS31F2 and PS185Y2. The subject invention further provides probes and primers for identification of the MIS-8 genes and toxins.

In a preferred embodiment, the genes of the MIS family encode toxins having a molecular weight of about 70 to about 100 kDa and, most preferably, the toxins have a size of about 80 kDa. Typically, these toxins are soluble and can be obtained from the supernatant of Bacillus cultures as described herein. These toxins have toxicity against non-mammalian pests. In a preferred embodiment, these toxins have activity against coleopteran pests. The MIS proteins are further useful due to their ability to form pores in cells. These proteins can be used with second entities including, for example, other proteins. When used with a second entity, the MIS protein will facilitate entry of the second agent into a target cell. In a preferred embodiment, the MIS protein interacts with MIS receptors in a target cell and causes pore formation in the target cell. The second entity may be a toxin or another molecule whose entry into the cell is desired.

The subject invention further concerns a family of toxins designated WAR-1. The WAR-1 toxins typically have a size of about 30–50 kDa and, most typically, have a size of about 40 kDa. Typically, these toxins are soluble and can be obtained from the supernatant of Bacillus cultures as described herein. The WAR-1 toxins can be identified with primers described herein as well as with antibodies. In a specific embodiment, the antibodies can be raised to, for example, toxin from isolate PS177C8.

An additional family of toxins provided according to the subject invention are the toxins designated SUP-1. Typically, these toxins are soluble and can be obtained from the supernatant of Bacillus cultures as described herein. In a preferred embodiment, the SUP-1 toxins are active against lepidopteran pests. The SUP-1 toxins typically have a size of about 70–100 kDa and, preferably, about 80 kDa. The SUP-1 family is exemplified herein by toxins from isolates PS49C and PS158C2. The subject invention provides probes and primers useful for the identification of toxins and genes in the SUP-1 family The subject invention further provides specific Bacillus toxins and genes which did not fall into any of the new families disclosed herein. These specific toxins and genes include toxins and genes which can be obtained from PS177C8 and PS177I8.

Toxins in the MIS, WAR, and SUP families are all soluble and can be obtained as described herein from the supernatant of Bacillus cultures. These toxins can be used alone or in combination with other toxins to control pests. For example, toxins from the MIS families may be used in conjunction with WAR-type toxins to achieve control of pests, particularly coleopteran pests. These toxins may be used, for example, with δ-endotoxins which are obtained from Bacillus isolates.

Table 2 provides a summary of the novel families of toxins and genes of the subject invention. Each of the eight MIS families is specifically exemplified herein by toxins which can be obtained from particular B.t. isolates as shown in Table 2. Genes encoding toxins in each of these families can be identified by a variety of highly specific parameters, including the ability to hybridize with the particular probes set forth in Table 2. Sequence identity in excess of about 80% with the probes set forth in Table 2 can also be used to identify the genes of the various families. Also exemplified are particular primer pairs which can be used to amplify the genes of the subject invention. A portion of a gene within the indicated families would typically be amplifiable with at least one of the enumerated primer pairs. In a preferred embodiment, the amplified portion would be of approximately the indicated fragment size. Primers shown in Table 2 consist of polynucleotide sequences which encode peptides as shown in the sequence listing attached hereto. Additional primers and probes can readily be constructed by those skilled in the art such that alternate polynucleotide sequences encoding the same amino acid sequences can be used to identify and/or characterize additional genes encoding pesticidal toxins. In a preferred embodiment, these additional toxins, and their genes, could be obtained from Bacillus isolates.

TABLE 2

| Family | Isolates | Probes (SEQ ID NO.) | Primer Pairs (SEQ ID NOS.) | Fragment size (nt) |
|---|---|---|---|---|
| MIS-1 | PS68F, PS33F1 | 26, 144 | 56 and 111 | 69 |
| | | | 56 and 112 | 506 |
| | | | 58 and 112 | 458 |
| MIS-2 | PS66D3, PS197T1, PS31J2 | 24, 41, 20 | 62 and 113 | 160 |
| | | | 62 and 114 | 239 |
| | | | 62 and 115 | 400 |
| | | | 62 and 116 | 509 |
| | | | 62 and 117 | 703 |
| | | | 64 and 114 | 102 |
| | | | 64 and 115 | 263 |
| | | | 64 and 116 | 372 |
| | | | 64 and 117 | 566 |
| | | | 66 and 115 | 191 |
| | | | 66 and 116 | 300 |
| | | | 66 and 117 | 494 |
| | | | 68 and 116 | 131 |
| | | | 68 and 117 | 325 |
| | | | 70 and 117 | 213 |
| MIS-3 | PS69AA2, PS33D2 | 28, 22 | 74 and 118 | 141 |
| | | | 74 and 119 | 376 |
| | | | 74 and 120 | 389 |
| | | | 74 and 121 | 483 |
| | | | 74 and 122 | 715 |
| | | | 74 and 123 | 743 |
| | | | 74 and 124 | 902 |
| | | | 76 and 119 | 253 |
| | | | 76 and 120 | 266 |
| | | | 76 and 121 | 360 |
| | | | 76 and 122 | 592 |
| | | | 76 and 123 | 620 |
| | | | 76 and 124 | 779 |
| | | | 78 and 120 | 31 |
| | | | 78 and 121 | 125 |
| | | | 78 and 122 | 357 |
| | | | 78 and 123 | 385 |
| | | | 78 and 124 | 544 |
| | | | 80 and 121 | 116 |
| | | | 80 and 122 | 348 |
| | | | 80 and 123 | 376 |
| | | | 80 and 124 | 535 |
| | | | 82 and 122 | 252 |
| | | | 82 and 123 | 280 |
| | | | 82 and 124 | 439 |
| | | | 84 and 123 | 46 |
| | | | 84 and 124 | 205 |
| | | | 86 and 124 | 177 |
| MIS-4 | PS197U2 | 43 | 90 and 125 | 517 |
| | | | 90 and 126 | 751 |
| | | | 90 and 127 | 821 |
| | | | 92 and 126 | 258 |
| | | | 92 and 127 | 328 |
| | | | 94 and 127 | 92 |
| MIS-5 | KB33, KB38 | 47, 48 | 97 and 128 | 109 |
| | | | 97 and 129 | 379 |
| | | | 97 and 130 | 504 |
| | | | 98 and 129 | 291 |
| | | | 98 and 130 | 416 |
| | | | 99 and 130 | 144 |
| MIS-6 | PS196F3, PS168G1, PS196J4, PS202E1, PS10E1, PS185AA2 | 18,30,35,37, 39,45 | 102 and 131 | 66 |
| | | | 102 and 132 | 259 |
| | | | 102 and 133 | 245 |
| | | | 102 and 134 | 754 |
| | | | 104 and 132 | 213 |
| | | | 104 and 133 | 199 |
| | | | 104 and 134 | 708 |
| | | | 106 and 133 | 31 |
| | | | 106 and 134 | 518 |
| | | | 108 and 134 | 526 |
| MIS-7 | PS205C, PS157C1 (157C1-A), PS201Z | 139, 141 | 135 and 136 | 598 |
| MIS-8 | PS31F2, PS185Y2 | 142,143 | 137 and 138 | 585 |
| SUP-1 | PS49C, PS158C2 | 10, 12, 15 | 53 and 54 | 370 |

Furthermore, chimeric toxins may be used according to the subject invention. Methods have been developed for making useful chimeric toxins by combining portions of B.t. proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041; Ge, A. Z., D. Rivers, R. Milne, D. H. Dean (1991) *J. Biol. Chem.* 266:17954–17958; Schnepf, H. E., K. Tomczak, J. P. Ortega, H. R. Whiteley (1990) *J. Biol. Chem.* 265:20923–20930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention is meant to include chimeric proteins that utilize the novel sequences identified in the subject application.

With the teachings provided herein, one skilled in the art could readily produce and use the various toxins and polynucleotide sequences described herein.

Genes and toxins. The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one Bacillus toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It is apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from Bacillus isolates and/or DNA libraries using the teachings provided herein. There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other Bacillus toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins are within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The δ-endotoxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

Recombinant hosts. The toxin-encoding genes of the subject invention can be introduced into a wide variety of microbial or plant hosts. Expression of the toxin gene results, directly or indirectly, in the production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

Where the Bacillus toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a Bacillus gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Synthetic genes which are functionally equivalent to the toxins of the subject invention can also be used to transform hosts. Methods for the production of synthetic genes can be found in, for example, U.S. Pat. No. 5,380,831.

Treatment of cells. As mentioned above, Bacillus or recombinant cells expressing a Bacillus toxin can be treated to prolong the toxin activity and stabilize the cell. The pesticide microcapsule that is formed comprises the Bacillus toxin within a cellular structure that has been stabilized and will protect the toxin when the microcapsule is applied to the environment of the target pest. Suitable host cells may include either prokaryotes or eukaryotes. As hosts, of particular interest will be the prokaryotes and the lower eukaryotes, such as fungi. The cell will usually be intact and be substantially in the proliferative form when treated, rather than in a spore form.

Treatment of the microbial cell, e.g., a microbe containing the Bacillus toxin gene, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and formulations for control of pests. Control of pests using the isolates, toxins, and genes of the subject invention can be accomplished by a variety of methods known to those skilled in the art. These methods include, for example, the application of Bacillus isolates to the pests (or their location), the application of recombinant microbes to the pests (or their locations), and the transformation of plants with genes which encode the pesticidal toxins of the subject invention. Transformations can be made by those skilled in the art using standard techniques. Materials necessary for these transformations are disclosed herein or are otherwise readily available to the skilled artisan.

Formulated bait granules containing an attractant and the toxins of the Bacillus isolates, or recombinant microbes comprising the genes obtainable from the Bacillus isolates disclosed herein, can be applied to the soil. Formulated product can also be applied as a seed-coating or root treatment or total plant treatment at later stages of the crop cycle. Plant and soil treatments of Bacillus cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations that contain cells will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Polynucleotide probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA, DNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the Bacillus isolate all DNA segments homologous with the disclosed nucleotide sequences. Thus, it is possible, without the aid of biological analysis, to know in advance the probable activity of many new Bacillus isolates, and of the individual gene products expressed by a given Bacillus isolate. Such a probe analysis provides a rapid method for identifying potentially commercially valuable insecticidal toxin genes within the multifarious subspecies of B.t.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probes may be made inherently fluorescent as described in International Application No. WO 93/16094.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes,* Stockton Press, New York, N.Y., pp. 169–170.

As used herein "moderate to high stringency" conditions for hybridization refers to conditions which achieve the same, or about the same, degree of specificity of hybridization as the conditions employed by the current applicants. Examples of moderate and high stringency conditions are provided herein. Specifically, hybridization of immobilized DNA on Southern blots with 32P-labeled gene-specific probes was performed by standard methods (Maniatis et al.). In general, hybridization and subsequent washes were carried out under moderate to high stringency conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology,* R. Wu, L. Grossman and K. Moldave [eds.] Academic Press, New York 100:266–285).

Tm=81.5° C.+16.6 Log[Na+]+0.41 (%G+C)−0.61 (%formamide)−600/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

Tm (° C.)=2(number T/A base pairs)+4(number G/C base pairs) (Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature
Low: 1 or 2×SSPE, 42° C.
Moderate: 0.2× or 1×SSPE, 65° C.
High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant probe to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan.

All of the U.S. patents cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing of Bacillus Isolates Useful According to the Invention

Growth of cells. The cellular host containing the Bacillus insecticidal gene may be grown in any convenient nutrient medium. These cells may then be harvested in accordance with conventional ways. Alternatively, the cells can be treated prior to harvesting.

The Bacillus cells of the invention can be cultured using standard art media and fermentation techniques. During the fermentation cycle, the bacteria can be harvested by first separating the Bacillus vegetative cells, spores, crystals, and lysed cellular debris from the fermentation broth by means well known in the art. Any Bacillus spores or crystal δ-endotoxins formed can be recovered employing well-known techniques and used as a conventional δ-endotoxin B.t. preparation. The supernatant from the fermentation process contains toxins of the present invention. The toxins are isolated and purified employing well-known techniques.

A subculture of Bacillus isolates, or mutants thereof, can be used to inoculate the following medium, known as TB broth:

| | |
|---|---|
| Tryptone | 12 g/l |
| Yeast Extract | 24 g/l |
| Glycerol | 4 g/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24–36 hours.

The above procedure can be readily scaled up to large fermentors by procedures well known in the art.

The Bacillus obtained in the above fermentation, can be isolated by procedures well known in the art. A frequently-used procedure is to subject the harvested fermentation broth to separation techniques, e.g., centrifugation. In a specific embodiment, Bacillus proteins useful according the present invention can be obtained from the supernatant. The culture supernatant containing the active protein(s) can be used in bioassays.

Alternatively, a subculture of Bacillus isolates, or mutants thereof, can be used to inoculate the following peptone, glucose, salts medium:

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| pH 7.2 | |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The Bacillus spores and/or crystals, obtained in the above fermentation, can be isolated by procedures well known in the art. A frequently-used procedure is to subject the harvested fermentation broth to separation techniques, e.g., centrifugation.

EXAMPLE 2

Isolation and Preparation of Cellular DNA for PCR

DNA can be prepared from cells grown on Spizizen's agar, or other minimal or enriched agar known to those skilled in the art, for approximately 16 hours. Spizizen's casamino acid agar comprises 23.2 g/l Spizizen's minimal salts [(NH$_4$)$_2$SO$_4$, 120 g; K$_2$HPO$_4$, 840 g; KH$_2$PO$_4$, 360 g; sodium citrate, 60 g; MgSO$_4$·7H$_2$O, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 cm$^2$ patch of cells can be scraped from the agar into 300 μl of 10 mM Tris-HCl (pH 8.0)-1 mM EDTA. Proteinase K was added to 50 μg/ml and incubated at 55° C. for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000×g in an Eppendorf microfuge at room temperature for 5 minutes to remove cellular debris. The supernatants containing crude DNA were transferred to fresh tubes and frozen at −20° C. until used in PCR reactions.

Alternatively, total cellular DNA may be prepared from plate-grown cells using the QIAamp Tissue Kit from Qiagen (Santa Clarita, Calif.) following instructions from the manufacturer.

EXAMPLE 3

Use of PCR Primers to Characterize and/or Identify Toxin Genes

Two primers useful in PCR procedures were designed to identify genes that encode pesticidal toxins. Preferably, these toxins are active against lepidopteran insects. The DNA from 95 B.t. strains was subjected to PCR using these primers. Two clearly distinguishable molecular weight bands were visible in "positive" strains, as outlined below. The frequency of strains yielding a 339 bp fragment was 29/95 (31%). This fragment is referred to herein as the "339 bp fragment" even though some small deviation in the exact number of base pairs may be observed.

```
GARCCRTGGA AAGCAAATAA TAARAATGC      (SEQ ID NO. 1)

AAARTTATCT CCCCAWGCTT CATCTCCATT TTG (SEQ ID NO. 2)
```

The strains which were positive for the 339 bp fragment (29 strains) were: PS11B, PS31G1, PS36A, PS49C, PS81A2, PS81F, PS81GG, PS81I, PS85A1, PS86BB1, PS86V1, PS86W1, PS89J3, PS91C2, PS94R1, PS101DD, PS158C2, PS185U2, PS192M4, PS202S, PS213E5, PS218G2, PS244A2, HD29, HD110, HD129, HD525, HD573a, and Javelin 1990.

The 24 strains which gave a larger (approximately 1.2 kb) fragment were: PS24J, PS33F2, PS45B1, PS52A1, PS62B1, PS80PP3, PS86A1, PS86Q3, PS88F16, PS92B, PS101Z2, PS123D1, PS157C1, PS169E, PS177F1, PS177G, PS185L2, PS201L1, PS204C3, PS204G4, PS242H10, PS242K17, PS244A2, PS244D1.

It was found that Bacillus strains producing lepidopteran-active proteins yielded only the 339 bp fragment. Few, if any, of the strains amplifying the approximately 1.2 kb fragment had known lepidopteran activity, but rather were coleopteran-, mite-, and/or nematode-active B.t. crystal protein producing strains.

EXAMPLE 4

DNA Sequencing of Toxin Genes Producing the 339 Fragment

PCR-amplified segments of toxin genes present in Bacillus strains can be readily sequenced. To accomplish this, amplified DNA fragments can be first cloned into the PCR DNA TA-cloning plasmid vector, pCRII, as described by the supplier (Invitrogen, San Diego, Calif.). Individual pCRII clones from the mixture of amplified DNA fragments from each Bacillus strain are chosen for sequencing. Colonies are lysed by boiling to release crude plasmid DNA. DNA templates for automated sequencing are amplified by PCR using vector-specific primers flanking the plasmid multiple cloning sites. These DNA templates are sequenced using Applied Biosystems (Foster City, Calif.) automated sequencing methodologies. The polypeptide sequences can be deduced from these nucleotide sequences.

DNA from three of the 29 B.t. strains which amplified the 339 bp fragments were sequenced. A DNA sequence encoding a toxin from strain PS36A is shown in SEQ ID NO. 3. An amino acid sequence for the 36A toxin is shown in SEQ ID. NO 4. A DNA sequence encoding a toxin from strain PS81F is shown in SEQ ID NO. 5. An amino acid sequence for the 81F toxin is shown in SEQ ID. NO 6. A DNA sequence encoding a toxin from strain Javelin 1990 is shown in SEQ ID NO. 7. An amino acid sequence for the Javelin 1990 toxin is shown in SEQ ID. NO 8.

EXAMPLE 5

Determination of DNA Sequences from Additional Genes Encoding Toxins from Strains PS158C2 and PS49C Genes encoding novel toxins were identified from isolates PS158C2 and PS49C as follows: Total cellular DNA was extracted from B.t. strains using Qiagen (Santa Clarita, Calif.) Genomic-tip 500/G DNA extraction kits according to the supplier and was subjected to PCR using the oligonucleotide primer pairs listed below. Amplified DNA fragments were purified on Qiagen PCR purification columns and were used as templates for sequencing.

For PS158C2, the primers used were as follows.

```
158C2 PRIMER A:
GCTCTAGAAGGAGGTAACTTATGAACAAGAATAATACTAAATTAAGC (SEQ ID NO. 9)

339 reverse:
AAARTTATCT CCCCAWGCTT CATCTCCATT TTG (SEQ ID NO. 2)
```

The resulting PCR-amplified DNA fragment was approximately 2 kbp in size. This DNA was partially sequenced by dideoxy chain termination using automated DNA sequencing technology (Perkin Elmer/Applied Biosystems, Foster City, Calif.). A DNA sequence encoding a portion of a soluble toxin from PS158C2 is shown in SEQ ID NO. 10.

For PS49C, two separate DNA fragments encoding parts of a novel toxin gene were amplified and sequenced. The first fragment was amplified using the following primer pair:

```
49C PRIMER A:
CATCCTCCCTACACTTTCTAA (SEQ ID NO. 11)

339 reverse:
AAARTTATCT CCCCAWGCTT CATCTCCATT TTG (SEQ ID NO. 2)
```

The resulting approximately 1 kbp DNA fragment was used as a template for automated DNA sequencing. A sequence of a portion of a toxin gene from strain PS49C is shown in SEQ ID NO. 12.

The second fragment was amplified using the following primer pair:

```
49C PRIMER B:
AAATTATGCGTAAGTCTGC (SEQ ID NO. 13)

49C PRIMER C:
TTGATCCGGACATAATAAT (SEQ ID NO. 14)
```

The resulting approximately 0.57 kbp DNA fragment was used as a template for automated DNA sequencing. An additional sequence of a portion of the toxin gene from PS49C is shown in SEQ ID NO. 15.

EXAMPLE 6

Additional Primers Useful for Characterizing and/or Identifying Toxin Genes

The following primer pair can be used to identify and/or characterize genes of the SUP-1 family:

```
SUP-1A:
GGATTCGTTATCAGAAA (SEQ ID NO. 53)

SUP-1B:
CTGTYGCTAACAATGTC (SEQ ID NO. 54)
```

These primers can be used in PCR procedures to amplify a fragment having a predicted size of approximately 370 bp. A band of the predicted size was amplified from strains PS158C2 and PS49C.

EXAMPLE 7

Additional Primers Useful for Characterizing and/or Identifying Toxin Genes

Another set of PCR primers can be used to identify and/or characterize additional genes encoding pesticidal toxins. The sequences of these primers were as follows:

GGRTTAMTTGGRTAYTATTT (SEQ ID NO. 16)
ATATCKWAYATTKGCATTTA (SEQ ID NO. 17)

Redundant nucleotide codes used throughout the subject disclosure are in accordance with the IUPAC convention and include:

R=A or G
M=A or C
Y=C or T
K=G or T
W=A or T

EXAMPLE 8

Identification and Sequencing of Genes Encoding Novel Soluble Protein Toxins from Bacillus Strains PCR using primers SEQ ID NO. 16 and SEQ ID NO. 17 was performed on total cellular genomic DNA isolated from a broad range of Bt strains. Those samples yielding an approximately 1 kb band were selected for characterization by DNA sequencing. Amplified DNA fragments were first cloned into the PCR DNA TA-cloning plasmid vector, pCR2.1, as described by the supplier (Invitrogen, San Diego, Calif.). Plasmids were isolated from recombinant clones and tested for the presence of an approximately 1 kbp insert by PCR using the plasmid vector primers, T3 and T7.

The following strains yielded the expected band of approximately 1000 bp, thus indicating the presence of a MIS-type toxin gene: PS10E1, PS31J2, PS33D2, PS66D3, PS68F, PS69AA2, PS168G1, PS177C8, PS177I8, PS185AA2, PS196F3, PS196J4, PS197T1, PS197U2, PS202E1, KB33, KB38, PS33F1, PS157C1 (157C1-A), PS201Z, PS31F2, and PS185Y2.

Plasmids were then isolated for use as sequencing templates using QIAGEN (Santa Clarita, Calif.) miniprep kits as described by the supplier. Sequencing reactions were performed using the Dye Terminator Cycle Sequencing Ready Reaction Kit from PE Applied Biosystems. Sequencing reactions were run on a ABI PRISM 377 Automated Sequencer. Sequence data was collected, edited, and assembled using the ABI PRISM 377 Collection, Factura, and AutoAssembler software from PE ABI.

DNA sequences were determined for portions of novel toxin genes from the following isolates: PS10E1, PS31J2, PS33D2, PS66D3, PS68F, PS69AA2, PS168G1, PS177C8, PS177I8, PS185AA2, PS196F3, PS196J4, PS197T1, PS197U2, PS202E1, KB33, KB38, PS33F1, PS157C1 (157C1-A), PS201Z, PS31F2, and PS185Y2. Polypeptide sequences were deduced for portions of the encoded, novel soluble toxins from the following isolates: PS10E1, PS31J2, PS33D2, PS66D3, PS68F, PS69AA2, PS177C8, PS177I8, PS185AA2, PS196F3, PS196J4, PS197T1, PS197U2, PS202E1, and PS157C1 (toxin 157C1-A). These nucleotide sequences and amino acid sequences are shown in SEQ ID NOS. 18 to 48 and SEQ ID NOS. 139–144.

EXAMPLE 9

Restriction Fragment Length Polymorphism (RFLP) of Toxins from *Bacillus thuringiensis* Strains Total cellular DNA was prepared from various *Bacillus thuringiensis* (B.t.) strains grown to an optical density of 0.5–0.8 at 600 nm visible light. DNA was extracted using the Qiagen Genomic-tip 500/G kit and Genomic DNA Buffer Set according to protocol for Gram positive bacteria (Qiagen Inc.; Valencia, Calif.).

Standard Southern hybridizations using $^{32}$P-labeled probes were used to identify and characterize novel toxin genes within the total genomic DNA preparations. Prepared total genomic DNA was digested with various restriction enzymes, electrophoresed on a 1% agarose gel, and immobilized on a supported nylon membrane using standard methods (Maniatis et al.).

PCR-amplified DNA fragments 1.0–1.1 kb in length were gel purified for use as probes. Approximately 25 ng of each DNA fragment was used as a template for priming nascent DNA synthesis using DNA polymerase I Klenow fragment (New England Biolabs), random hexanucleotide primers (Boehringer Mannheim) and $^{32}$PdCTP.

Each $^{32}$P-labeled fragment served as a specific probe to its corresponding genomic DNA blot. Hybridizations of immobilized DNA with randomly labeled $^{32}$p probes were performed in standard aqueous buffer consisting of 5×SSPE, 5×Denhardt's solution, 0.5% SDS, 0.1 mg/ml at 65° C.

overnight. Blots were washed under moderate stringency in 0.2×SSC, 0.1% SDS at 65° C. and exposed to film. RFLP data showing specific hybridization bands containing all or part of the novel gene of interest was obtained for each strain.

TABLE 4

| (Strain)/ Gene Name | Probe Seq I.D. Number | RFLP Data (approximate band sizes) |
|---|---|---|
| (PS)10E1 | 18 | EcoRI: 4 and 9 kbp, EcoRV: 4.5 and 6 kbp, KpnI: 12 and 24 kbp, SacI: 13 and 24 kbp, SalI: >23 kbp, XbaI: 5 and 15 kbp |
| (PS)31J2 | 20 | ApaI: >23 kbp, BglII: 6.5 kbp, PstI: >23 kbp, SacI: >23 kbp, SalI: >23 kbp, XbaI: 5 kbp |
| (PS)33D2 | 22 | EcoRI: 10 kbp, EcoRV: 15 kbp, HindIII: 18 kbp, KpnI: 9.5 kbp, PstI: 8 kbp |
| (PS)66D3 | 24 | BamHI: 4.5 kbp, HindIII: >23 kbp, KpnI: 23 kbp, PstI: 15 kbp, XbaI: >23 kbp |
| (PS)68F | 26 | EcoRI: 8.5 and 15 kbp, EcoRV: 7 and 18 kbp, HindIII: 2.1 and 9.5 kbp, PstI: 3 and 18 kbp, XbaI: 10 and 15 kbp |
| (PS)69AA2 | 28 | EcoRV: 9.5 kbp, HindIII: 18 kbp, KpnI: 23 kbp, NheI: >23 kbp, PstI: 10 kbp, SalI: >23 kbp |
| (PS)168G1 | 30 | EcoRI: 10 kbp, EcoRV: 3.5 kbp, NheI: 20 kbp, PstI: 20 kbp, SalI: >23 kbp, XbaI: 15 kbp |
| (PS)177I8 | 33 | BamHI: >23 kbp, EcoRI: 10 kbp, HindIII: 2 kbp, SalI:>23 kbp, XbaI: 3.5 kbp |
| (PS)185AA2 | 35 | EcoRI: 7 kbp, EcoRV: 10 kbp (&3.5 kbp?), NheI: 4 kbp, PstI: 3 kbp, SalI: >23 kbp, XbaI: 4 kbp |
| (PS)196F3 | 37 | EcoRI: 8 kbp, EcoRV: 9 kbp, NheI: 18 kbp, PstI: 18 kbp, SalI: 20 kbp, XbaI: 7 kbp |
| (PS)196J4 | 39 | BamHI: >23 kbp, EcoRI: 3.5 and 4.5 kbp, PstI: 9 and 24 kbp, SalI: >23 kbp, XbaI: 2.4 kbp and 12 kbp |
| (PS)197T1 | 41 | HindIII: 10 kbp, KpnI: 20 kbp, PstI: 20 kbp, SacI: 20 kbp, SpeI: 15 kbp, XbaI: 5 kbp |
| (PS)197U2 | 43 | EcoRI: 5 kbp, EcoRV: 1.9 kbp, NheI: 20 kbp, PstI: 23 kbp, SalI: >23 kbp, XbaI: 7 kbp |
| (PS)202E1 | 45 | EcoRV: 7 kbp, KpnI: 12 kbp, NheI: 10 kbp, PstI: 15 kbp, SalI: 23 kbp, XbaI: 1.8 kbp |
| KB33 | 47 | EcoRI: 9 kbp, EcoRV: 6 kbp, HindIII: 8 kbp, KpnI: >23 kbp, NheI: 22 kbp, SalI: >23 kbp |
| KB38 | 48 | BamHI: 5.5 kbp, EcoRV: 22 kbp, HindIII: 2.2 kbp, NheI: 20 kbp PstI: >23 kbp |

In separate experiments, alternative probes for MIS and WAR genes were used to detect novel toxin genes on Southern blots of genomic DNA by $^{32}$P autoradiography or by non-radioactive methods using the DIG nucleic acid labeling and detection system (Boehringer Mannheim; Indianapolis, Ind.). DNA fragments approximately 2.6 kbp (PS177C8 MIS toxin gene; SEQ ID NO. 31) and 1.3 kbp (PS177C8 WAR toxin gene; SEQ ID NO. 51) in length were PCR amplified from plasmid pMYC2450 and used as the probes for all strains listed. Fragments were gel purified and approximately 25 ng of each DNA fragment was randomly labeled with $^{32}$P for radioactive detection or approximately 300 ng of each DNA fragment was randomly labeled with the DIG High Prime kit for nonradioactive detection. Hybridization of immobilized DNA with randomly labeled $^{32}$P probes were performed in standard formamide conditions: 50% formamide, 5×SSPE, 5×Denhardt's solution, 2% SDS, 0.1 mg/ml sonicated sperm DNA at 42° C. overnight. Blots were washed under low stringency in 2×SSC, 0.1% SDS at 42° C. and exposed to film. RFLP data showing DNA bands containing all or part of the novel gene of interest was obtained for each strain.

RFLP data using Probe 177C8-MIS (SEQ ID NO. 31) were as follows:

TABLE 5

| RFLP Class | Strain Name(s) | RFLP Data (approximate band size in base pairs) |
|---|---|---|
| A | 177C8, 74H3, 66D3 | HindIII: 2,454; 1,645<br>XbaI: 14,820; 9,612; 8,138; 5,642; 1,440 |
| B | 177I8 | HindIII: 2,454<br>XbaI: 3,500 (very faint 7,000) |
| C | 66D3 | HindIII: 2,454 (faint 20,000)<br>XbaI: 3,500 (faint 7,000) |
| D | 28M, 31F2, 71G5, 71G7, 71I1, 71N1, 146F, 185Y2, 201JJ7, KB73, KB68B46-2, KB71A35-4, KB71A116-1 | HindIII: 11,738; 7,614<br>XbaI: 10,622; 6,030 |
| D₁ | 70B2, 71C2 | HindIII: 11,738; 8,698; 7,614<br>XbaI: 11,354; 10,622; 6,030 |
| E | KB68B51-2, KB68B55-2 | HindIII: 6,975; 2,527<br>XbaI: 10,000; 6,144 |
| F | KB53A49-4 | HindIII: 5,766<br>XbaI: 6,757 |
| G | 86D1 | HindIII: 4,920<br>XbaI: 11,961 |
| H | HD573B, 33F1, 67B3 | HindIII: 6,558; 1,978<br>XbaI: 7,815; 6,558 |
| I | 205C, 40C1 | HindIII: 6,752<br>XbaI: 4,618 |
| J | 130A3, 143A2, 157C1 | HindIII: 9,639; 3,943; 1,954; 1,210<br>XbaI: 7,005; 6,165; 4,480; 3,699 |
| K | 201Z | HindIII: 9,639; 4,339<br>XbaI: 7,232; 6,365 |
| L | 71G4 | HindIII: 7,005<br>XbaI: 9.639 |
| M | KB42A33-8, KB71A72-1, KB71A133-11 | HindIII: 3,721<br>XbaI: 3,274 |
| N | KB71A134-2 | HindIII: 7,523<br>XbaI: 10,360; 3,490 |
| O | KB69A125-3, KB69A127-7, KB69A136-2, KB71A20-4 | HindIII: 6,360; 3,726; 1,874; 1,098<br>XbaI: 6,360; 5,893; 5,058; 3,726 |

RFLP data using Probe 177C8-WAR (SEQ ID NO. 51) were as follows:

TABLE 6

| RFLP Class | Strain Name(s) | RFLP Data (approximate band size in base pairs) |
|---|---|---|
| A | 177C8, 74H3 | HindIII: 3,659, 2,454, 606<br>XbaI: 5,457, 4,469, 1,440, 966 |
| B | 177I8, 66D3 | data unavailable |
| C | 28M, 31F2, 71G5, 71G7, 71I1, 71N1, 146F, 185Y2, 201JJ7, KB73, KB68B46-2, KB71A35-4, KB71A116-1 | HindIII: 7,614<br>XbaI: 10,982, 6,235 |
| C₁ | 70B2, 71C2 | HindIII: 8,698, 7,614<br>XbaI: 11,354, 6,235 |
| D | KB68B51-2, KB68B55-2 | HindIII: 7,200<br>XbaI: 6,342 (and 11,225 for 51-2)(and 9,888 for 55-2) |
| E | KB53A49-4 | HindIII: 5,766<br>XbaI: 6,757 |
| F | HD573B, 33F1, 67B3 | HindIII: 3,348, 2,037 (and 6,558 for HDS73B only)<br>XbaI: 6,953 (and 7,815, 6,185 for HD573B only) |

TABLE 6-continued

| RFLP Class | Strain Name(s) | RFLP Data (approximate band size in base pairs) |
|---|---|---|
| G | 205C, 40C1 | HindIII: 3,158<br>XbaI: 6,558, 2,809 |
| H | 130A3, 143A2, 157C1 | HindIII: 4,339, 3,361, 1,954, 660, 349<br>XbaI: 9.043, 4,203, 3,583, 2,958, 581, 464 |
| I | 201Z | HindIII: 4,480, 3,819, 703<br>XbaI: 9,336, 3,256, 495 |
| I | 71G4 | HindIII: 7,005<br>XbaI: 9,639 |
| K | KB42A33-8, K1B71A72-1, KB71A133-11 | no hybridization signal |
| L | KB71A134-2 | HindIII: 7,523<br>XbaI: 10,360 |
| M | KB69A125-3, KB69A127-7, KB69A136-2, KB71A20-4 | HindIII: 5,058; 3,726; 3,198; 2,745; 257<br>XbaI: 5,255; 4,341; 3,452; 1,490; 474 |

EXAMPLE 10
Use of Additional PCR Primers for Characterizing and/or Identifying Novel Genes Another set of PCR primers can be used to identify additional novel genes encoding pesticidal toxins. The sequences of these primers were as follows:

```
ICON-forward:
CTTGAYTTTAAARATGATRTA (SEQ ID NO. 49)

ICON-reverse:
AATRGCSWATAAATAMGCACC (SEQ ID NO. 50)
```

These primers can be used in PCR procedures to amplify a fragment having a predicted size of about 450 bp.

Strains PS177C8, PS177I8, and PS66D3 were screened and were found to have genes amplifiable with these ICON primers. A sequence of a toxin gene from PS177C8 is shown in SEQ ID NO. 51. An amino acid sequence of the 177C8-ICON toxin is shown in SEQ ID NO. 52.

EXAMPLE 11
Use of Mixed Primer Pairs to Characterize and/or Identify Toxin Genes Various combinations of the primers described herein can be used to identify and/or characterize toxin genes. PCR conditions can be used as indicated below:

| | SEQ ID NO. 16/17 | SEQ ID NO. 49/50 | SEQ. ID NO. 49/17 |
|---|---|---|---|
| Pre-denature | 94° C. 1 min. | 94° C. 1 min. | 94° C. 1 min. |
| Program | 94° C. 1 min. | 94° C. 1 min. | 94° C. 1 min. |
| Cycle | 42° C. 2 min. | 42° C. 2 min. | 42° C. 2 min. |
| | 72° C. 3 min. + 5 sec/cycl | 72° C. 3 min. + 5 sec/cycl | 72° C. 3 min. + 5 sec/cycl |
| | Repeat cycle | Repeat cycle | Repeat cycle |
| times | 29 times | 29 times | |
| | Hold 4° C. | Hold 4° C. | Hold 4° C. |

Using the above protocol, a strain harboring a MIS-type of toxin would be expected to yield a 1000 bp fragment with the SEQ ID NO. 16/17 primer pair. A strain harboring a WAR-type of toxin would be expected to amplify a fragment of about 475 bp with the SEQ ID NO. 49/50 primer pair, or a fragment of about 1800 bp with the SEQ ID NO. 49/17 primer pair. The amplified fragments of the expected size were found in four strains. The results are reported in Table 7.

TABLE 7

Approximate Amplified Fragment Sizes (bp)

| Strain | SEQ ID NO. 16/17 | SEQ ID NO. 49/50 | SEQ ID NO. 49/17 |
|---|---|---|---|
| PS66D3 | 1000 | 900, 475 | 1800 |
| PS177C8 | 1000 | 475 | 1800 |
| PS177I8 | 1000 | 900, 550, 475 | 1800 |
| PS217U2 | 1000 | 2500, 1500, 900, 475 | no band detected |

EXAMPLE 12

Characterization and/or Identification of WAR Toxins

In a further embodiment of the subject invention, pesticidal toxins can be characterized and/or identified by their level of reactivity with antibodies to pesticidal toxins exemplified herein. In a specific embodiment, antibodies can be raised to WAR toxins such as the toxin obtainable from PS177C8a. Other WAR toxins can then be identified and/or characterized by their reactivity with the antibodies. In a preferred embodiment, the antibodies are polyclonal antibodies. In this example, toxins with the greatest similarity to the 177C8a-WAR toxin would have the greatest reactivity with the polyclonal antibodies. WAR toxins with greater diversity react with the 177C8a polyclonal antibodies, but to a lesser extent. Toxins which immunoreact with polyclonal antibodies raised to the 177C8a WAR toxin can be obtained from, for example, the isolates designated PS177C8a, PS177I8, PS66D3, KB68B55-2, PS185Y2, PS146F, KB53A49-4, PS175I4, KB68B51-2, PS28K1, PS31F2, KB58B46-2, PS146D, PS74H3, PS28M, PS71G6, PS71G7, PS71I1, PS71N1, PS201JJ7, KB73, KB68B46-2, KB71A35-4, KB71A116-1, PS70B2, PS71C2, PS86D1, HD573B, PS33F1, PS67B3, PS205C, PS40C1, PS130A3, PS143A2, PS157C1, PS201Z, PS71G4, KB42A33-8, KB71A72-1, KB71A133-11, KB71A134-2, KB69A125-3, KB69A127-7, KB69A136-2, and KB71A20-4. Such diverse WAR toxins can be further characterized by, for example, whether or not their genes can be amplified with ICON primers. For example, the following isolates do not have polynucleotide sequences which are amplified by ICON primers: PS177C8a, PS177I8, PS66D3, KB68B55-2, PS185Y2, PS146F, KB53A49-4, PS175I4, KB68B51-2, PS28K1, PS31F2, KB58B46-2, and PS146D. Of these, isolates PS28K1, PS31F2, KB68B46-2, and PS146D show the weakest antibody reactivity, suggesting advantageous diversity.

EXAMPLE 13

Bioassays for Activity Against Lepidopterans and Coleopterans

Biological activity of the toxins and isolates of the subject invention can be confirmed using standard bioassay procedures. One such assay is the budworm-bollworm (*Heliothis virescens* [Fabricius] and *Helicoverpa zea* [Boddie]) assay. Lepidoptera bioassays were conducted with either surface application to artificial insect diet or diet incorporation of samples. All Lepidopteran insects were tested from the neonate stage to the second instar. All assays were conducted with either toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no B. t. serves as the control. First instar larvae (USDA-ARS, Stoneville, Miss.) are placed onto the diet mixture. Wells are then sealed with sheeting (MYLAR; ClearLam Packaging, IL) using a tacking iron, and several pinholes are made in each well to provide gas exchange. Larvae were held at 25° C. for 6 days in a 14:10 (light:dark) holding room. Mortality and stunting are recorded after six days.

Bioassay by the top load method utilizes the same sample and diet preparations as listed above. The samples are applied to the surface of the insect diet. In a specific embodiment, surface area ranged from 0.3 to approximately 0.8 $cm^2$ depending on the tray size, 96 well tissue culture plates were used in addition to the format listed above. Following application, samples are allowed to air dry before insect infestation. A water blank containing no B. t. can serve as the control. Eggs are applied to each treated well and were then sealed with sheeting (MYLAR; ClearLam Packaging, IL) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of sample onto an agar-based artificial diet at a rate of 160 ml/$cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25 ° C., and mortality scored after four days.

Analogous bioassays can be performed by those skilled in the art to assess activity against other pests, such as the black cutworm (*Agrotis ipsilon*).

Results are shown in Table 8.

TABLE 8

Genetics and function of concentrated B.t. supernatants screened for lepidopteran and coleopteran activity

| Strain | Approx. 339 bp PCR fragment | Total Protein ($\mu g/cm^2$) | ca. 80–100 kDa protein ($\mu g/cm^2$) | H. virescens % mortality | Stunting | H. Zen % mortality | Stunting | Diabrotica % mortality |
|---|---|---|---|---|---|---|---|---|
| PS31G1 | + | 8.3 | 2.1 | 70 | yes | 39 | yes | NT |
| PS49C | + | 13.6 | 1.5 | 8 | yes | 8 | no | NT |
| PS80JJ1 | — | 8.0 | NT | 18 | no | 13 | no | NT |
| PS80JJ1 (#2) | — | 35 | NT | — | — | — | — | 43 |

TABLE 8-continued

Genetics and function of concentrated B.t. supernatants screened for lepidopteran and coleopteran activity

| Strain | Approx. 339 bp PCR fragment | Total Protein ($\mu$g/cm$^2$) | ca. 80–100 kDa protein ($\mu$g/cm$^2$) | H. virescens % mortality | Stunting | H. Zen % mortality | Stunting | Diabrotica % mortality |
|---|---|---|---|---|---|---|---|---|
| PS81A2 (#1) | + | 30.3 | 2.3 | 100 | yes | 38 | yes | NT |
| PS81A2 (#2) | + | 18.8 | 1.6 | 38 | yes | 13 | no | NT |
| PS81F | ++ | 26 | 5.2 | 100 | yes | 92 | yes | NT |
| PS81I | + | 10.7 | 1.7 | 48 | yes | 13 | no | NT |
| PS86B1 (#1) | — | 23.2 | 4.5 | 17 | no | 13 | no | — |
| PS86B1 (#2) | — | 90 | 17.5 | — | — | — | — | 35 |
| PS86B1 (#3) | — | 35 | 6.8 | — | — | — | — | 10 |
| PS122D3 (#1) | — | 33.2 | 1.8 | 21 | no | 21 | no | — |
| PS122D3 (#2) | — | 124 | 6.7 | — | — | — | — | 45 |
| PS122D3 (#3) | — | 35 | 1.9 | — | — | — | — | 16 |
| PS123D1 (#1) | — | 10.7 | NT | 0 | no | 0 | no | — |
| PS123D1 (#2) | — | 69 | NT | — | — | — | — | 54 |
| PS123D1 (#3) | — | 35 | NT | — | — | — | — | 21 |
| PS123D1 (#4) | — | 17.8 | NT | 5 | no | 4 | no | NT |
| PS149B1 (#1) | NT | 9 | NT | 0 | no | 0 | yes | NT |
| PS149B1 (#2) | NT | 35 | NT | — | — | — | — | 50 |
| PS157C1 (#1) | — | 24 | 2 | 43 | yes | 13 | yes | — |
| PS157C1 (#2) | — | 93 | 8 | — | — | — | — | 40 |
| PS157C1 (#3) | — | 35 | 3 | — | — | — | — | 18 |
| PS185L2 (#1) | — | 2 | NT | 8 | no | 0 | no | NT |
| PS185L2 (#2) | — | 3 | NT | 10 | no | 25 | no | NT |
| PS185U2 | + | 23.4 | 2.9 | 100 | yes | 100 | yes | NT |
| PS192M4 | + | 10.7 | 2.0 | 9 | no | 4 | yes | NT |
| HD129 | + | 44.4 | 4.9 | 100 | yes | 50 | yes | NT |
| Javelin 1990 | ++ | 43.2 | 3.6 | 100 | yes | 96 | yes | NT |
| water | | | | 0–8 | — | 0–4 | — | 12 |

*NT = not tested

EXAMPLE 14

Results of Western Corn Rootworm Bioassays and Further Characterization of the Toxins Concentrated liquid supernatant solutions, obtained according to the subject invention, were tested for activity against Western corn rootworm (WCRW). Supernatants from the following isolates were found to cause mortality against WCRW: PS10E1, PS31F2, PS31J2, PS33D2, PS66D3, PS68F, PS80JJ1, PS146D, PS175I4, PS177I8, PS196J4, PS197T1, PS197U2, KB33, KB53A49-4, KB68B46-2, KB68B51-2, KB68B55-2, PS177C8, PS69AA2, KB38, PS196F3, PS168G1, PS202E1, PS217U2 and PS185AA2.

Supernatants from the following isolates were also found to cause mortality against WCRW: PS205A3, PS185V2, PS234E1, PS71G4, PS248N10, PS191A21, KB63B19-13, KB63B19-7, KB68B62-7, KB68B63-2, KB69A125-1, KB69A125-3, KB69A125-5, KB69A127-7, KB69A132-1, KB69B2-1, KB70B5-3, KB71A125-15, and KB71A35-6; it was confirmed that this activity was heat labile. Furthermore, it was determined that the supernatants of the following isolates did not react (yielded negative test results) with the WAR antibody (see Example 12), and did not react with the MIS (SEQ ID NO. 31) and WAR (SEQ ID NO. 51) probes: PS205A3, PS185V2, PS234E1, PS71G4, PS248N10, PS191A21, KB63B19-13, KB63B19-7, KB68B62-7, KB68B63-2, KB69A125-1, KB69A125-5, KB69A132-1, KB69B2-1, KB70B5-3, KB71A125-15, and KB71A35-6; the supernatants of isolates KB69A125-3 and KB69A127-7 yielded positive test results.

EXAMPLE 15

Results of Budworm/Bollworm Bioassays

Concentrated liquid supernatant solutions, obtained according to the subject invention, were tested for activity against *Heliothis virescens* (H.v.) and *Helicoverpa zea* (H.z.). Supernatants from the following isolates were tested and were found to cause mortality against H.v.: PS157C1, PS31G1, PS49C, PS81F, PS81I, Javelin 1990, PS158C2, PS202S, PS36A, HD110, and HD29. Supernatants from the following isolates were tested are were found to cause significant mortality against H.z.: PS31G1, PS49C, PS81F, PS81I, PS157C1, PS158C2, PS36A, HD110, and Javelin 1990.

EXAMPLE 16

Target Pests

Toxins of the subject invention can be used, alone or in combination with other toxins, to control one or more non-mammalian pests. These pests may be, for example, those listed in Table 9. Activity can readily be confirmed using the bioassays provided herein, adaptations of these bioassays, and/or other bioassays well known to those skilled in the art.

TABLE 9

Target pest species

| ORDER/Common Name | Latin Name |
|---|---|
| LEPIDOPTERA | |
| European Corn Borer | *Ostrinia nubilalis* |
| European Corn Borer resistant to Cry1 A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |

TABLE 9-continued

Target pest species

| ORDER/Common Name | Latin Name |
|---|---|
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm | *Mamestra configurata* |
| Diamondback Moth | *Plutella xylostells* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 17

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1-46; and An et al. (1985) *EMBO J.* 4:277-287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181-187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic Bacillus genes for use in plants are known in the art.

It should be understood that the examples and embodiments described herein are for illustrative purposes only and that various modifications or changes in light thereof will be suggested to persons skilled in the art and are to be included within the spirit and purview of this application.

What is claimed is:

1. An isolated protein that is toxic to a lepidopteran pest wherein said protein is obtainable from *Bacillus thuringiensis* isolate PS49C (NIRRL B-21532) wherein said isolate comprises a gene that encodes said protein, and said gene hybridizes with the polynucleotide of SEQ ID NO:12 when said polynucleotide is used as a probe under conditions of 0.1% SDS and 1×SSPE at 65°C.

2. A method for controlling a lepidopteran pest wherein said method comprises administering to said pest a protein according to claim 1.

* * * * *

UNITED STATES PATENT AND TRADEMARK OFFICE
CERTIFICATE OF CORRECTION

PATENT NO. : 6,656,908 B2
DATED : December 2, 2003
INVENTOR(S) : Jerald S. Feitelson, Ph.D. et al.

It is certified that error appears in the above-identified patent and that said Letters Patent is hereby corrected as shown below:

Column 18,
Line 59, "Theological" should read -- rheological --.

Column 26,
Line 6, "AAATTATGCGTAAGTCTGC" should read
-- AAATTATGCGCTAAGTCTGC --.

Column 28,
Line 13, "BgIII" should read -- Bg1II --.

Column 29,
Table 6, line 64, for HDS73B only" should read -- for HD573B only --.

Column 30,
Line 13, table 6, "I  71G4" should read -- J  71G4 --.
Line 14, table 6, "K1B71A72-1" should read -- KB71A72-1 --.
Lines 56-57, "Repeat cycle" should read -- Repeat cycle 29 times --.

Column 167,
Line 4, "NIRRL" should read -- NRRL --.

Signed and Sealed this

Fourteenth Day of September, 2004

JON W. DUDAS
*Director of the United States Patent and Trademark Office*

SEQUENCE LISTING (1) GENERAL INFORMATION:

(iii) NUMBER OF SEQUENCES: 144

(2) INFORMATION FOR SEQ ID NO: 1:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

GARCCRTGGA AAGCAAATAA TAARAATGC                                          29

(2) INFORMATION FOR SEQ ID NO: 2:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 2:

AAARTTATCT CCCCAWGCTT CATCTCCATT TTG                                     33

(2) INFORMATION FOR SEQ ID NO: 3:

(i) SEQUENCE CHARACTERISTICS:
       (A) LENGTH: 2375 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (C) INDIVIDUAL ISOLATE: 36a (xi) SEQUENCE DESCRIPTION: SEQ ID NO: 3:

ATGAACAAGA ATAATACTAA ATTAAGCACA AGAGCCTTAC CAAGTTTTAT TGATTATTTT60

AATGGCATTT ATGGATTTGC CACTGGTATC AAAGACATTA TGAACATGAT TTTTAAAAC120

GATACAGGTG GTGATCTAAC CCTAGACGAA ATTTTAAAGA ATCAGCAGTT ACTAAATGA180

ATTTCTGGTA AATTGGATGG GGTGAATGGA AGCTTAAATG ATCTTATCGC ACAGGGAAA240

TTAAATACAG AATTATCTAA GGAAATATTA AAAATTGCAA ATGAACAAAA TCAAGTTTT300

AATGATGTTA ATAACAAACT CGATGCGATA AATACGATGC TTCGGGTATA TCTACCTAA360

ATTACCTCTA TGTTGAGTGA TGTAATGAAA CAAAATTATG CGCTAAGTCT GCAAATAGA420

TACTTAAGTA AACAATTGCA AGAGATTTCT GATAAGTTGG ATATTATTAA TGTAAATGT480

CTTATTAACT CTACACTTAC TGAAATTACA CCTGCGTATC AAAGGATTAA ATATGTGAA540

GAAAAATTTG AGGAATTAAC TTTTGCTACA GAAACTAGTT CAAAAGTAAA AAAGGATGG600

TCTCCTGCAA ATATTCTTGA TGAGTTAACT GAGTTAACTG AACTAGCGAA AAGTGTAAC660

AAAAATGATG TGGATGGTTT TGAATTTTAC CTTAATACAT TCCACGATGT AATGGTAGG720

AATAATTTAT TCGGGCGTTC AGCTTTAAAA ACTGCATCGG AATTAATTAC TAAAGAAAA780

```
GTGAAAACAA GTGGCAGTGA GGTCGGAAAT GTTTATAACT TCTTAATTGT ATTAACAGC  840

CTGCAAGCAA AAGCTTTTCT TACTTTAACA ACATGCCGAA AATTATTAGG CTTAGCAGA  900

ATTGATTATA CTTCTATTAT GAATGAACAT TTAAATAAGG AAAAGAGGA ATTTAGAGT  960

AACATCCTCC CTACACTTTC TAATACTTTT TCTAATCCTA ATTATGCAAA AGTTAAAG 1020

AGTGATGAAG ATGCAAAGAT GATTGTGGAA GCTAAACCAG ACATGCATT GATTGGGT 1080

GAAATTAGTA ATGATTCAAT TACAGTATTA AAAGTATATG AGGCTAAGCT AAAACAAA 1140

TATCAAGTCG ATAAGGATTC CTTATCGGAA GTTATTTATG GTGATATGGA TAAATTAT 1200

TGCCCAGATC AATCTGAACA AATCTATTAT ACAAATAACA TAGTATTTCC AAATGAAT 1260

GTAATTACTA AAATTGATTT CACTAAAAAA ATGAAAACTT AAGATATGA GGTAACAG 1320

AATTTTTATG ATTCTTCTAC AGGAGAAATT GACTTAAATA AGAAAAAGT AGAATCAA 1380

GAAGCGGAGT ATAAAACGTT AAGTGCTAAT GATGATGGGG TGTATATGCC GTTAGGTG 1440

ATCAGTGAAA CATTTTTGAC TCCGATTAAT GGGTTTGGCC TCCAAGCTGA TGAAAATT 1500

AGATTAATTA CTTTAACATG TAAATCATAT TTAAGAGAAC TACTGCTAGC AACAGACT 1560

AGCAATAAAG AAACTAAATT GATCGTCCCG CCAAGTGGTT TTATTAGCAA TATTGTAG 1620

AACGGGTCCA TAGAAGAGGA CAATTTAGAG CCGTGGAAAG CAAATAATAA GAATGCGT 1680

GTAGATCATA CAGGCGGAGT GAATGGAACT AAAGCTTTAT ATGTTCATAA GGACGGAG 1740

ATTTCACAAT TTATTGGAGA TAATTTAAAA CCGAAAACTG AGTATGTAAT CCAATATA 1800

GTTAAAGGAA AACCTTCTAT TCATTTAATA GATGAAAATA CTGGATATAT TCATTATG 1860

GATACAAATA ATAATTTAGA AGATTATCAA ACTATTAATA AACGTTTTAC TACAGGAA 1920

GATTTAAAGG GAGTGTATTT AATTTTAAAA AGTCAAAATG GAGATGAAGC TTGGGGAG 1980

AACTTTATTA TTTTGGAAAT TAGTCCTTCT GAAAAGTTAT TAAGTCCAGA ATTAATTA 2040

ACAAATAATT GGACGAGTAC GGGATCAACT AATATTAGCG GTAATACACT CACTCTTT 2100

CAGGGAGGAC GAGGGATTCT AAAACAAAAC CTTCAATTAG ATAGTTTTTC AACTTATA 2160

GTGTATTTTT CTGTGTCCGG AGATGCTAAT GTAAGGATTA GAAATTCTAG GGAAGTGT 2220

TTTGAAAAAA GATATATGAG CGGTGCTAAA GATGTTTCTG AAATGTTCAC TACAAAAT 2280

GAGAAAGATA ACTTTTATAT AGAGCTTTCT CAAGGGAATA ATTTATATGG TGGTCCTA 2340

GTACATTTTT ACGATGTCTC TATTAAGTAA CCCAA                          2375
```

(2) INFORMATION FOR SEQ ID NO: 4:

(i) SEQUENCE CHARACTERISTICS:
        (A) LENGTH: 790 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: 36a (xi) SEQUENCE DESCRIPTION: SEQ ID NO: 4:

```
Met Asn Lys Asn Asn Thr Lys Leu Ser Thr Arg Ala Leu Pro Ph
 1               5                  10                  15

Ile Asp Tyr Phe Asn Gly Ile Tyr Gly Phe Ala Thr Gly Ile Lys As
                  20                  25                  30

Ile Met Asn Met Ile Phe Lys Thr Asp Thr Gly Gly Asp Leu Thr Le
                      35                  40                  45
```

```
Asp Glu Ile Leu Lys Asn Gln Gln Leu Leu Asn Asp Ile Ser Gly Ly
     50                  55                  60

Leu Asp Gly Val Asn Gly Ser Leu Asn Asp Leu Ile Ala Gln Gly As
 65                  70                  75                  80

Leu Asn Thr Glu Leu Ser Lys Glu Ile Leu Lys Ile Ala Asn Glu Gl
                 85                  90                  95

Asn Gln Val Leu Asn Asp Val Asn Lys Leu Asp Ala Ile Asn Th
                100                 105                 110

Met Leu Arg Val Tyr Leu Pro Lys Ile Thr Ser Met Leu Ser Asp Va
            115                 120                 125

Met Lys Gln Asn Tyr Ala Leu Ser Leu Gln Ile Glu Tyr Leu Ser Ly
        130                 135                 140

Gln Leu Gln Glu Ile Ser Asp Lys Leu Asp Ile Ile Asn Val Asn Va
145                 150                 155                 160

Leu Ile Asn Ser Thr Leu Thr Glu Ile Thr Pro Ala Tyr Gln Arg Il
                165                 170                 175

Lys Tyr Val Asn Glu Lys Phe Glu Leu Thr Phe Ala Thr Glu Th
            180                 185                 190

Ser Ser Lys Val Lys Lys Asp Gly Ser Pro Ala Asn Ile Leu Asp Gl
        195                 200                 205

Leu Thr Glu Leu Thr Glu Leu Ala Lys Ser Val Thr Lys Asn Asp Va
    210                 215                 220

Asp Gly Phe Glu Phe Tyr Leu Asn Thr Phe His Asp Val Met Val Gl
225                 230                 235                 240

Asn Asn Leu Phe Gly Arg Ser Ala Leu Lys Thr Ala Ser Glu Leu Il
                245                 250                 255

Thr Lys Glu Asn Val Lys Thr Ser Gly Ser Glu Val Gly Asn Val Ty
            260                 265                 270

Asn Phe Leu Ile Val Leu Thr Ala Leu Gln Ala Lys Ala Phe Leu Th
        275                 280                 285

Leu Thr Thr Cys Arg Lys Leu Leu Gly Leu Ala Asp Ile Asp Tyr Th
    290                 295                 300

Ser Ile Met Asn Glu His Leu Asn Lys Glu Lys Glu Phe Arg Va
305                 310                 315                 320

Asn Ile Leu Pro Thr Leu Ser Asn Thr Phe Ser Asn Pro Asn Tyr Al
                325                 330                 335

Lys Val Lys Gly Ser Asp Glu Asp Ala Lys Met Ile Val Glu Ala Ly
            340                 345                 350

Pro Gly His Ala Leu Ile Gly Phe Glu Ile Ser Asn Asp Ser Ile Th
        355                 360                 365

Val Leu Lys Val Tyr Glu Ala Lys Leu Lys Gln Asn Tyr Gln Val As
    370                 375                 380

Lys Asp Ser Leu Ser Glu Val Ile Tyr Gly Asp Met Asp Lys Leu Le
385                 390                 395                 400

Cys Pro Asp Gln Ser Glu Gln Ile Tyr Tyr Thr Asn Asn Ile Val Ph
                405                 410                 415

Pro Asn Glu Tyr Val Ile Thr Lys Ile Asp Phe Thr Lys Lys Met Ly
            420                 425                 430

Thr Leu Arg Tyr Glu Val Thr Ala Asn Phe Tyr Asp Ser Ser Thr Gl
        435                 440                 445

Glu Ile Asp Leu Asn Lys Lys Val Glu Ser Ser Glu Ala Glu Ty
    450                 455                 460

Lys Thr Leu Ser Ala Asn Asp Asp Gly Val Tyr Met Pro Leu Gly Va
```

```
                465            470             475              480
        Ile Ser Glu Thr Phe Leu Thr Pro Ile Asn Gly Phe Gly Leu Gln Al
                            485             490             495

Asp Glu Asn Ser Arg Leu Ile Thr Leu Thr Cys Lys Ser Tyr Leu Ar
                        500             505             510

Glu Leu Leu Leu Ala Thr Asp Leu Ser Asn Lys Glu Thr Lys Leu Il
                    515             520             525

Val Pro Pro Ser Gly Phe Ile Ser Asn Ile Val Glu Asn Gly Ser Il
                530             535             540

Glu Glu Asp Asn Leu Glu Pro Trp Lys Ala Asn Asn Lys Asn Ala Ty
        545             550             555             560

Val Asp His Thr Gly Gly Val Asn Gly Thr Lys Ala Leu Tyr Val Hi
                        565             570             575

Lys Asp Gly Gly Ile Ser Gln Phe Ile Gly Asp Asn Leu Lys Pro Ly
                    580             585             590

Thr Glu Tyr Val Ile Gln Tyr Thr Val Lys Gly Lys Pro Ser Ile Hi
                595             600             605

Leu Ile Asp Glu Asn Thr Gly Tyr Ile His Tyr Glu Asp Thr Asn As
            610             615             620

Asn Leu Glu Asp Tyr Gln Thr Ile Asn Lys Arg Phe Thr Thr Gly Th
        625             630             635             640

Asp Leu Lys Gly Val Tyr Leu Ile Leu Lys Ser Gln Asn Gly Asp Gl
                        645             650             655

Ala Trp Gly Asp Asn Phe Ile Ile Leu Glu Ile Ser Pro Ser Glu Ly
                    660             665             670

Leu Leu Ser Pro Glu Leu Ile Asn Thr Asn Asn Trp Thr Ser Thr Gl
                675             680             685

Ser Thr Asn Ile Ser Gly Asn Thr Leu Thr Leu Tyr Gln Gly Gly Ar
            690             695             700

Gly Ile Leu Lys Gln Asn Leu Gln Leu Asp Ser Phe Ser Thr Tyr Ar
        705             710             715             720

Val Tyr Phe Ser Val Ser Gly Asp Ala Asn Val Arg Ile Arg Asn Se
                        725             730             735

Arg Glu Val Leu Phe Glu Lys Arg Tyr Met Ser Gly Ala Lys Asp Va
                    740             745             750

Ser Glu Met Phe Thr Thr Lys Phe Glu Lys Asp Asn Phe Tyr Ile Gl
                755             760             765

Leu Ser Gln Gly Asn Asn Leu Tyr Gly Gly Pro Ile Val His Phe Ty
        770             775             780

Asp Val Ser Ile Lys Pro
        785             790
```

(2) INFORMATION FOR SEQ ID NO: 5:

(i) SEQUENCE CHARACTERISTICS:
        (A) LENGTH: 2370 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 81F (xi) SEQUENCE DESCRIPTION: SEQ ID NO: 5:

ATGAACAAGA ATAATACTAA ATTAAGCACA AGAGCCTTAC CAAGTTTTAT TGATTATTTT 60

-continued

```
AATGGCATTT ATGGATTTGC CACTGGTATC AAAGACATTA TGAACATGAT TTTTAAAAC  120
GATACAGGTG GTGATCTAAC CCTAGACGAA ATTTTAAAGA ATCAGCAGTT ACTAAATGA  180
ATTTCTGGTA AATTGGATGG GGTGAATGGA AGCTTAAATG ATCTTATCGC ACAGGGAAA  240
TTAAATACAG AATTATCTAA AGAAATATTA AAAATTGCAA ATGAACAAAA TCAAGTTTT  300
AATGATGTTG ATAACAAACT CGATGCGATA AATACGATGC TTCGGGTATA TCTACCTAA  360
ATTACCTCTA TGTTGAGTGA TGTAATGAAA CAAAATTATG CGCTAAGTCT GCAAATAGA  420
TACTTAAGTA AACAATTGCA AGAGATTTCT GATAAGTTGG ATATTATTAA TGTAAATGT  480
CTTATTAACT CTACACTTAC TGAAATTACA CCTGCGTATC AAAGGATTAA ATATGTGAA  540
GAAAAATTTG AGGAATTAAC TTTTGCTACA GAAACTAGTT CAAAAGTAAA AAAGGATGG  600
TCTCCTGCAG ATATTCTTGA TGAGTTAACT GAGTTAACTG AACTAGCGAA AAGTGTAAC  660
AAAAATGATG TGGATGGTTT TGAATTTTAC CTTAATACAT TCCACGATGT AATGGTAGG  720
AATAATTTAT TCGGGCGTTC AGCTTTAAAA ACTGCATCGG AATTAATTAC TAAAGAAAA  780
GTGAAAACAA GTGGCAGTGA GGTCGGAAAT GTTTATAACT TCTTAATTGT ATTAACAGC  840
CTGCAAGCAA AAGCTTTTCT TACTTTAACA ACATGCCGAA AATTATTAGG CTTAGCAGA  900
ATTGATTATA CTTCTATTAT GAATGAACAT TTAAATAAGG AAAAGAGGA ATTTAGAGT  960
AACATCCTCC CTACACTTTC TAATACTTTT TCTAATCCTA ATTATGCAAA AGTTAAAG  1020
AGTGATGAAG ATGCAAAGAT GATTGTGGAA GCTAAACCAG GACATGCATT GGTTGGGT  1080
GAAATTAGTA ATGATTCAAT TACAGTATTA AAAGTATATG AGGCTAAGCT AAAACAAA  1140
TATCAAGTTG ATAAGGATTC CTTATCGGAA GTTATTTATG GTGATATGGA TAAATTAT  1200
TGCCCAGATC AATCTGAACA AATCTATTAT ACAAATAACA TAGTATTTCC AAATGAAT  1260
GTAATTACTA AAATTGATTT TACTAAAAAA ATGAAAACTT TAAGATATGA GGTAACAG  1320
AATTTTTATG ATTCTTCTAC AGGAGAAATT GACTTAAATA AGAAAAAGT AGAATCAA  1380
GAAGCGGAGT ATAGAACGTT AAGTGCTAAT GATGATGGAG TGTATATGCC GTTAGGTG  1440
ATCAGTGAAA CATTTTTGAC TCCGATTAAT GGGTTTGGCC TCCAAGCTGA TGAAAATT  1500
AGATTAATTA CTTTAACATG TAAATCATAT TTAAGAGAAC TACTGCTAGC AACAGACT  1560
AGCAATAAAG AAACTAAATT GATCGTCCCG CCCAGTGGTT TTATTAAAAA TATTGTAG  1620
AACGGGTCCA TAGAAGAGGA CAATTTAGAG CCGTGGAAAG CAAATAATAA GAATGAGT  1680
GTAGATCATA CAGGCGGAGT GAATGGGACT AAAGCTTTAT ATGTTCATAA GGACGGAG  1740
ATTTCACAAT TTATTGGAGA TAAGTTAAAA CCGAAAACTG AGTATGTAAT CCAATATA  1800
GTTAAAGGAA AACCTTCTAT TCATTTAAAA GATGAAAATA CTGGATATAT TCATTATG  1860
GATACAAATA ATAATTTAGA AGATTATCAA ACTATTACTA AACGTTTTAC TACAGGAA  1920
GATTTAAAGG GAGTGTATTT AATTTTAAAA AGTCAAAATG GAGATGAAGC TTGGGGAG  1980
AACTTTATTA TTTTGGAAAT TAGTCCTTCT GAAAAGTTAT TAAGTCCAGA ATTAATTA  2040
ACAAATAATT GGACGAGTAC GGGATCAACT AATATTAGCG GTAATACACT CACTCTTT  2100
CAGGGAGGAC GAGGAATTCT AAAACAAAAC CTTCAATTAG ATAGTTTTTC AACTTATA  2160
GTGTATTTTT CTGTGTCCGG AGATGCTAAT GTAAGGATTA GAAATTCTAG GAAGTGT  2220
TTTGAAAAAA GATATATGAG CGGTGCTAAA GATGTTTCTG AAATTTTCAC TACAAAAT  2280
GGGAAAGATA ACTTTTATAT AGAGCTTTCT CAAGGGAATA ATTTAAATGG TGGCCCTA  2340
GTACAGTTTC CGATGTCTC TATTAAGTAA                                  2370
```

(2) INFORMATION FOR SEQ ID NO: 6:

(i) SEQUENCE CHARACTERISTICS:
      (A) LENGTH: 789 amino acids
      (B) TYPE: amino acid
      (C) STRANDEDNESS: single
      (D) TOPOLOGY: linear (ii) MOLECULE TYPE: protein (vi) ORIGINAL SOURCE:
      (C) INDIVIDUAL ISOLATE: 81F (xi) SEQUENCE DESCRIPTION: SEQ ID NO: 6:

```
Met Asn Lys Asn Asn Thr Lys Leu Ser Thr Arg Ala Leu Pro Ser Ph
  1               5                  10                  15

Ile Asp Tyr Phe Asn Gly Ile Tyr Gly Phe Ala Thr Gly Ile Lys As
             20                  25                  30

Ile Met Asn Met Ile Phe Lys Thr Asp Thr Gly Gly Asp Leu Thr Le
         35                  40                  45

Asp Glu Ile Leu Lys Asn Gln Gln Leu Leu Asn Asp Ile Ser Gly Ly
     50                  55                  60

Leu Asp Gly Val Asn Gly Ser Leu Asn Asp Leu Ile Ala Gln Gly As
 65                  70                  75                  80

Leu Asn Thr Glu Leu Ser Lys Glu Ile Leu Lys Ile Ala Asn Glu Gl
                 85                  90                  95

Asn Gln Val Leu Asn Asp Val Asp Asn Lys Leu Asp Ala Ile Asn Th
             100                 105                 110

Met Leu Arg Val Tyr Leu Pro Lys Ile Thr Ser Met Leu Ser Asp Va
         115                 120                 125

Met Lys Gln Asn Tyr Ala Leu Ser Leu Gln Ile Glu Tyr Leu Ser Ly
     130                 135                 140

Gln Leu Gln Glu Ile Ser Asp Lys Leu Asp Ile Ile Asn Val Asn Va
145                 150                 155                 160

Leu Ile Asn Ser Thr Leu Thr Glu Ile Thr Pro Ala Tyr Gln Arg Il
                 165                 170                 175

Lys Tyr Val Asn Glu Lys Phe Glu Glu Leu Thr Phe Ala Thr Glu Th
             180                 185                 190

Ser Ser Lys Val Lys Lys Asp Gly Ser Pro Ala Asp Ile Leu Asp Gl
         195                 200                 205

Leu Thr Glu Leu Thr Glu Leu Ala Lys Ser Val Thr Lys Asn Asp Va
     210                 215                 220

Asp Gly Phe Glu Phe Tyr Leu Asn Thr Phe His Asp Val Met Val Gl
225                 230                 235                 240

Asn Asn Leu Phe Gly Arg Ser Ala Leu Lys Thr Ala Ser Glu Leu Il
                 245                 250                 255

Thr Lys Glu Asn Val Lys Thr Ser Gly Ser Glu Val Gly Asn Val Ty
             260                 265                 270

Asn Phe Leu Ile Val Leu Thr Ala Leu Gln Ala Lys Ala Phe Leu Th
         275                 280                 285

Leu Thr Thr Cys Arg Lys Leu Leu Gly Leu Ala Asp Ile Asp Tyr Th
     290                 295                 300

Ser Ile Met Asn Glu His Leu Asn Lys Glu Lys Glu Glu Phe Arg Va
305                 310                 315                 320

Asn Ile Leu Pro Thr Leu Ser Asn Thr Phe Ser Asn Pro Asn Tyr Al
                 325                 330                 335
```

```
Lys Val Lys Gly Ser Asp Glu Asp Ala Lys Met Ile Val Glu Ala Ly
                340                 345                 350
Pro Gly His Ala Leu Val Gly Phe Glu Ile Ser Asn Asp Ser Ile Th
                355                 360                 365
Val Leu Lys Val Tyr Glu Ala Lys Leu Lys Gln Asn Tyr Gln Val As
                370                 375                 380
Lys Asp Ser Leu Ser Glu Val Ile Tyr Gly Asp Met Asp Lys Leu Le
385                 390                 395                 400
Cys Pro Asp Gln Ser Glu Gln Ile Tyr Tyr Thr Asn Asn Ile Val Ph
                405                 410                 415
Pro Asn Glu Tyr Val Ile Thr Lys Ile Asp Phe Thr Lys Lys Met Ly
                420                 425                 430
Thr Leu Arg Tyr Glu Val Thr Ala Asn Phe Tyr Asp Ser Ser Thr Gl
                435                 440                 445
Glu Ile Asp Leu Asn Lys Lys Lys Val Glu Ser Ser Glu Ala Glu Ty
                450                 455                 460
Arg Thr Leu Ser Ala Asn Asp Asp Gly Val Tyr Met Pro Leu Gly Va
465                 470                 475                 480
Ile Ser Glu Thr Phe Leu Thr Pro Ile Asn Gly Phe Gly Leu Gln Al
                485                 490                 495
Asp Glu Asn Ser Arg Leu Ile Thr Leu Thr Cys Lys Ser Tyr Leu Ar
                500                 505                 510
Glu Leu Leu Leu Ala Thr Asp Leu Ser Asn Lys Glu Thr Lys Leu Il
                515                 520                 525
Val Pro Pro Ser Gly Phe Ile Lys Asn Ile Val Glu Asn Gly Ser Il
                530                 535                 540
Glu Glu Asp Asn Leu Glu Pro Trp Lys Ala Asn Asn Lys Asn Glu Ty
545                 550                 555                 560
Val Asp His Thr Gly Gly Val Asn Gly Thr Lys Ala Leu Tyr Val Hi
                565                 570                 575
Lys Asp Gly Gly Ile Ser Gln Phe Ile Gly Asp Lys Leu Lys Pro Ly
                580                 585                 590
Thr Glu Tyr Val Ile Gln Tyr Thr Val Lys Gly Lys Pro Ser Ile Hi
                595                 600                 605
Leu Lys Asp Glu Asn Thr Gly Tyr Ile His Tyr Glu Asp Thr Asn As
                610                 615                 620
Asn Leu Glu Asp Tyr Gln Thr Ile Thr Lys Arg Phe Thr Thr Gly Th
625                 630                 635                 640
Asp Leu Lys Gly Val Tyr Leu Ile Leu Lys Ser Gln Asn Gly Asp Gl
                645                 650                 655
Ala Trp Gly Asp Asn Phe Ile Ile Leu Glu Ile Ser Pro Ser Glu Ly
                660                 665                 670
Leu Leu Ser Pro Glu Leu Ile Asn Thr Asn Asn Trp Thr Ser Thr Gl
                675                 680                 685
Ser Thr Asn Ile Ser Gly Asn Thr Leu Thr Leu Tyr Gln Gly Gly Ar
                690                 695                 700
Gly Ile Leu Lys Gln Asn Leu Gln Leu Asp Ser Phe Ser Thr Tyr Ar
705                 710                 715                 720
Val Tyr Phe Ser Val Ser Gly Asp Ala Asn Val Arg Ile Arg Asn Se
                725                 730                 735
Arg Glu Val Leu Phe Glu Lys Arg Tyr Met Ser Gly Ala Lys Asp Va
                740                 745                 750
Ser Glu Ile Phe Thr Thr Lys Phe Gly Lys Asp Asn Phe Tyr Ile Gl
```

755                 760                    765
           Leu Ser Gln Gly Asn Asn Leu Asn Gly Gly Pro Ile Val Gln Phe Pr
               770                 775                780

Asp Val Ser Ile Lys
           785

(2) INFORMATION FOR SEQ ID NO: 7:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (C) INDIVIDUAL ISOLATE: Jav90

(xi) SEQUENCE DESCRIPTION: SEQ ID NO: 7:

ATGAACAAGA ATAATACTAA ATTAAGCACA AGAGCCTTAC CAAGTTTTAT TGATTATTTT60

AATGGCATTT ATGGATTTGC CACTGGTATC AAAGACATTA TGAACATGAT TTTTAAAAC120

GATACAGGTG GTGATCTAAC CCTAGACGAA ATTTTAAAGA ATCAGCAGTT ACTAAATGA180

ATTTCTGGTA AATTGGATGG GGTGAATGGA AGCTTAAATG ATCTTATCGC ACAGGGAAA240

TTAAATACAG AATTATCTAA GGAAATATTA AAAATTGCAA ATGAACAAAA TCAAGTTTT300

AATGATGTTA ATAACAAACT CGATGCGATA AATACGATGC TTCGGGTATA TCTACCTAA360

ATTACCTCTA TGTTGAGTGA TGTAATGAAA CAAAATTATG CGCTAAGTCT GCAAATAGA420

TACTTAAGTA AACAATTGCA AGAGATTTCT GATAAGTTGG ATATTATTAA TGTAAATGT480

CTTATTAACT CTACACTTAC TGAAATTACA CCTGCGTATC AAAGGATTAA ATATGTGAA540

GAAAAATTTG AGGAATTAAC TTTTGCTACA GAAACTAGTT CAAAAGTAAA AAAGGATGG600

TCTCCTGCAG ATATTCTTGA TGAGTTAACT GAGTTAACTG AACTAGCGAA AAGTGTAAC660

AAAAATGATG TGGATGGTTT TGAATTTTAC CTTAATACAT TCCACGATGT AATGGTAGG720

AATAATTTAT TCGGGCGTTC AGCTTTAAAA ACTGCATCGG AATTAATTAC TAAAGAAAA780

GTGAAAACAA GTGGCAGTGA GGTCGGAAAT GTTTATAACT TCTTAATTGT ATTAACAGC840

CTGCAAGCAA AAGCTTTTCT TACTTTAACA ACATGCCGAA AATTATTAGG CTTAGCAGA900

ATTGATTATA CTTCTATTAT GAATGAACAT TTAAATAAGG AAAAGAGGA ATTTAGAGT960

AACATCCTCC CTACACTTTC TAATACTTTT TCTAATCCTA ATTATGCAAA AGTTAAAG1020

AGTGATGAAG ATGCAAAGAT GATTGTGGAA GCTAAACCAG GACATGCATT GATTGGGT1080

GAAATTAGTA ATGATTCAAT TACAGTATTA AAAGTATATG AGGCTAAGCT AAAACAAA1140

TATCAAGTCG ATAAGGATTC CTTATCGGAA GTTATTTATG GTGATATGGA TAAATTAT1200

TGCCCAGATC AATCTGAACA AATCTATTAT ACAAATAACA TAGTATTTCC AAATGAAT1260

GTAATTACTA AAATTGATTT CACTAAAAAA ATGAAAACTT AAGATATGA GGTAACAG1320

AATTTTTATG ATTCTTCTAC AGGAGAAATT GACTTAAATA AGAAAAAGT AGAATCAA1380

GAAGCGGAGT ATAGAACGTT AAGTGCTAAT GATGATGGGG TGTATATGCC GTTAGGTG1440

ATCAGTGAAA CATTTTTGAC TCCGATTAAT GGGTTTGGCC TCCAAGCTGA TGAAAATT1500

AGATTAATTA CTTTAACATG TAAATCATAT TTAAGAGAAC TACTGCTAGC AACAGACT1560

AGCAATAAAG AAACTAAATT GATYGTCCCG CCAAGTGGTT TTATTAGCAA TATTGTAG1620

AACGGGTCCA TAGAAGAGGA CAATTTAGAG CCGTGGAAAG CAAATAATAA GAATGCGT1680

-continued

```
GTAGATCATA CAGGCGGAGT GAATGGAACT AAAGCTTTAT ATGTTCATAA GGACGGAG 1740

ATTTCACAAT TTATTGGAGA TAAGTTAAAA CCGAAAACTG AGTATGTAAT CCAATATA 1800

GTTAAAGGAA AACCTTCTAT TCATTTAAAA GATGAAAATA CTGGATATAT TCATTATG 1860

GATACAAATA ATAATTTAGA AGATTATCAA ACTATTAATA AACGTTTTAC TACAGGAA 1920

GATTTAAAGG GAGTGTATTT AATTTTAAAA AGTCAAAATG GAGATGAAGC TTGGGGAG 1980

AACTTTATTA TTTTGGAAAT TAGTCCTTCT GAAAAGTTAT TAAGTCCAGA ATTAATTA 2040

ACAAATAATT GGACGAGTAC GGGATCAACT AATATTAGCG GTAATACACT CACTCTTT 2100

CAGGGAGGAC GAGGGATTCT AAAACAAAAC CTTCAATTAG ATAGTTTTTC AACTTATA 2160

GTGTATTTTT CTGTGTCCGG AGATGCTAAT GTAAGGATTA GAAATTCTAG GGAAGTGT 2220

TTTGAAAAAA GATATATGAG CGGTGCTAAA GATGTTTCTG AAATGTTCAC TACAAAAT 2280

GAGAAAGATA ACTTTATAT AGAGCTTTCT CAAGGGAATA ATTTATATGG TGGTCCTA 2340

GTACATTTTT ACGATGTCTC TATTAAGTAA CCCAA                           2375
```

(2) INFORMATION FOR SEQ ID NO: 8:

(i) SEQUENCE CHARACTERISTICS:
        (A) LENGTH: 790 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: Jav90

(xi) SEQUENCE DESCRIPTION: SEQ ID NO: 8:

```
Met Asn Lys Asn Asn Thr Lys Leu Ser Thr Arg Ala Leu Pro Ser Ph
 1               5                  10                  15
Ile Asp Tyr Phe Asn Gly Ile Tyr Gly Phe Ala Thr Gly Ile Lys As
            20                  25                  30
Ile Met Asn Met Ile Phe Lys Thr Asp Thr Gly Gly Asp Leu Thr Le
        35                  40                  45
Asp Glu Ile Leu Lys Asn Gln Gln Leu Leu Asn Asp Ile Ser Gly Ly
    50                  55                  60
Leu Asp Gly Val Asn Gly Ser Leu Asn Asp Leu Ile Ala Gln Gly As
65                  70                  75                  80
Leu Asn Thr Glu Leu Ser Lys Glu Ile Leu Lys Ile Ala Asn Glu Gl
                85                  90                  95
Asn Gln Val Leu Asn Asp Val Asn Asn Lys Leu Asp Ala Ile Asn Th
            100                 105                 110
Met Leu Arg Val Tyr Leu Pro Lys Ile Thr Ser Met Leu Ser Asp Va
        115                 120                 125
Met Lys Gln Asn Tyr Ala Leu Ser Leu Gln Ile Glu Tyr Leu Ser Ly
    130                 135                 140
Gln Leu Gln Glu Ile Ser Asp Lys Leu Asp Ile Ile Asn Val Asn Va
145                 150                 155                 160
Leu Ile Asn Ser Thr Leu Thr Glu Ile Thr Pro Ala Tyr Gln Arg Il
                165                 170                 175
Lys Tyr Val Asn Glu Lys Phe Glu Glu Leu Thr Phe Ala Thr Glu Th
            180                 185                 190
Ser Ser Lys Val Lys Lys Asp Gly Ser Pro Ala Asp Ile Leu Asp Gl
        195                 200                 205
```

-continued

```
Leu Thr Glu Leu Thr Glu Leu Ala Lys Ser Val Thr Lys Asn Asp Va
    210                 215                 220
Asp Gly Phe Glu Phe Tyr Leu Asn Thr Phe His Asp Val Met Val Gl
225                 230                 235                 240
Asn Asn Leu Phe Gly Arg Ser Ala Leu Lys Thr Ala Ser Glu Leu Il
                245                 250                 255
Thr Lys Glu Asn Val Lys Thr Ser Gly Ser Glu Val Gly Asn Val Ty
            260                 265                 270
Asn Phe Leu Ile Val Leu Thr Ala Leu Gln Ala Lys Ala Phe Leu Th
        275                 280                 285
Leu Thr Thr Cys Arg Lys Leu Leu Gly Leu Ala Asp Ile Asp Tyr Th
    290                 295                 300
Ser Ile Met Asn Glu His Leu Asn Lys Glu Lys Glu Phe Arg Va
305                 310                 315                 320
Asn Ile Leu Pro Thr Leu Ser Asn Thr Phe Ser Asn Pro Asn Tyr Al
                325                 330                 335
Lys Val Lys Gly Ser Asp Glu Asp Ala Lys Met Ile Val Glu Ala Ly
            340                 345                 350
Pro Gly His Ala Leu Ile Gly Phe Glu Ile Ser Asn Asp Ser Ile Th
        355                 360                 365
Val Leu Lys Val Tyr Glu Ala Lys Leu Lys Gln Asn Tyr Gln Val As
    370                 375                 380
Lys Asp Ser Leu Ser Glu Val Ile Tyr Gly Asp Met Asp Lys Leu Le
385                 390                 395                 400
Cys Pro Asp Gln Ser Glu Gln Ile Tyr Tyr Thr Asn Asn Ile Val Ph
                405                 410                 415
Pro Asn Glu Tyr Val Ile Thr Lys Ile Asp Phe Thr Lys Lys Met Ly
            420                 425                 430
Thr Leu Arg Tyr Glu Val Thr Ala Asn Phe Tyr Asp Ser Ser Thr Gl
        435                 440                 445
Glu Ile Asp Leu Asn Lys Lys Val Glu Ser Ser Glu Ala Glu Ty
    450                 455                 460
Arg Thr Leu Ser Ala Asn Asp Asp Gly Val Tyr Met Pro Leu Gly Va
465                 470                 475                 480
Ile Ser Glu Thr Phe Leu Thr Pro Ile Asn Gly Phe Gly Leu Gln Al
                485                 490                 495
Asp Glu Asn Ser Arg Leu Ile Thr Leu Thr Cys Lys Ser Tyr Leu Ar
            500                 505                 510
Glu Leu Leu Leu Ala Thr Asp Leu Ser Asn Lys Glu Thr Lys Leu Il
        515                 520                 525
Val Pro Pro Ser Gly Phe Ile Ser Asn Ile Val Glu Asn Gly Ser Il
    530                 535                 540
Glu Glu Asp Asn Leu Glu Pro Trp Lys Ala Asn Asn Lys Asn Ala Ty
545                 550                 555                 560
Val Asp His Thr Gly Gly Val Asn Gly Thr Lys Ala Leu Tyr Val Hi
                565                 570                 575
Lys Asp Gly Gly Ile Ser Gln Phe Ile Gly Asp Lys Leu Lys Pro Ly
            580                 585                 590
Thr Glu Tyr Val Ile Gln Tyr Thr Val Lys Gly Lys Pro Ser Ile Hi
        595                 600                 605
Leu Lys Asp Glu Asn Thr Gly Tyr Ile His Tyr Glu Asp Thr Asn As
    610                 615                 620
```

```
        Asn Leu Glu Asp Tyr Gln Thr Ile Asn Lys Arg Phe Thr Thr Gly Th
        625                 630                 635                 640

Asp Leu Lys Gly Val Tyr Leu Ile Leu Lys Ser Gln Asn Gly Asp Gl
                        645                 650                 655

Ala Trp Gly Asp Asn Phe Ile Ile Leu Glu Ile Ser Pro Ser Glu Ly
                        660                 665                 670

Leu Leu Ser Pro Glu Leu Ile Asn Thr Asn Asn Trp Thr Ser Thr Gl
                    675                 680                 685

Ser Thr Asn Ile Ser Gly Asn Thr Leu Thr Leu Tyr Gln Gly Gly Ar
            690                 695                 700

Gly Ile Leu Lys Gln Asn Leu Gln Leu Asp Ser Phe Ser Thr Tyr Ar
        705                 710                 715                 720

Val Tyr Phe Ser Val Ser Gly Asp Ala Asn Val Arg Ile Arg Asn Se
                        725                 730                 735

Arg Glu Val Leu Phe Glu Lys Arg Tyr Met Ser Gly Ala Lys Asp Va
                        740                 745                 750

Ser Glu Met Phe Thr Thr Lys Phe Glu Lys Asp Asn Phe Tyr Ile Gl
                    755                 760                 765

Leu Ser Gln Gly Asn Asn Leu Tyr Gly Gly Pro Ile Val His Phe Ty
            770                 775                 780

Asp Val Ser Ile Lys Pro
        785                 790
```

(2) INFORMATION FOR SEQ ID NO: 9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
GCTCTAGAAG GAGGTAACTT ATGAACAAGA ATAATACTAA ATTAAGC            47
```

(2) INFORMATION FOR SEQ ID NO: 10:

(i) SEQUENCE CHARACTERISTICS:
        (A) LENGTH: 2035 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 158C2

(xi) SEQUENCE DESCRIPTION: SEQ ID NO: 10:

```
ATGAACAAGA ATAATACTAA ATTAAGCGCA AGGGCCTACC GAGTTTTATT GATTATTTTA60

ATGGCATTTA TGGATTTGCC ACTGGTATCA AAGACATTAT GAATATGATT TTTAAAACG120

ATACAGGTGG TAATCTAACC TTAGACGAAA TCCTAAAGAA TCAGCAGTTA CTAAATGAG180

TTTCTGGTAA ATTGGATGGG GTAAATGGGA GCTTAAATGA TCTTATCGCA CAGGGAAAC240

TAAATACAGA ATTAGCTAAG CAAATCTTAA AAGTTGCAAA TGAACAAAAT CAAGTTTTA300

ATGATGTTAA TAACAAACTA GACTGCGATA AATACGATGC TTAAAATATA TCTACCTAA360

ATTCACATCT ATGTTAAGTG ATGTACTGAA GCCAAAATTA TGTGCTTAAG TCTTGCAAA420

TGGAATTACC TTTAAGTAAC ATCTGCACCT TGGCAAGAAA TCTCCGACAA GCTAGATAT480
```

ATTAACGTAA ATGTGCTTAT TAACTCTACG CTTACTGAAA TTACACCTGC GTATCAACG 540

ATTAAATATG TGAATGAAAA ATTTGACGAT TTAACTTTTG CTACAGAAAA CACTTTAAA 600

GTAAAAAAGG ATAGCTCTCC TGCTGATATT CTTGACGAGT TAACTGAATT AACTGAACT 660

GCGAAAAGTG TTACAAAAAA TGACGTGGAT GGTTTTGAAT TTTACCTTAA TACATTCCA 720

GATGTAATGG TGGGAAATAA TTTATTCGGT CGTTCAGCTT TAAAAACTGC TTCGGAATT 780

ATTGCTAAAG AAAATGTGAA ACAAGTGGC AGTGAAGTAG GAAATGTTTA TAATTTCTT 840

ATTGTATTAA CAGCTCTACA AGCAAAAGCT TTTCTTACTT TAACAACATG CCGAAAATT 900

TTAGGCTTAG CAGATATTGA TTATACTTCT ATCATGAATG AGCATTTAAA TAAGGAAAA 960

GAGGAATTTA GAGTAAACAT CCTTCCCACA CTTTCTAATA CCTTTTCTAA TCCTAATT 1020

GCAAAGCTA AGGGAAGTAA TGAAGATACA AAGATGATTG TGGAAGCTAA ACCAGGAT 1080

GTTTTGGTTG GATTTGAAAT GAGCAATAAT TCAATTACAG TATTAAAAGC ATATCAAG 1140

AAGCTAAAAA AAGATTATCA AATTGATAAG GATTCGTTAT CAGAAATAAT ATATAGTA 1200

TGATACGGAT AAATTATTAT GTCCGGATCA ATCTGAACAA TATATTATAC AAAGAACA 1260

GCATTTCCAA ATGAATATGT TATTACTAAA ATTGCTTTTA CTAAAAAAAT GAACAGTT 1320

AGGTATGAGG CGACAGCGAA TTTTTATGAT TCTTCTACAG GGGATATTGA TCTAAATA 1380

ACAAAAGTAG AATCAAGTGA AGCGGAGTAT AGTATGCTAA AAGCTAGTGA TGATGAAG 1440

TACATGCCGC TAGGTCTTAT CAGTGAAACA TTTTTAAATC CAATTAATGG ATTTAGGC 1500

GCAGTCGATG AAAATTCCAG ACTAGTAACT TTAACATGTA GATCATATTT AAGAGAGA 1560

TTGTTAGCGA CAGATTTAAA TAATAAAGAA ACTAAATTGA TTGTCCCACC TAATGTTT 1620

ATTAGCAATA TTGTAGAGAA TGGAAATATA GAAATGGACA CCTTAGAACC ATGGAAGG 1680

AATAATGAGA ATGCGAATGT AGATTATTCA GGCGGAGTGA ATGGAACTAG AGCTTTAT 1740

GTTCATAAGG ATGGTGAATT CTCACATTTT ATTGGAGACA AGTTGAAATC TAAAACAG 1800

TACTTGATTC GATATATTGT AAAAGGAAAA GCTTCTATTT TTTAAAAGA TGAAAGAA 1860

GAAAATTACA TTTACGAGGA TACAAATAAT AATTTAGAAG ATTATCAAAC TATTACTA 1920

CGTTTTACTA CAGGAACTGA TTCGACAGGA TTTTATTTAT TTTTTACTAC TCAAGATG 1980

AATGAAGCTT GGGGAGACAC TTTTTTTCTC TAGAAAGAGG TAACTTATGA ACAAG    2035

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CATCCTCCCT ACACTTTCTA A    21

(2) INFORMATION FOR SEQ ID NO: 12:

(i) SEQUENCE CHARACTERISTICS:
        (A) LENGTH: 950 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (C) INDIVIDUAL ISOLATE: 49C-pt1

(xi) SEQUENCE DESCRIPTION: SEQ ID NO: 12:

```
AAACTAGAGG GAGTGATAAG GATGCGAAAA TCATTATGGA AGCTAAACCT GGATATGCTT  60
TAGTTGGATT TGAAATAAGT AAGGATTCAA TTGCAGTATT AAAAGTTTAT CAGGCAAAG  120
TAAAACACAA CTATCAAATT GATAAGGATT CGTTATCAGA AATTGTTTAT GGTGATATA  180
ATAAATTATT ATGTCCGGAT CAATCTGAAC AAATGTATTA TACAAATAAA ATAGCATTT  240
CAAATGAATA TGTTATCACT AAAATTGCTT TTACTAAAAA ACTGAACAGT TTAAGATAT  300
AGGTCACAGC GAATTTTTAT GACTCTTCTA CAGGAGATAT TGATCTAAAT AAGAAAAAA  360
TAGAATCAAG TGAAGCGGAG TTTAGTATGC TAAATGCTAA TAATGATGGT GTTTATATG  420
CGATAGGTAC TATAAGTGAA ACATTTTTGA CTCCAATTAA TGGATTTGGC CTCGTAGTC  480
ATGAAAATTC AAGACTAGTA ACTTTGACAT GTAAATCATA TTTAAGAGAG ACATTGTTA  540
CAACAGACTT AAGTAATAAA GAAACTAAAC TGATTGTCCC ACCTAATGGT TTTATTAGC  600
ATATTGTAGA AAATGGGAAC TTAGAGGGAG AAAACTTAGA GCCGTGGGAA AGCAAATAA  660
AAAAATGCGT ATGTAGATCA TACCGGAGGT GTAAATGGAA CTAAAGTTTT ATATGTTCA  720
GAGGATGGTG AGTTCTCACA ATTTATTGGG GATAAATTGA AATTGAAAAC AGAATATGT  780
ATTCCATATA TTGTAAAGGG GAAAGCTGCT ATTTATTTAA AAGATGAAAA AAATGGGGA  840
TACATATCAT GAAGAAACAT CATAATGCAA TTGAAGATTT TTCCAGCTGT AACTTCAAT  900
ATGATTTTCG CATCCTTATC ATCCCTCTAG CTTTTTCATA ATAGGATAGA            950
```

(2) INFORMATION FOR SEQ ID NO: 13:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 13:

```
AAATTATGCG CTAAGTCTGC                                              20
```

(2) INFORMATION FOR SEQ ID NO: 14:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 14:

```
TTGATCCGGA CATAATAAT                                               19
```

(2) INFORMATION FOR SEQ ID NO: 15:

(i) SEQUENCE CHARACTERISTICS:
       (A) LENGTH: 176 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:

(C) INDIVIDUAL ISOLATE: 49C-pt2

(xi) SEQUENCE DESCRIPTION: SEQ ID NO: 15:

GTAAATTATG CGCTAAGTCT GCACCTTTTT TCACTGTTAC TAAACATCAC TTTTCCTATA 60

TCCCCTTAGC TCTTATGGAT TATTGAGCAA ACTTATCTTG TTAATTACTA CTCCCCATC 120

TATGCTAAAC AAAAACCAAA CAAACATTAT CTATTATATG TCCGGATCAA AATGTA 176

(2) INFORMATION FOR SEQ ID NO: 16:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 16:

GGRTTAMTTG GRTAYTATTT 20

(2) INFORMATION FOR SEQ ID NO: 17:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 17:

ATATCKWAYA TTKGCATTTA 20

(2) INFORMATION FOR SEQ ID NO: 18:

(i) SEQUENCE CHARACTERISTICS:
    (A) LENGTH: 1076 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (C) INDIVIDUAL ISOLATE: 10E1

(xi) SEQUENCE DESCRIPTION: SEQ ID NO: 18:

TGGGATTACT TGGATATTAT TTCCAGGATC AAAAGTTTCA GCAACTTGCT TTGATGGCAC 60

ATAGACAAGC TTCTGATTTG GAAATCCCGA AGATGACGT GAAACAGTTA CTATCCAAG 120

AGCAGCAACA CATTCAATCT GTTAGATGGC TTGGCTATAT TCAGCCACCT CAAACAGGA 180

ACTATGTATT GTCAACCTCA TCCGACCAAC AGGTCGTGAT TGAACTCGAT GGAAAAACC 240

TTGTCAATCA AACTTCTATG ACAGAACCGA TTCAACTCGA AAAAGATAAG CTCTATAAA 300

TTAGAATTGA ATATGTCCCA GAAGATACAA AGAACAAGA GAACCTCCTT GACTTTCAG 360

TCAACTGGTC GATTTCAGGA TCAGAGATAG AACCAATTCC GGAGAATGCT TTCCATTTA 420

CAAATTTTTC TCGTAAACAA GATCAAGAGA AAATCATCCC TGAAACCAGT TGTTTCAG 480

AACAAGGAGA TGAGAAAAAA GTATCTCGCA GTAAGAGATC TTTAGCTACA AATCCTATC 540

GTGATACAGA TGATGATAGT ATTTATGATG AATGGGAAAC GGAAGGATAC ACGATACGG 600

AACAAATAGC AGTGAAATGG GACGATTCTA TGAAGGATAG AGGTTATACC AAATATGTG 660

CAAACCCCTA TAAGTCTCAT ACAGTAGGAG ATCCATACAC AGATTGGGAA AAAGCGGCT 720

-continued

```
GCCGTATCGA TAACGGTGTC AAAGCAGAAG CCAGAAATCC TTTAGTCGCG GCCTATCCA 780

CTGTTGGTGT ACATATGGAA AGATTAATTG TCTCCGAAAA ACAAAATATA TCAACAGGG 840

TTGGAAAAAC TGTATCTGCG TCTATGTCCG CAAGCAATAC CGCAGCGATT ACGGCAGGT 900

TTGATGCAAC AGCCGGTGCC TCTTTACTCG GGCCATCTGG AAGTGTCACG GCTCATTTT 960

CTTATACAGG ATCTAGTACA TCCACCGTTG AAGATAGCTC CAGCCGGAAT TGGAGTCA 1020

ACCTTGGGAT CGATACGGGA CAATCTGCAT ATTTAAATGC CAAATGTACG ATATAA    1076
```

(2) INFORMATION FOR SEQ ID NO: 19:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 10E1

(xi) SEQUENCE DESCRIPTION: SEQ ID NO: 19:

```
Gly Leu Leu Gly Tyr Tyr Phe Gln Asp Gln Lys Phe Gln Gln Leu Al
 1               5                  10                  15

Leu Met Ala His Arg Gln Ala Ser Asp Leu Glu Ile Pro Lys Asp As
                20                  25                  30

Val Lys Gln Leu Leu Ser Lys Glu Gln Gln His Ile Gln Ser Val Ar
            35                  40                  45

Trp Leu Gly Tyr Ile Gln Pro Pro Gln Thr Gly Asp Tyr Val Leu Se
    50                  55                  60

Thr Ser Ser Asp Gln Gln Val Val Ile Glu Leu Asp Gly Lys Thr Il
65                  70                  75                  80

Val Asn Gln Thr Ser Met Thr Glu Pro Ile Gln Leu Glu Lys Asp Ly
                85                  90                  95

Leu Tyr Lys Ile Arg Ile Glu Tyr Val Pro Glu Asp Thr Lys Glu Gl
            100                 105                 110

Glu Asn Leu Leu Asp Phe Gln Leu Asn Trp Ser Ile Ser Gly Ser Gl
        115                 120                 125

Ile Glu Pro Ile Pro Glu Asn Ala Phe His Leu Pro Asn Phe Ser Ar
    130                 135                 140

Lys Gln Asp Gln Glu Lys Ile Ile Pro Glu Thr Ser Leu Phe Gln Gl
145                 150                 155                 160

Gln Gly Asp Glu Lys Lys Val Ser Arg Ser Lys Arg Ser Leu Ala Th
                165                 170                 175

Asn Pro Ile Arg Asp Thr Asp Asp Ser Ile Tyr Asp Glu Trp Gl
            180                 185                 190

Thr Glu Gly Tyr Thr Ile Arg Glu Gln Ile Ala Val Lys Trp Asp As
        195                 200                 205

Ser Met Lys Asp Arg Gly Tyr Thr Lys Tyr Val Ser Asn Pro Tyr Ly
    210                 215                 220

Ser His Thr Val Gly Asp Pro Tyr Thr Asp Trp Glu Lys Ala Ala Gl
225                 230                 235                 240

Arg Ile Asp Asn Gly Val Lys Ala Glu Ala Arg Asn Pro Leu Val Al
                245                 250                 255

Ala Tyr Pro Thr Val Gly Val His Met Glu Arg Leu Ile Val Ser Gl
            260                 265                 270
```

```
    Lys Gln Asn Ile Ser Thr Gly Leu Gly Lys Thr Val Ser Ala Ser Me
        275                 280                 285

Ser Ala Ser Asn Thr Ala Ala Ile Thr Ala Gly Ile Asp Ala Thr Al
        290                 295                 300

Gly Ala Ser Leu Leu Gly Pro Ser Gly Ser Val Thr Ala His Phe Se
    305                 310                 315                 320

Tyr Thr Gly Ser Ser Thr Ser Thr Val Glu Asp Ser Ser Arg As
                    325                 330                 335

Trp Ser Gln Asp Leu Gly Ile Asp Thr Gly Gln Ser Ala Tyr Leu As
                340                 345                 350

Ala Lys Cys Thr Ile
                355
```

(2) INFORMATION FOR SEQ ID NO: 20:

(i) SEQUENCE CHARACTERISTICS:
        (A) LENGTH: 1045 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 31J2

(xi) SEQUENCE DESCRIPTION: SEQ ID NO: 20:

```
TGGGTTACTT GGGTATTATT TTAAAGGAAA AGATTTTAAT AATCTTACTA TATTTGCTCC  60

AACACGTGAG AATACTCTTA TTTATGATTT AGAAACAGCG AATTCTTTAT TAGATAAGC 120

ACAACAAACC TATCAATCTA TTCGTTGGAT CGGTTTAATA AAAAGCAAAA AAGCTGGAG 180

TTTTACCTTT CAATTATCGG ATGATGAGCA TGCTATTATA GAAATCGATG GGAAAGTTA 240

TTCGCAAAAA GGCCAAAAGA AACAAGTTGT TCATTTAGAA AAAGATAAAT TAGTTCCCA 300

CAAAATTGAA TATCAATCTG ATAAAGCGTT AAACCCAGAT AGTCAAATGT TTAAAGAAT 360

GAAATTATTT AAAATAAATA GTCAAAAACA ATCTCAGCAA GTGCAACAAG ACGAATTGA 420

AAATCCTGAA TTTGGTAAAG AAAAAACTCA AACATATTTA AAGAAAGCAT CGAAAAGCA 480

CTTGTTTAGC AATAAAAGTA AACGAGATAT AGATGAAGAT ATAGATGAGG ATACAGATA 540

AGATGGAGAT GCCATTCCTG ATGTATGGGA AGAAAATGGG TATACCATCA AAGGAAGAG 600

AGCTGTTAAA TGGGACGAAG GATTAGCTGA TAAGGGATAT AAAAAGTTTG TTTCCAATC 660

TTTTAGACAG CACACTGCTG GTGACCCCTA TAGTGACTAT GAAAAGGCAT CAAAAGATT 720

GGATTTATCT AATGCAAAAG AAACATTTAA TCCATTGGTG GCTGCTTTTC CAAGTGTCA 780

TGTTAGCTTG GAAAATGTCA CCATATCAAA AGATGAAAAT AAAACTGCTG AAATTGCGT 840

TACTTCATCG AATAATTGGT CCTATACAAA TACAGAGGGG GCATCTATTG AAGCTGGAA 900

TGGACCAGAA GGTTTGTTGT CTTTTGGAGT AAGTGCCAAT TATCAACATT CTGAAACAG 960

GGCCAAAGAG TGGGGTACAA CTAAGGGAGA CGCAACACAA TATAATACAG CTTCAGCA 1020

ATATCTAAAT GCCAATGTAC GATAT                                    1045
```

(2) INFORMATION FOR SEQ ID NO: 21:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: peptide (vi) ORIGINAL SOURCE:
    (C) INDIVIDUAL ISOLATE: 31J2

(xi) SEQUENCE DESCRIPTION: SEQ ID NO: 21:

```
Gly Leu Leu Gly Tyr Tyr Phe Lys Gly Lys Asp Phe Asn Asn Leu Th
1               5                   10                  15
Ile Phe Ala Pro Thr Arg Glu Asn Thr Leu Ile Tyr Asp Leu Glu Th
            20                  25                  30
Ala Asn Ser Leu Leu Asp Lys Gln Gln Thr Tyr Gln Ser Ile Ar
        35                  40                  45
Trp Ile Gly Leu Ile Lys Ser Lys Lys Ala Gly Asp Phe Thr Phe Gl
    50                  55                  60
Leu Ser Asp Asp Glu His Ala Ile Ile Glu Ile Asp Gly Lys Val Il
65                  70                  75                  80
Ser Gln Lys Gly Gln Lys Lys Gln Val Val His Leu Glu Lys Asp Ly
                85                  90                  95
Leu Val Pro Ile Lys Ile Glu Tyr Gln Ser Asp Lys Ala Leu Asn Pr
            100                 105                 110
Asp Ser Gln Met Phe Lys Glu Leu Lys Leu Phe Lys Ile Asn Ser Gl
        115                 120                 125
Lys Gln Ser Gln Gln Val Gln Gln Asp Glu Leu Arg Asn Pro Glu Ph
    130                 135                 140
Gly Lys Glu Lys Thr Gln Thr Tyr Leu Lys Lys Ala Ser Lys Ser Se
145                 150                 155                 160
Leu Phe Ser Asn Lys Ser Lys Arg Asp Ile Asp Glu Asp Ile Asp Gl
                165                 170                 175
Asp Thr Asp Thr Asp Gly Asp Ala Ile Pro Asp Val Trp Glu Glu As
            180                 185                 190
Gly Tyr Thr Ile Lys Gly Arg Val Ala Val Lys Trp Asp Glu Gly Le
        195                 200                 205
Ala Asp Lys Gly Tyr Lys Lys Phe Val Ser Asn Pro Phe Arg Gln Hi
    210                 215                 220
Thr Ala Gly Asp Pro Tyr Ser Asp Tyr Glu Lys Ala Ser Lys Asp Le
225                 230                 235                 240
Asp Leu Ser Asn Ala Lys Glu Thr Phe Asn Pro Leu Val Ala Ala Ph
                245                 250                 255
Pro Ser Val Asn Val Ser Leu Glu Asn Val Thr Ile Ser Lys Asp Gl
            260                 265                 270
Asn Lys Thr Ala Glu Ile Ala Ser Thr Ser Asn Asn Trp Ser Ty
        275                 280                 285
Thr Asn Thr Glu Gly Ala Ser Ile Glu Ala Gly Ile Gly Pro Glu Gl
    290                 295                 300
Leu Leu Ser Phe Gly Val Ser Ala Asn Tyr Gln His Ser Glu Thr Va
305                 310                 315                 320
Ala Lys Glu Trp Gly Thr Thr Lys Gly Asp Ala Thr Gln Tyr Asn Th
                325                 330                 335
Ala Ser Ala Gly Tyr Leu Asn Ala Asn Val Arg Tyr
            340                 345
```

(2) INFORMATION FOR SEQ ID NO: 22:

(i) SEQUENCE CHARACTERISTICS:
    (A) LENGTH: 1641 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 33D2

(xi) SEQUENCE DESCRIPTION: SEQ ID NO: 22:

```
CCAAAGGGGG NTTAAACCNG GANGGTTNNN TNNTTNNTTN TNGAANCCCA NTTGGAAACC    60
CNATNAAATT CNTGGTTANT GGTNGTGAGT GNNTNTTTTA NCNGAGNTTG CCCNTTTGN   120
TACCNGGATT TNAAGGCAGA ANTTNTTNNT NGCTNNTTAA AGGTTNTGNT TNTNANTGA   180
TTTTTTNGGN TTTGCCCAAA AAACAAGGAT GAATCCTGTT ATTCCNCCCT NGAAAAAAT   240
GAAACGGAAC AACGTGAGTA TGATAAACAT CTTTTACAAA CTGCGACATC TTGTTGAAA   300
TGCCTTTTTT GAAAANNTAA AAGGTTTCGT GGCATTGCCA CACGTTATAC AAAAACCAC   360
TCTGCTTTTA GAGGGGCTGT TACCTTGGCT GCTATTTCTC TGTGGTTGAA TCTCGTATA   420
ACACTATCTA GTCTATACAT CTTATCTTTT CATCATGATT CCAGTCGTAC ATTTACTCA   480
AAATAGAAAG GATGACCCCT ATGCAATTAA AAAATGTATA CAAATGTTTA ACCATTACA   540
CGCTTTTGGC TCAAATCGCC GCCTTCCCGT CTTCCTCTTT TGCGGAAGAC GGGAAGAAA   600
AAGAAGAAAA TACAGCTAAA ACAGAACATC AACAGAAAAA AGAAACAAAA CCAGTTGTG   660
GATTAATTGG TCACTATTTT ACTGATGATC AGTTTACTAA CACAGCATTT ATTCAAGTA   720
GAGAAAAAAG TAAATTACTA GATTCAAAAA TAGTAAAGCA AGATATGTCC AATTTGAAA   780
CCATTCGATG GGAAGGAAAT GTGAAACCTC CTGAAACAGG AGAATATCTA CTTTCCACG   840
CCTCTAATGA AAATGTTACA GTAAAAGTAG ATGGAGAAAC TGTTATTAAC AAAGCTAAC   900
TGGAAAAAGC AATGAAACTC GAAAAGATA AACCACACTC TATTGAAATT GAATATCAT   960
TTCCTGAGAA CGGGAAGGAA CTACAATTAT TTTGGCAAAT AAATGACCAG AAAGCTGT   1020
AAATCCCAGA AAAAAACATA CTATCACCAA ATCTTTCTGA ACAGATACAA CCGCAACA   1080
GTTCAACTCA ATCTCAACAA AATCAAAATG ATAGGGATGG GGATAAAATC CCTGATAG   1140
TAGAAGAAAA TGGCTATACA TTTAAAGACG GTGCGATTGT TGCCTGGAAC GATTCCTA   1200
CAGCACTAGG CTATAAAAAA TACATATCCA ATTCTAATAA GGCTAAAACA GCTGCTGA   1260
CCTATACGGA CTTTGAAAAA GTAACAGGAC ACATGCCGGA GGCAACTAAA GATGAAGT   1320
AAGATCCACT AGTAGCCGCT TATCCCTCGG TAGGTGTTGC TATGGAAAAA TTTCATTT   1380
CTAGAAATGA AACGGTCACT GAAGGAGACT CAGGTACTGT TTCAAAAACC GTAACCAA   1440
CAAGCACAAC AACAAATAGC ATCGATGTTG GGGGATCCAT TGGATGGGGA GAAAAAGG   1500
TTTCTTTTTC ATTCTCTCCC AAATATACGC ATTCTTGGAG TAATAGTACC GCTGTTGC   1560
ATACTGAAAG TAGCACATGG TCTTCACAAT TAGCGTATAA TCCTTCAGAA CGTGCTTT   1620
TAAATGCCAA TATACGATAT A                                           1641
```

(2) INFORMATION FOR SEQ ID NO: 23:

(i) SEQUENCE CHARACTERISTICS:
        (A) LENGTH: 327 amino acids
        (B) TYPE: amino acid
        (C) STRANDEDNESS: single
        (D) TOPOLOGY: linear (ii) MOLECULE TYPE: peptide (vi) ORIGINAL SOURCE:

(C) INDIVIDUAL ISOLATE: 33D2

(xi) SEQUENCE DESCRIPTION: SEQ ID NO: 23:

```
Gly Leu Ile Gly His Tyr Phe Thr Asp Asp Gln Phe Thr Asn Thr Al
 1               5                  10                  15

Phe Ile Gln Val Gly Glu Lys Ser Lys Leu Leu Asp Ser Lys Ile Va
                20                  25                  30

Lys Gln Asp Met Ser Asn Leu Lys Ser Ile Arg Trp Glu Gly Asn Va
            35                  40                  45

Lys Pro Pro Glu Thr Gly Glu Tyr Leu Leu Ser Thr Ser Ser Asn Gl
50                  55                  60

Asn Val Thr Val Lys Val Asp Gly Glu Thr Val Ile Asn Lys Ala As
65                  70                  75                  80

Met Glu Lys Ala Met Lys Leu Glu Lys Asp Lys Pro His Ser Ile Gl
                85                  90                  95

Ile Glu Tyr His Val Pro Glu Asn Gly Lys Glu Leu Gln Leu Phe Tr
                100                 105                 110

Gln Ile Asn Asp Gln Lys Ala Val Lys Ile Pro Glu Lys Asn Ile Le
            115                 120                 125

Ser Pro Asn Leu Ser Glu Gln Ile Gln Pro Gln Gln Arg Ser Thr Gl
130                 135                 140

Ser Gln Gln Asn Gln Asn Asp Arg Asp Gly Asp Lys Ile Pro Asp Se
145                 150                 155                 160

Leu Glu Glu Asn Gly Tyr Thr Phe Lys Asp Gly Ala Ile Val Ala Tr
                165                 170                 175

Asn Asp Ser Tyr Ala Ala Leu Gly Tyr Lys Lys Tyr Ile Ser Asn Se
            180                 185                 190

Asn Lys Ala Lys Thr Ala Ala Asp Pro Tyr Thr Asp Phe Glu Lys Va
            195                 200                 205

Thr Gly His Met Pro Glu Ala Thr Lys Asp Glu Val Lys Asp Pro Le
            210                 215                 220

Val Ala Ala Tyr Pro Ser Val Gly Val Ala Met Glu Lys Phe His Ph
225                 230                 235                 240

Ser Arg Asn Glu Thr Val Thr Glu Gly Asp Ser Gly Thr Val Ser Ly
                245                 250                 255

Thr Val Thr Asn Thr Ser Thr Thr Thr Asn Ser Ile Asp Val Gly Gl
            260                 265                 270

Ser Ile Gly Trp Gly Glu Lys Gly Phe Ser Phe Ser Phe Ser Pro Ly
            275                 280                 285

Tyr Thr His Ser Trp Ser Asn Ser Thr Ala Val Ala Asp Thr Glu Se
            290                 295                 300

Ser Thr Trp Ser Ser Gln Leu Ala Tyr Asn Pro Ser Glu Arg Ala Ph
305                 310                 315                 320

Leu Asn Ala Asn Ile Arg Tyr
                325
```

(2) INFORMATION FOR SEQ ID NO: 24:

(i) SEQUENCE CHARACTERISTICS:
    (A) LENGTH: 1042 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:

(C) INDIVIDUAL ISOLATE: 66D3

(xi) SEQUENCE DESCRIPTION: SEQ ID NO: 24:

```
TTAATTGGGT ACTATTTTAA AGGAAAAGAT TTTAATAATC TTACTATATT TGCTCCAACA    60
CGTGAGAATA CTCTTATTTA TGATTTAGAA ACAGCGAATT CTTTATTAGA TAAGCAACA   120
CAAACCTATC AATCTATTCG TTGGATCGGT TTAATAAAAA GCAAAAAAGC TGGAGATTT   180
ACCTTTCAAT TATCGGATGA TGAGCATGCT ATTATAGAAA TCGATGGGAA AGTTATTTC   240
CAAAAAGGCC AAAAGAAACA AGTTGTTCAT TTAGAAAAAG ATAAATTAGT TCCCATCAA   300
ATTGAATATC AATCTGATAA AGCGTTAAAC CCAGATAGTC AAATGTTTAA AGAATTGAA   360
TTATTTAAAA TAAATAGTCA AAACAATCT CAGCAAGTGC AACAAGACGA ATTGAGAAA    420
CCTGAATTTG GTAAAGAAAA AACTCAAACA TATTTAAAGA AAGCATCGAA AAGCAGCCT   480
TTTAGCAATA AAAGTAAACG AGATATAGAT GAAGATATAG ATGAGGATAC AGATACAGA   540
GGAGATGCCA TTCCTGATGT ATGGGAAGAA AATGGGTATA CCATCAAAGG AAGAGTAGC   600
GTTAAATGGG ACGAAGGATT AGCTGATAAG GGATATAAAA AGTTTGTTTC CAATCCTTT   660
AGACAGCACA CTGCTGGTGA CCCCTATAGT GACTATGAAA AGGCATCAAA AGATTTGGA   720
TTATCTAATG CAAAAGAAAC ATTTAATCCA TTGGTGGCTG CTTTTCCAAG TGTCAATGT   780
AGCTTGGAAA ATGTCACCAT ATCAAAAGAT GAAAATAAAA CTGCTGAAAT TGCGTCTAC   840
TCATCGAATA ATTGGTCCTA TACAAATACA GAGGGGGCAT CTATTGAAGC TGGAATTGG   900
CCAGAAGGTT TGTTGTCTTT TGGAGTAAGT GCCAATTATC AACATTCTGA AACAGTGGC   960
AAAGAGTGGG GTACAACTAA GGGAGACGCA ACACAATATA ATACAGCTTC AGCAGGAT  1020
CTAAATGCCA ATGTACGATA TA                                        1042
```

(2) INFORMATION FOR SEQ ID NO: 25:

(i) SEQUENCE CHARACTERISTICS:
        (A) LENGTH: 347 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 66D3

(xi) SEQUENCE DESCRIPTION: SEQ ID NO: 25:

```
Leu Ile Gly Tyr Tyr Phe Lys Gly Lys Asp Phe Asn Asn Leu Thr Il
 1               5                  10                  15
Phe Ala Pro Thr Arg Glu Asn Thr Leu Ile Tyr Asp Leu Glu Thr Al
            20                  25                  30
Asn Ser Leu Leu Asp Lys Gln Gln Thr Tyr Gln Ser Ile Arg Tr
        35                  40                  45
Ile Gly Leu Ile Lys Ser Lys Ala Gly Asp Phe Thr Phe Gln Le
    50                  55                  60
Ser Asp Asp Glu His Ala Ile Ile Glu Ile Asp Gly Lys Val Ile Se
65                  70                  75                  80
Gln Lys Gly Gln Lys Lys Gln Val Val His Leu Glu Lys Asp Lys Le
                85                  90                  95
Val Pro Ile Lys Ile Glu Tyr Gln Ser Asp Lys Ala Leu Asn Pro As
            100                 105                 110
Ser Gln Met Phe Lys Glu Leu Lys Leu Phe Lys Ile Asn Ser Gln Ly
        115                 120                 125
```

```
       Gln Ser Gln Gln Val Gln Gln Asp Glu Leu Arg Asn Pro Glu Phe Gl
           130                 135                 140

Lys Glu Lys Thr Gln Thr Tyr Leu Lys Lys Ala Ser Lys Ser Ser Le
       145                 150                 155                 160

Phe Ser Asn Lys Ser Lys Arg Asp Ile Asp Glu Asp Ile Asp Glu As
                       165                 170                 175

Thr Asp Thr Asp Gly Asp Ala Ile Pro Asp Val Trp Glu Glu Asn Gl
                   180                 185                 190

Tyr Thr Ile Lys Gly Arg Val Ala Val Lys Trp Asp Glu Gly Leu Al
               195                 200                 205

Asp Lys Gly Tyr Lys Lys Phe Val Ser Asn Pro Phe Arg Gln His Th
           210                 215                 220

Ala Gly Asp Pro Tyr Ser Asp Tyr Glu Lys Ala Ser Lys Asp Leu As
       225                 230                 235                 240

Leu Ser Asn Ala Lys Glu Thr Phe Asn Pro Leu Val Ala Ala Phe Pr
                       245                 250                 255

Ser Val Asn Val Ser Leu Glu Asn Val Thr Ile Ser Lys Asp Glu As
                   260                 265                 270

Lys Thr Ala Glu Ile Ala Ser Thr Ser Ser Asn Asn Trp Ser Tyr Th
               275                 280                 285

Asn Thr Glu Gly Ala Ser Ile Glu Ala Gly Ile Gly Pro Glu Gly Le
           290                 295                 300

Leu Ser Phe Gly Val Ser Ala Asn Tyr Gln His Ser Glu Thr Val Al
       305                 310                 315                 320

Lys Glu Trp Gly Thr Thr Lys Gly Asp Ala Thr Gln Tyr Asn Thr Al
                       325                 330                 335

Ser Ala Gly Tyr Leu Asn Ala Asn Val Arg Tyr
                   340                 345
```

(2) INFORMATION FOR SEQ ID NO: 26:

(i) SEQUENCE CHARACTERISTICS:
        (A) LENGTH: 1278 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 68F (xi) SEQUENCE DESCRIPTION: SEQ ID NO: 26:

```
TGGATTACTT GGGTACTATT TTAAAGGGAA AGATTTTAAT GATCTTACTG TATTTGCACC  60

AACGCGTGGG AATACTCTTG TATATGATCA ACAAACAGCA AATACATTAC TAAATCAAA  120

ACAACAAGAC TTTCAGTCTA TTCGTTGGGT TGGTTTAATT CAAAGTAAAG AAGCAGGCG  180

TTTTACATTT AACTTATCAG ATGATGAACA TACGATGATA GAAATCGATG GAAAGTTA   240

TTCTAATAAA GGGAAAGAAA AACAAGTTGT CCATTTAGAA AAAGGACAGT TCGTTTCTA  300

CAAAATAGAA TATCAAGCTG ATGAACCATT TAATGCGGAT AGTCAAACCT TTAAAAATT  360

GAAACTCTTT AAAGTAGATA CTAAGCAACA GTCCCAGCAA ATTCAACTAG ATGAATTAA  420

AAACCCTGAA TTAATAAAA AGAAACACA AGAATTTCTA ACAAAAGCAA CAAAAACAA   480

CCTTATTACT CAAAAAGTGA AGAGTACTAG GGATGAAGAC ACGGATACAG ATGGAGATT  540

TATTCCAGAC ATTTGGGAAG AAAATGGGTA TACCATCCAA AATAAGATTG CCGTCAAAT  600
```

```
GGATGATTCA TTAGCAAGTA AAGGATATAC GAAATTTGTT TCAAACCCAC TAGATACTC  660

CACGGTTGGA GATCCTTATA CAGATTATGA AAAAGCAGCA AGGGATTTAG ATTTGTCAA  720

TGCAAAAGAA ACATTTAACC CATTAGTTGC GGCTTTTCCA AGTGTGAATG TGAGTATGG  780

AAAAGTGATA TTGTCTCCAG ATGAGAACTT ATCAAATAGT ATCGAGTCTC ATTCATCTA  840

GAATTGGTCG TATACGAATA CAGAAGGGGC TTCTATTGAA GCTGGTGGGG GAGCATTAG  900

CCTATCTTTT GGTGTAAGTG CAAACTATCA ACATTCTGAA ACAGTTGGGT ATGAATGGG  960

AACATCTACG GGAAATACTT CGCAATTTAA TACAGCTTCA GCGGGGTATT TAAATGCG  1020

TGTTCGCTAC AATAACGTGG GAACGGGTGC AATCTATGAT GTAAAGCCAA CAACGAGT  1080

TGTATTAAAT AAAGATACCA TCGCAACGAT AACAGCAAAA TCGAATACGA CTGCATTA  1140

TATCTCACCA GGACAAAGTT ATCCGAAACA AGGTCAAAAT GGAATCGCGA TCACATCG  1200

GGATGATTTT AACTCACATC CGATTACATT GAATAAGCAA CAGGTAGGTC AACTGTTA  1260

TAATACCCAA TTAATCCA                                               1278
```

(2) INFORMATION FOR SEQ ID NO: 27:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: peptide (vi) ORIGINAL SOURCE:
       (C) INDIVIDUAL ISOLATE: 68F (xi) SEQUENCE DESCRIPTION: SEQ ID NO: 27:

```
Gly Leu Leu Gly Tyr Tyr Phe Lys Gly Lys Asp Phe Asn Asp Leu Th
 1               5                  10                  15

Val Phe Ala Pro Thr Arg Gly Asn Thr Leu Val Tyr Asp Gln Gln Th
                20                  25                  30

Ala Asn Thr Leu Leu Asn Gln Lys Gln Gln Asp Phe Gln Ser Ile Ar
            35                  40                  45

Trp Val Gly Leu Ile Gln Ser Lys Glu Ala Gly Asp Phe Thr Phe As
     50                  55                  60

Leu Ser Asp Asp Glu His Thr Met Ile Glu Ile Asp Gly Lys Val Il
65                  70                  75                  80

Ser Asn Lys Gly Lys Glu Lys Gln Val Val His Leu Glu Lys Gly Gl
                85                  90                  95

Phe Val Ser Ile Lys Ile Glu Tyr Gln Ala Asp Glu Pro Phe Asn Al
                100                 105                 110

Asp Ser Gln Thr Phe Lys Asn Leu Lys Leu Phe Lys Val Asp Thr Ly
            115                 120                 125

Gln Gln Ser Gln Gln Ile Gln Leu Asp Glu Leu Arg Asn Pro Glu Ph
        130                 135                 140

Asn Lys Lys Glu Thr Gln Glu Phe Leu Thr Lys Ala Thr Lys Thr As
145                 150                 155                 160

Leu Ile Thr Gln Lys Val Lys Ser Thr Arg Asp Glu Asp Thr Asp Th
                165                 170                 175

Asp Gly Asp Ser Ile Pro Asp Ile Trp Glu Glu Asn Gly Tyr Thr Il
            180                 185                 190

Gln Asn Lys Ile Ala Val Lys Trp Asp Asp Ser Leu Ala Ser Lys Gl
        195                 200                 205
```

```
    Tyr Thr Lys Phe Val Ser Asn Pro Leu Asp Thr His Thr Val Gly As
        210                 215                 220

Pro Tyr Thr Asp Tyr Glu Lys Ala Ala Arg Asp Leu Asp Leu Ser As
    225                 230                 235                 240

Ala Lys Glu Thr Phe Asn Pro Leu Val Ala Ala Phe Pro Ser Val As
                    245                 250                 255

Val Ser Met Glu Lys Val Ile Leu Ser Pro Asp Glu Asn Leu Ser As
                260                 265                 270

Ser Ile Glu Ser His Ser Ser Thr Asn Trp Ser Tyr Thr Asn Thr Gl
                275                 280                 285

Gly Ala Ser Ile Glu Ala Gly Gly Ala Leu Gly Leu Ser Phe Gl
        290                 295                 300

Val Ser Ala Asn Tyr Gln His Ser Glu Thr Val Gly Tyr Glu Trp Gl
    305                 310                 315                 320

Thr Ser Thr Gly Asn Thr Ser Gln Phe Asn Thr Ala Ser Ala Gly Ty
                    325                 330                 335

Leu Asn Ala Asn Val Arg Tyr Asn Asn Val Gly Thr Gly Ala Ile Ty
                340                 345                 350

Asp Val Lys Pro Thr Thr Ser Phe Val Leu Asn Lys Asp Thr Ile Al
                355                 360                 365

Thr Ile Thr Ala Lys Ser Asn Thr Thr Ala Leu Ser Ile Ser Pro Gl
        370                 375                 380

Gln Ser Tyr Pro Lys Gln Gly Gln Asn Gly Ile Ala Ile Thr Ser Me
    385                 390                 395                 400

Asp Asp Phe Asn Ser His Pro Ile Thr Leu Asn Lys Gln Gln Val Gl
                    405                 410                 415

Gln Leu Leu Asn Asn Thr Gln Leu Ile
                420                 425
```

(2) INFORMATION FOR SEQ ID NO: 28:

(i) SEQUENCE CHARACTERISTICS:
        (A) LENGTH: 983 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 69AA2

(xi) SEQUENCE DESCRIPTION: SEQ ID NO: 28:

```
TGGATTACTT GGGTACTATT TTACTGATGA TCAGTTTACT AACACAGCAT TTATTCAAGT    60

AGGAGAAAAA AGTAAATTAC TAGATTCAAA AATAGTAAAA CAAGATATGT CCAATTTGA   120

ATCCATTCGA TGGGAAGGAA ATGTGAAACC TCCTGAAACA GGAGAATATC TACTTTCCA   180

GTCCTCTAAT GAAATGTTA CAGTAAAAGT AGATGGAGAA ACTGTTATTA CAAAGCTA    240

CATGGAAAAA GCAATGAAAC TCGAAAAAGA TAAACCACAC TCTATTGAAA TTGAATATC   300

TGTTCCTGAG AACGGGAAGG AACTACAATT ATTTTGGCAA ATAAATGACC AGAAAGCTG   360

TAAAATCCCA GAAAAAAACA TACTATCACC AAATCTTTCT GAACAGATAC AACCGCAAC   420

GCGTTCAACT CAATCTCAAC AAAATCAAAA TGATAGGGAT GGGGATAAAA TCCCTGATA   480

TTTAGAAGAA AATGGCTATA CATTTAAAGA CGGTGCGATT GTTGCCTGGA ACGATTCCT   540

TGCAGCACTA GGCTATAAAA AATACATATC CAATTCTAAT AAGGCTAAAA CAGCTGCTG   600

CCCCTATACG GACTTTGAAA AGTAACAGG ACACATGCCG GAGGCAACTA AAGATGAAG   660
```

-continued

```
AAAAGATCCA CTAGTAGCCG CTTATCCCTC GGTAGGTGTT GCTATGGAAA AATTTCATT720

TTCTAGAAAT GAAACGGTCA CTGAAGGAGA CTCAGGTACT GTTTCAAAAA CCGTAACCA780

TACAAGCACA ACAACAAATA GCATCGATGT TGGGGATCC ATTGGATGGG GAGAAAAAG840

ATTTTCTTTT TCATTCTCTC CCAAATATAC GCATTCTTGG AGTAATAGTA CCGCTGTTG900

TGATACTGAA AGTAGCACAT GGTCTTCACA ATTAGCGTAT AATCCTTCAG AACGTGCTN960

CTTAAATGCC AATAKACGAT NTA                                       983
```

(2) INFORMATION FOR SEQ ID NO: 29:

(i) SEQUENCE CHARACTERISTICS:
        (A) LENGTH: 327 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 69AA2

(xi) SEQUENCE DESCRIPTION: SEQ ID NO: 29:

```
Gly Leu Leu Gly Tyr Tyr Phe Thr Asp Asp Gln Phe Thr Asn Thr Al
 1               5                  10                  15

Phe Ile Gln Val Gly Glu Lys Ser Lys Leu Leu Asp Ser Lys Ile Va
             20                  25                  30

Lys Gln Asp Met Ser Asn Leu Lys Ser Ile Arg Trp Glu Gly Asn Va
         35                  40                  45

Lys Pro Pro Glu Thr Gly Glu Tyr Leu Leu Ser Thr Ser Ser Asn Gl
     50                  55                  60

Asn Val Thr Val Lys Val Asp Gly Glu Thr Val Ile Asn Lys Ala As
 65                  70                  75                  80

Met Glu Lys Ala Met Lys Leu Glu Lys Asp Lys Pro His Ser Ile Gl
                 85                  90                  95

Ile Glu Tyr His Val Pro Glu Asn Gly Lys Glu Leu Gln Leu Phe Tr
             100                 105                 110

Gln Ile Asn Asp Gln Lys Ala Val Lys Ile Pro Glu Lys Asn Ile Le
         115                 120                 125

Ser Pro Asn Leu Ser Glu Gln Ile Gln Pro Gln Gln Arg Ser Thr Gl
     130                 135                 140

Ser Gln Gln Asn Gln Asn Asp Arg Asp Gly Asp Lys Ile Pro Asp Se
145                 150                 155                 160

Leu Glu Glu Asn Gly Tyr Thr Phe Lys Asp Gly Ala Ile Val Ala Tr
                 165                 170                 175

Asn Asp Ser Tyr Ala Ala Leu Gly Tyr Lys Lys Tyr Ile Ser Asn Se
             180                 185                 190

Asn Lys Ala Lys Thr Ala Ala Asp Pro Tyr Thr Asp Phe Glu Lys Va
         195                 200                 205

Thr Gly His Met Pro Glu Ala Thr Lys Asp Glu Val Lys Asp Pro Le
     210                 215                 220

Val Ala Ala Tyr Pro Ser Val Gly Val Ala Met Glu Lys Phe His Ph
225                 230                 235                 240

Ser Arg Asn Glu Thr Val Thr Glu Gly Asp Ser Gly Thr Val Ser Ly
                 245                 250                 255

Thr Val Thr Asn Thr Ser Thr Thr Asn Ser Ile Asp Val Gly Gl
             260                 265                 270
```

```
            Ser Ile Gly Trp Gly Glu Lys Gly Phe Ser Phe Ser Phe Ser Pro Ly
                275                 280                 285

Tyr Thr His Ser Trp Ser Asn Ser Thr Ala Val Ala Asp Thr Glu Se
                290                 295                 300

Ser Thr Trp Ser Ser Gln Leu Ala Tyr Asn Pro Ser Glu Arg Ala Xa
            305                 310                 315                 320

Leu Asn Ala Asn Xaa Arg Xaa
                            325
```

(2) INFORMATION FOR SEQ ID NO: 30:

(i) SEQUENCE CHARACTERISTICS:
        (A) LENGTH: 1075 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 168G1

(xi) SEQUENCE DESCRIPTION: SEQ ID NO: 30:

```
TGGGTTAATT GGATATTATT TCCAGGATCA AAAATTTCAA CAACTCGCTT TAATGGTACA  60

TAGGCAAGCT TCTGATTTAA AAATACTGAA AGATGACGTG AAACATTTAC TATCCGAAG  120

TCAACAACAC ATTCAATCAG TAAGGTGGAT AGGCTATATT AAGCCACCTA AAACAGGAG  180

CTACGTATTG TCAACCTCAT CCGACCAACA GGTCATGATT GAACTAGATG GTAAAGTCA  240

TCTCAATCAG GCTTCTATGA CAGAACCTGT TCAACTTGAA AAAGATAAAC CGTATAAAA  300

TAAAATTGAA TATGTTCCGG AACAAACAGA AACACAAGAT ACGCTTCTTG ATTTTAAAC  360

GAACTGGTCT TTTTCAGGCG GAAAAACAGA AACGATTCCA GAAAATGCAT TTCTATTAC  420

AGACCTTTCT CGTAAACAAG ATCAAGAAAA GCTTATTCCT GAGGCAAGTT TATTTCAGA  480

ACCTGGAGAC GAGAAAAAAA TATCTCGAAG TAAACGGTCC TTTAACTACA GATTCTCTA  540

ATGATACAAG ATGATGATGG GATTTCGGAT GCGTGGGAAA CAGAAGGATA CACGATACA  600

AGACAACTGG CAGTGAAATG GGACGATTCT ATGAAGGATC GAGGGTATAC CAAATATGT  660

TCTAATCCCT ATAATTCCCA TACAGTAGGG GATCCATACA CAGATTGGGA AAAAGCGGC  720

GGACGTATTG ATAAGGCGAT CAAAGGAGAA GCTAGGAATC CTTTAGTCGC GGCCTATCC  780

ACCGTTGGTG TACATATGGA AAAACTGATT GTCTCCGAGA AACAAAACAT ATCAACTGG  840

CTCGGAAAAA CAATATCTGC GTCAATGTCT GCAAGTAATA CCGCAGCGAT TACAGCGGG  900

ATTGATACGA CGGCTGGTGC TTCTTTACTT GGACCGTCTG GAAGCGTCAC GGCTCATTT  960

TCTGATACAG GATCCAGTAC ATCCACTGTT GAAAATAGCT CAAGTAATAA TTGGAGTC  1020

GATCTTGGAA TCGATACGGG ACAATCTGCA TATTTAAATG CCAATGTACG ATATA     1075
```

(2) INFORMATION FOR SEQ ID NO: 31:

(i) SEQUENCE CHARACTERISTICS:
        (A) LENGTH: 2645 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: PS177C8

(xi) SEQUENCE DESCRIPTION: SEQ ID NO: 31:

```
ATGAAGAAGA AGTTAGCAAG TGTTGTAACG TGTACGTTAT TAGCTCCTAT GTTTTTGAAT   60
GGAAATGTGA ATGCTGTTTA CGCAGACAGC AAAACAAATC AAATTTCTAC AACACAGAA   120
AATCAACAGA AAGAGATGGA CCGAAAAGGA TTACTTGGGT ATTATTTCAA AGGAAAAGA   180
TTTAGTAATC TTACTATGTT TGCACCGACA CGTGATAGTA CTCTTATTTA TGATCAACA   240
ACAGCAAATA AACTATTAGA TAAAAAACAA CAAGAATATC AGTCTATTCG TTGGATTGG   300
TTGATTCAGA GTAAAGAAAC GGGAGATTTC ACATTTAACT TATCTGAGGA TGAACAGGC   360
ATTATAGAAA TCAATGGGAA AATTATTTCT AATAAAGGGA AGAAAAGCA AGTTGTCCA   420
TTAGAAAAAG GAAAATTAGT TCCAATCAAA ATAGAGTATC AATCAGATAC AAAATTTAA   480
ATTGACAGTA AAACATTTAA AGAACTTAAA TTATTTAAAA TAGATAGTCA AAACCAACC   540
CAGCAAGTCC AGCAAGATGA ACTGAGAAAT CCTGAATTTA ACAAGAAAGA ATCACAGGA   600
TTCTTAGCGA AACCATCGAA ATAAATCTT TTCACTCAAA AAATGAAAAG GGAAATTGA   660
GAAGACACGG ATACGGATGG GGACTCTATT CCTGACCTTT GGGAAGAAAA TGGGTATAC   720
ATTCAAAATA GAATCGCTGT AAAGTGGGAC GATTCTYTAG CAAGTAAAGG GTATACGAA   780
TTTGTTTCAA ATCCGCTAGA AAGTCACACA GTTGGTGATC CTTATACAGA TTATGAAAA   840
GCAGCAAGAG ACCTAGATTT GTCAAATGCA AAGGAAACGT TAACCCATT GGTAGCTGC   900
TTTCCAAGTG TGAATGTTAG TATGGAAAAG GTGATATTAT CACCAAATGA AAATTTATC   960
AATAGTGTAG AGTCTCATTC ATCCACGAAT TGGTCTTATA CAAATACAGA AGGTGCTT  1020
GTTGAAGCGG GGATTGGACC AAAAGGTATT TCGTTCGGAG TTAGCGTAAA CTATCAAC  1080
TCTGAAACAG TTGCACAAGA ATGGGAACA TCTACAGGAA ATACTTCGCA ATTCAATA  1140
GCTTCAGCGG GATATTTAAA TGCAAATGTT CGATATAACA ATGTAGGAAC TGGTGCCA  1200
TACGATGTAA AACCTACAAC AAGTTTTGTA TTAAATAACG ATACTATCGC AACTATTA  1260
GCGAAATCTA ATTCTACAGC CTTAAATATA TCTCCTGGAG AAAGTTACCC GAAAAAAG  1320
CAAAATGGAA TCGCAATAAC ATCAATGGAT GATTTTAATT CCCATCCGAT TACATTAA  1380
AAAAAACAAG TAGATAATCT GCTAAATAAT AAACCTATGA TGTTGGAAAC AAACCAAA  1440
GATGGTGTTT ATAAGATAAA AGATACACAT GGAAATATAG TAACTGGCGG AGAATGGA  1500
GGTGTCATAC AACAAATCAA GGCTAAAACA GCGTCTATTA TTGTGGATGA TGGGGAAC  1560
GTAGCAGAAA AACGTGTAGC GGCAAAAGAT TATGAAAATC AGAAGATAA AACACCGT  1620
TTAACTTTAA AGATGCCCT GAAGCTTTCA TATCCAGATG AAATAAAAGA AATAGAGG  1680
TTATTATATT ATAAAAACAA ACCGATATAC GAATCGAGCG TTATGACTTA CTTAGATG  1740
AATACAGCAA AGAAGTGAC CAAACAATTA AATGATACCA CTGGGAAATT TAAAGATG  1800
AGTCATTTAT ATGATGTAAA ACTGACTCCA AAAATGAATG TTACAATCAA ATTGTCTA  1860
CTTTATGATA ATGCTGAGTC TAATGATAAC TCAATTGGTA AATGGACAAA CACAAATA  1920
GTTTCAGGTG AAATAACGG AAAAAAACAA TATTCTTCTA ATAATCCGGA TGCTAATT  1980
ACATTAAATA CAGATGCTCA AGAAAAATTA ATAAAAATC GTACTATTAT ATAAGTTT  2040
ATATGAAGTC AGAAAAAAAC ACACAATGTG AGATTACTAT AGATGGGGAG ATTTATCC  2100
TCACTACAAA AACAGTGAAT GTGAATAAAG ACAATTACAA AAGATTAGAT ATTATAGC  2160
ATAATATAAA AAGTAATCCA ATTTCTTCAA TTCATATTAA AACGAATGAT GAAATAAC  2220
TATTTTGGGA TGATATTTCT ATAACAGATG TAGCATCAAT AAAACCGGAA AATTTAAC  2280
ATTCAGAAAT TAAACAGATT TATAGTAGGT ATGGTATTAA GTTAGAAGAT GGAATCCT  2340
```

```
TTGATAAAAA AGGTGGGATT CATTATGGTG AATTTATTAA TGAAGCTAGT TTTAATAT       2400

AACCATTGCA AAATTATGTG ACAAAATATA AAGTTACTTA TAGTAGTGAG TTAGGACA       2460

ACGTGAGTGA CACACTTGAA AGTGATAAAA TTTACAAGGA TGGGACAATT AAATTTGA       2520

TTACAAAATA TAGTRAAAAT GAACAAGGAT TATTTTATGA CAGTGGATTA AATTGGGA       2580

TTAAAATTAA TGCTATTACT TATGATGGTA AAGAGATGAA TGTTTTTCAT AGATATAA       2640

AATAG                                                                 2645
```

(2) INFORMATION FOR SEQ ID NO: 32:

(i) SEQUENCE CHARACTERISTICS:
        (A) LENGTH: 881 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: PS177C8

(xi) SEQUENCE DESCRIPTION: SEQ ID NO: 32:

```
Met Lys Lys Leu Ala Ser Val Val Thr Cys Thr Leu Leu Ala Pr
1               5                  10                  15

Met Phe Leu Asn Gly Asn Val Asn Ala Val Tyr Ala Asp Ser Lys Th
            20                  25                  30

Asn Gln Ile Ser Thr Thr Gln Lys Asn Gln Gln Lys Glu Met Asp Ar
        35                  40                  45

Lys Gly Leu Leu Gly Tyr Tyr Phe Lys Gly Lys Asp Phe Ser Asn Le
50                  55                  60

Thr Met Phe Ala Pro Thr Arg Asp Ser Thr Leu Ile Tyr Asp Gln Gl
65                  70                  75                  80

Thr Ala Asn Lys Leu Leu Asp Lys Lys Gln Gln Glu Tyr Gln Ser Il
            85                  90                  95

Arg Trp Ile Gly Leu Ile Gln Ser Lys Glu Thr Gly Asp Phe Thr Ph
            100                 105                 110

Asn Leu Ser Glu Asp Glu Gln Ala Ile Ile Glu Ile Asn Gly Lys Il
        115                 120                 125

Ile Ser Asn Lys Gly Lys Glu Lys Gln Val Val His Leu Glu Lys Gl
130                 135                 140

Lys Leu Val Pro Ile Lys Ile Glu Tyr Gln Ser Asp Thr Lys Phe As
145                 150                 155                 160

Ile Asp Ser Lys Thr Phe Lys Glu Leu Lys Leu Phe Lys Ile Asp Se
            165                 170                 175

Gln Asn Gln Pro Gln Gln Val Gln Gln Asp Glu Leu Arg Asn Pro Gl
        180                 185                 190

Phe Asn Lys Lys Glu Ser Gln Glu Phe Leu Ala Lys Pro Ser Lys Il
        195                 200                 205

Asn Leu Phe Thr Gln Lys Met Lys Arg Glu Ile Asp Glu Asp Thr As
            210                 215                 220

Thr Asp Gly Asp Ser Ile Pro Asp Leu Trp Glu Glu Asn Gly Tyr Th
225                 230                 235                 240

Ile Gln Asn Arg Ile Ala Val Lys Trp Asp Asp Ser Leu Ala Ser Ly
            245                 250                 255

Gly Tyr Thr Lys Phe Val Ser Asn Pro Leu Glu Ser His Thr Val Gl
            260                 265                 270
```

```
Asp Pro Tyr Thr Asp Tyr Glu Lys Ala Ala Arg Asp Leu Asp Leu Se
        275                 280                 285
Asn Ala Lys Glu Thr Phe Asn Pro Leu Val Ala Phe Pro Ser Va
    290                 295                 300
Asn Val Ser Met Glu Lys Val Ile Leu Ser Pro Asn Glu Asn Leu Se
305                 310                 315                 320
Asn Ser Val Glu Ser His Ser Ser Thr Asn Trp Ser Tyr Thr Asn Th
                325                 330                 335
Glu Gly Ala Ser Val Glu Ala Gly Ile Gly Pro Lys Gly Ile Ser Ph
            340                 345                 350
Gly Val Ser Val Asn Tyr Gln His Ser Glu Thr Val Ala Gln Glu Tr
        355                 360                 365
Gly Thr Ser Thr Gly Asn Thr Ser Gln Phe Asn Thr Ala Ser Ala Gl
    370                 375                 380
Tyr Leu Asn Ala Asn Val Arg Tyr Asn Asn Val Gly Thr Gly Ala Il
385                 390                 395                 400
Tyr Asp Val Lys Pro Thr Thr Ser Phe Val Leu Asn Asn Asp Thr Il
                405                 410                 415
Ala Thr Ile Thr Ala Lys Ser Asn Ser Thr Ala Leu Asn Ile Ser Pr
            420                 425                 430
Gly Glu Ser Tyr Pro Lys Lys Gly Gln Asn Gly Ile Ala Ile Thr Se
        435                 440                 445
Met Asp Asp Phe Asn Ser His Pro Ile Thr Leu Asn Lys Lys Gln Va
    450                 455                 460
Asp Asn Leu Leu Asn Asn Lys Pro Met Met Leu Glu Thr Asn Gln Th
465                 470                 475                 480
Asp Gly Val Tyr Lys Ile Lys Asp Thr His Gly Asn Ile Val Thr Gl
                485                 490                 495
Gly Glu Trp Asn Gly Val Ile Gln Gln Ile Lys Ala Lys Thr Ala Se
            500                 505                 510
Ile Ile Val Asp Asp Gly Glu Arg Val Ala Glu Lys Arg Val Ala Al
        515                 520                 525
Lys Asp Tyr Glu Asn Pro Glu Asp Lys Thr Pro Ser Leu Thr Leu Ly
    530                 535                 540
Asp Ala Leu Lys Leu Ser Tyr Pro Asp Glu Ile Lys Glu Ile Glu Gl
545                 550                 555                 560
Leu Leu Tyr Tyr Lys Asn Lys Pro Ile Tyr Glu Ser Ser Val Met Th
                565                 570                 575
Tyr Leu Asp Glu Asn Thr Ala Lys Glu Val Thr Lys Gln Leu Asn As
            580                 585                 590
Thr Thr Gly Lys Phe Lys Asp Val Ser His Leu Tyr Asp Val Lys Le
        595                 600                 605
Thr Pro Lys Met Asn Val Thr Ile Lys Leu Ser Ile Leu Tyr Asp As
    610                 615                 620
Ala Glu Ser Asn Asp Asn Ser Ile Gly Lys Trp Thr Asn Thr Asn Il
625                 630                 635                 640
Val Ser Gly Gly Asn Asn Gly Lys Lys Gln Tyr Ser Ser Asn Asn Pr
                645                 650                 655
Asp Ala Asn Leu Thr Leu Asn Thr Asp Ala Gln Glu Lys Leu Asn Ly
            660                 665                 670
Asn Arg Asp Tyr Tyr Ile Ser Leu Tyr Met Lys Ser Glu Lys Asn Th
        675                 680                 685
```

```
        Gln Cys Glu Ile Thr Ile Asp Gly Glu Ile Tyr Pro Ile Thr Thr Ly
            690                 695                 700
        Thr Val Asn Val Asn Lys Asp Asn Tyr Lys Arg Leu Asp Ile Ile Al
        705                 710                 715                 720
        His Asn Ile Lys Ser Asn Pro Ile Ser Ser Ile His Ile Lys Thr As
                        725                 730                 735
        Asp Glu Ile Thr Leu Phe Trp Asp Asp Ile Ser Ile Thr Asp Val Al
                    740                 745                 750
        Ser Ile Lys Pro Glu Asn Leu Thr Asp Ser Glu Ile Lys Gln Ile Ty
                755                 760                 765
        Ser Arg Tyr Gly Ile Lys Leu Glu Asp Gly Ile Leu Ile Asp Lys Ly
            770                 775                 780
        Gly Gly Ile His Tyr Gly Glu Phe Ile Asn Glu Ala Ser Phe Asn Il
        785                 790                 795                 800
        Glu Pro Leu Gln Asn Tyr Val Thr Lys Tyr Lys Val Thr Tyr Ser Se
                        805                 810                 815
        Glu Leu Gly Gln Asn Val Ser Asp Thr Leu Glu Ser Asp Lys Ile Ty
                    820                 825                 830
        Lys Asp Gly Thr Ile Lys Phe Asp Phe Thr Lys Tyr Ser Xaa Asn Gl
                835                 840                 845
        Gln Gly Leu Phe Tyr Asp Ser Gly Leu Asn Trp Asp Phe Lys Ile As
            850                 855                 860
        Ala Ile Thr Tyr Asp Gly Lys Glu Met Asn Val Phe His Arg Tyr As
        865                 870                 875                 880
        Lys
```

(2) INFORMATION FOR SEQ ID NO: 33:

(i) SEQUENCE CHARACTERISTICS:
        (A) LENGTH: 1022 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 177I8

(xi) SEQUENCE DESCRIPTION: SEQ ID NO: 33:

```
TGGATTAATT GGGTATTATT TCAAAGGAAA AGATTTTAAT AATCTTACTA TGTTTGCACC60

GACACGTGAT AATACCCTTA TGTATGACCA ACAAACAGCG AATGCATTAT TAGATAAAA120

ACAACAAGAA TATCAGTCCA TTCGTTGGAT TGGTTTGATT CAGAGTAAAG AAACGGGCG180

TTTCACATTT AACTTATCAA AGGATGAACA GGCAATTATA GAAATCGATG GGAAAATCA240

TTCTAATAAA GGGAAAGAAA AGCAAGTTGT CCATTTAGAA AAAGAAAAAT TAGTTCCAA300

CAAAATAGAG TATCAATCAG ATACGAAATT TAATATTGAT AGTAAAACAT TTAAAGAAC360

TAAATTATTT AAAATAGATA GTCAAAACCA ATCTCAACAA GTTCAACTGA GAAACCCTG420

ATTTAACAAA AAGAATCAC AGGAATTTTT AGCAAAAGCA TCAAAAACAA ACCTTTTTA480

GCAAAAAATG AAAAGAGATA TTGATGAAGA TACGGATACA GATGGAGACT CCATTCCTG540

TCTTTGGGAA GAAATGGGT ACACGATTCA AAATAAAGTT GCTGTCAAAT GGGATGATT600

GCTAGCAAGT AAGGGATATA CAAAATTTGT TTCGAATCCA TTAGACAGCC ACACAGTTG660

CGATCCCTAT ACTGATTATG AAAAGGCCGC AAGGGATTTA GATTTATCAA ATGCAAAGG720

AACGTTCAAC CCATTGGTAG CTGCTTTYCC AAGTGTGAAT GTTAGTATGG AAAAGGTGA780
```

```
ATTATCACCA AATGAAAATT TATCCAATAG TGTAGAGTCT CATTCATCCA CGAATTGGT 840

TTATACGAAT ACAGAAGGAG CTTCCATTGA AGCTGGTGGC GGTCCATTAG GCCTTTCTT 900

TGGAGTGAGT GTTAATTATC AACACTCTGA AACAGTTGCA CAAGAATGGG GAACATCTA 960

AGGAAATACT TCACAATTCA ATACGGCTTC AGCGGGATAT TTAAATGCCA ATATACGA 1020

TA                                                              1022
```

(2) INFORMATION FOR SEQ ID NO: 34:

(i) SEQUENCE CHARACTERISTICS:
       (A) LENGTH: 340 amino acids
       (B) TYPE: amino acid
       (C) STRANDEDNESS: single
       (D) TOPOLOGY: linear (ii) MOLECULE TYPE: peptide (vi) ORIGINAL SOURCE:
      (C) INDIVIDUAL ISOLATE: 17718

(xi) SEQUENCE DESCRIPTION: SEQ ID NO: 34:

```
Gly Leu Ile Gly Tyr Tyr Phe Lys Gly Lys Asp Phe Asn Asn Leu Th
 1               5                  10                  15

Met Phe Ala Pro Thr Arg Asp Asn Thr Leu Met Tyr Asp Gln Gln Th
            20                  25                  30

Ala Asn Ala Leu Leu Asp Lys Lys Gln Gln Glu Tyr Gln Ser Ile Ar
        35                  40                  45

Trp Ile Gly Leu Ile Gln Ser Lys Glu Thr Gly Asp Phe Thr Phe As
    50                  55                  60

Leu Ser Lys Asp Glu Gln Ala Ile Ile Glu Ile Asp Gly Lys Ile Il
65                  70                  75                  80

Ser Asn Lys Gly Lys Glu Lys Gln Val Val His Leu Glu Lys Glu Ly
                85                  90                  95

Leu Val Pro Ile Lys Ile Glu Tyr Gln Ser Asp Thr Lys Phe Asn Il
            100                 105                 110

Asp Ser Lys Thr Phe Lys Glu Leu Lys Leu Phe Lys Ile Asp Ser Gl
        115                 120                 125

Asn Gln Ser Gln Gln Val Gln Leu Arg Asn Pro Glu Phe Asn Lys Ly
    130                 135                 140

Glu Ser Gln Glu Phe Leu Ala Lys Ala Ser Lys Thr Asn Leu Phe Ly
145                 150                 155                 160

Gln Lys Met Lys Arg Asp Ile Asp Glu Asp Thr Asp Thr Asp Gly As
                165                 170                 175

Ser Ile Pro Asp Leu Trp Glu Glu Asn Gly Tyr Thr Ile Gln Asn Ly
            180                 185                 190

Val Ala Val Lys Trp Asp Asp Ser Leu Ala Ser Lys Gly Tyr Thr Ly
        195                 200                 205

Phe Val Ser Asn Pro Leu Asp Ser His Thr Val Gly Asp Pro Tyr Th
    210                 215                 220

Asp Tyr Glu Lys Ala Ala Arg Asp Leu Asp Leu Ser Asn Ala Lys Gl
225                 230                 235                 240

Thr Phe Asn Pro Leu Val Ala Ala Xaa Pro Ser Val Asn Val Ser Me
                245                 250                 255

Glu Lys Val Ile Leu Ser Pro Asn Glu Asn Leu Ser Asn Ser Val Gl
            260                 265                 270

Ser His Ser Ser Thr Asn Trp Ser Tyr Thr Asn Thr Glu Gly Ala Se
```

```
            275                 280                    285

Ile Glu Ala Gly Gly Pro Leu Gly Leu Ser Phe Gly Val Se Va
            290                 295                300

Asn Tyr Gln His Ser Glu Thr Val Ala Gln Glu Trp Gly Thr Ser Th
        305                 310                 315                320

Gly Asn Thr Ser Gln Phe Asn Thr Ala Ser Ala Gly Tyr Leu Asn Al
                        325                 330                 335

Asn Ile Arg Tyr
                340
```

(2) INFORMATION FOR SEQ ID NO: 35:

(i) SEQUENCE CHARACTERISTICS:
      (A) LENGTH: 1073 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (C) INDIVIDUAL ISOLATE: 185AA2

(xi) SEQUENCE DESCRIPTION: SEQ ID NO: 35:

```
TGGATTAATT GGGTATTATT TCCAGGAGCA AAACTTTGAG AAACCCGCTT TGATAGCAAA 60

TAGACAAGCT TCTGATTTGG AAATACCGAA AGATGACGTG AAAGAGTTAC TATCCAAAG 120

ACAGCAACAC ATTCAATCTG TTAGATGGCT TGGCTATATT CAGCCACCTC AAACAGGAG 180

CTATGTATTG TCAACCTCAT CCGACCAACA GGTCGTGATT GAACTCGATG GAAAAACCA 240

TGTCAATCAA ACTTCTATGA CAGAACCGAT TCAACTAGAA AAAGATAAAC GCTATAAAA 300

TAGAATTGAA TATGTCCCAG GAGATACACA AGGACAAGAG AACCTTCTGG ACTTTCAAC 360

GAAGTGGTCA ATTTCAGGAG CCGAGATAGA ACCAATTCCG GATCATGCTT TCCATTTAC 420

AGATTTTTCT CATAAACAAG ATCAAGAGAA AATCATCCCT GAAACCAATT TATTTCAGA 480

ACAAGGAGAT GAGAAAAAAG TATCACGCAG TAAGAGATCT TCAGATAAAG ATCCTGACC 540

TGATACAGAT GATGATAGTA TTTCTGATGA ATGGGAAACG AGTGGATATA CCATTCAAA 600

ACAGGTGGCA GTGAAATGGG ACGATTCTAT GAAGGAGCTA GGTTATACCA AGTATGTGT 660

TAACCCTTAT AAGTCTCGTA CAGTAGGAGA TCCATACACA GATTGGGAAA AAGCGGCTG 720

CAGTATCGAT AATGCTGTCA AAGCAGAAGC CAGAAATCCT TTAGTCGCGG CCTATCCAA 780

TGTTGGTGTA CATATGGAAA GATTAATTGT CTCCGAACAA CAAAATATAT CAACAGGGC 840

TGGAAAAACC GTATCTGCGT CTACGTCCGC AAGCAATACC GCAGCGATTA CGGCAGGTA 900

TGATGCAACA GCTGGTGCCT CTTTACTTGG GCCATCTGGA AGTGTCACGG CTCATTTTT 960

TTACACGGGA TCTAGTACAG CCACCATTGA AGATAGCTCC AGCCGTAATT GGAGTCGA 1020

CCTTGGGATT GATACGGGAC AAGCTGCATA TTTAAATGCC AATATACGAT ATA      1073
```

(2) INFORMATION FOR SEQ ID NO: 36:

(i) SEQUENCE CHARACTERISTICS:
      (A) LENGTH: 357 amino acids
      (B) TYPE: amino acid
      (C) STRANDEDNESS: single
      (D) TOPOLOGY: linear (ii) MOLECULE TYPE: peptide (vi) ORIGINAL SOURCE:
      (C) INDIVIDUAL ISOLATE: 185AA2

(xi) SEQUENCE DESCRIPTION: SEQ ID NO: 36:

```
Gly Leu Ile Gly Tyr Tyr Phe Gln Glu Gln Asn Phe Glu Lys Pro Al
1               5                   10                  15

Leu Ile Ala Asn Arg Gln Ala Ser Asp Leu Glu Ile Pro Lys Asp As
            20                  25                  30

Val Lys Glu Leu Leu Ser Lys Glu Gln Gln His Ile Gln Ser Val Ar
        35                  40                  45

Trp Leu Gly Tyr Ile Gln Pro Pro Gln Thr Gly Asp Tyr Val Leu Se
    50                  55                  60

Thr Ser Ser Asp Gln Gln Val Val Ile Glu Leu Asp Gly Lys Thr Il
65                  70                  75                  80

Val Asn Gln Thr Ser Met Thr Glu Pro Ile Gln Leu Glu Lys Asp Ly
                85                  90                  95

Arg Tyr Lys Ile Arg Ile Glu Tyr Val Pro Gly Asp Thr Gln Gly Gl
            100                 105                 110

Glu Asn Leu Leu Asp Phe Gln Leu Lys Trp Ser Ile Ser Gly Ala Gl
        115                 120                 125

Ile Glu Pro Ile Pro Asp His Ala Phe His Leu Pro Asp Phe Ser Hi
    130                 135                 140

Lys Gln Asp Gln Glu Lys Ile Ile Pro Glu Thr Asn Leu Phe Gln Ly
145                 150                 155                 160

Gln Gly Asp Glu Lys Lys Val Ser Arg Ser Lys Arg Ser Ser Asp Ly
                165                 170                 175

Asp Pro Asp Arg Asp Thr Asp Asp Ser Ile Ser Asp Glu Trp Gl
            180                 185                 190

Thr Ser Gly Tyr Thr Ile Gln Arg Gln Val Ala Val Lys Trp Asp As
        195                 200                 205

Ser Met Lys Glu Leu Gly Tyr Thr Lys Tyr Val Ser Asn Pro Tyr Ly
    210                 215                 220

Ser Arg Thr Val Gly Asp Pro Tyr Thr Asp Trp Glu Lys Ala Ala Gl
225                 230                 235                 240

Ser Ile Asp Asn Ala Val Lys Ala Glu Ala Arg Asn Pro Leu Val Al
                245                 250                 255

Ala Tyr Pro Thr Val Gly Val His Met Glu Arg Leu Ile Val Ser Gl
            260                 265                 270

Gln Gln Asn Ile Ser Thr Gly Leu Gly Lys Thr Val Ser Ala Ser Th
        275                 280                 285

Ser Ala Ser Asn Thr Ala Ala Ile Thr Ala Gly Ile Asp Ala Thr Al
    290                 295                 300

Gly Ala Ser Leu Leu Gly Pro Ser Gly Ser Val Thr Ala His Phe Se
305                 310                 315                 320

Tyr Thr Gly Ser Ser Thr Ala Thr Ile Glu Asp Ser Ser Arg As
                325                 330                 335

Trp Ser Arg Asp Leu Gly Ile Asp Thr Gly Gln Ala Ala Tyr Leu As
            340                 345                 350

Ala Asn Ile Arg Tyr
            355
```

(2) INFORMATION FOR SEQ ID NO: 37:

(i) SEQUENCE CHARACTERISTICS:
        (A) LENGTH: 1073 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
         (C) INDIVIDUAL ISOLATE: 196F3

(xi) SEQUENCE DESCRIPTION: SEQ ID NO: 37:

TGGGTTACNT GGGTATTAYT TTCAGGATAC TAAATTTCAA CAACTTGCTT TAATGGCACA 60

TAGACAAGCC TCAGATTTAG AAATAAACAA AAATGAMGTC AAGGATTTAC TATCAAAGG 120

TCAACAACAC ATTCAAGCAG TGAGATGGAT GGGCTATATT CAGCCACCTC AAACAGGAG 180

TTATGTATTG TCAACTTCAT CCGACCAACA GGTCTTCACC GAACTCNATG GAAAAATAA 240

TCTCAATCAA TCTTCTATGA CCGAACCCAT TCGATTAGAA AAAGATAAAC AATATAMAA 300

TAGAATTGAA TATGTATCAK AAAGTAAAAC AGAAAAAGAG ACGCTCCTAG ACTTTCAAC 360

CAACTGGTCG ATTTCAGGTG CTACGGTAGA ACCAATTCCA GATAATGCTT TTCAGTTAC 420

AGATCTTTCT CGGGAACAAG NTAAAGATAA AATCATCCCT GAAACAAGTT TATTGCAGG 480

TCAAGGAGAA GGGAAACAAG TATCTCGAAG TAAAAGATCT CTAGCTGTGA ATCCTCTAC 540

CGATACAGAT GATGATGGGA TTTACGATGA ATGGGAAACA AGCGGCTATA CGATTCAAA 600

ACAATTGGCA GTAAGATGGA ACGATTCTAT GAAGGATCAA GGCTATACCA AATATGTGT 660

TAATCCTTAT AAGTCTCATA CTGTAGGAGA TCCATACACA GACTGGGAAA AAGCAGCTG 720

ACGTATCGAC CAAGCTGTGA AAATAGAAGC CAGAAACCCA TTAGTTGCAG CATATCCAA 780

AGTTGGCGTA CATATGGAAA GACTGATTGT CTCTGAAAAA CAAAATATAG CAACAGGAC 840

GGGAAAAACA GTATCTGCGT CTACATCTGC AAGTAATACA GCGGGGATTA CAGCGGGAA 900

CGATGCAACG GTTGGTGCCT CTTTACTTGG ACCTTCGGGA AGTGTCACCG CCCATTTTT 960

TTATACGGGT TCGAGTACAT CCACTGTTGA AAATAGCTCG AGTAATAATT GGAGTCAA 1020

TCTTGGTATT GATACCAGCC AATCTGCGTA CTTAAATGCC AATGTAAGAT ATA       1073

(2) INFORMATION FOR SEQ ID NO: 38:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
         (C) INDIVIDUAL ISOLATE: 196F3

(xi) SEQUENCE DESCRIPTION: SEQ ID NO: 38:

Gly Leu Xaa Gly Tyr Xaa Phe Gln Asp Thr Lys Phe Gln Gln Leu Al
        1               5                   10                  15

Leu Met Ala His Arg Gln Ala Ser Asp Leu Glu Ile Asn Lys Asn Xa
                        20                  25                  30

Val Lys Asp Leu Leu Ser Lys Asp Gln Gln His Ile Gln Ala Val Ar
                    35                  40                  45

Trp Met Gly Tyr Ile Gln Pro Pro Gln Thr Gly Asp Tyr Val Leu Se
                50                  55                  60

Thr Ser Ser Asp Gln Gln Val Phe Thr Glu Leu Xaa Gly Lys Ile Il
        65                  70                  75                  80

Leu Asn Gln Ser Ser Met Thr Glu Pro Ile Arg Leu Glu Lys Asp Ly
                        85                  90                  95

```
            Gln Tyr Xaa Ile Arg Ile Glu Tyr Val Ser Xaa Ser Lys Thr Glu Ly
                    100                 105                 110

Glu Thr Leu Leu Asp Phe Gln Leu Asn Trp Ser Ile Ser Gly Ala Th
                115                 120                 125

Val Glu Pro Ile Pro Asp Asn Ala Phe Gln Leu Pro Asp Leu Ser Ar
            130                 135                 140

Glu Gln Xaa Lys Asp Lys Ile Ile Pro Glu Thr Ser Leu Leu Gln As
            145                 150                 155                 160

Gln Gly Glu Gly Lys Gln Val Ser Arg Ser Lys Arg Ser Leu Ala Va
                                165                 170                 175

Asn Pro Leu His Asp Thr Asp Asp Gly Ile Tyr Asp Glu Trp Gl
                        180                 185                 190

Thr Ser Gly Tyr Thr Ile Gln Arg Gln Leu Ala Val Arg Trp Asn As
                    195                 200                 205

Ser Met Lys Asp Gln Gly Tyr Thr Lys Tyr Val Ser Asn Pro Tyr Ly
                210                 215                 220

Ser His Thr Val Gly Asp Pro Tyr Thr Asp Trp Glu Lys Ala Ala Gl
            225                 230                 235                 240

Arg Ile Asp Gln Ala Val Lys Ile Glu Ala Arg Asn Pro Leu Val Al
                                245                 250                 255

Ala Tyr Pro Thr Val Gly Val His Met Glu Arg Leu Ile Val Ser Gl
                        260                 265                 270

Lys Gln Asn Ile Ala Thr Gly Leu Gly Lys Thr Val Ser Ala Ser Th
                    275                 280                 285

Ser Ala Ser Asn Thr Ala Gly Ile Thr Ala Gly Ile Asp Ala Thr Va
                290                 295                 300

Gly Ala Ser Leu Leu Gly Pro Ser Gly Ser Val Thr Ala His Phe Se
            305                 310                 315                 320

Tyr Thr Gly Ser Ser Thr Ser Thr Val Glu Asn Ser Ser Ser Asn As
                                325                 330                 335

Trp Ser Gln Asp Leu Gly Ile Asp Thr Ser Gln Ser Ala Tyr Leu As
                        340                 345                 350

Ala Asn Val Arg Tyr
                        355

(2) INFORMATION FOR SEQ ID NO: 39:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (C) INDIVIDUAL ISOLATE: 196J4

(xi) SEQUENCE DESCRIPTION: SEQ ID NO: 39:

TGGGTTAATT GGGTATTATT TCCAGGATCA AAAGTTTCAA CAACTTGCTT TAATGGCACA 60

TAGACAAGCT TCTAATTTAA ACATACCAAA AAATGAAGTG AAACAGTTAT TATCCGAAG 120

TCAACAACAT ATTCAATCCG TTAGGTGGAT CGGATATATC AAATCACCTC AAACGGGAG 180

TTATATATTG TCAACTTCAG CCGATCGACA TGTCGTAATT GAACTTGACG GAAAAACCA 240

TCTTAATCAA TCTTCTATGA CAGCACCCAT TCAATTAGAA AAAGATAAAC TTTATAAAA 300

TAGAATTGAA TATGTCCCAG AAGATACAAA AGGACAGGAA AACCTCTTTG ACTTTCAAC 360
```

```
GAATTGGTCA ATTTCAGGAG ATAAGGTAGA ACCAATTCCG GAGAATGCAT TTCTGTTGC  420

AGACTTTTCT CATAAACAAG ATCAAGAGAA AATCATCCCT GAAGCAAGTT TATTCCAGG  480

ACAAGAAGAT GCAAACAAAG TCTCTCGAAA TAAACGATCC ATAGCTACAG GTTCTCTGT  540

TGATACAGAT GATGATGCTA TTTATGATGA ATGGGAAACA GAAGGATACA CGATACAAC  600

TCAAATAGCG GTGAAATGGG ACGATTCTAT GAAGGAGCGA GGTTATACCA AGTATGTGT  660

TAACCCCTAT AATTCGCATA CAGTAGGAGA TCCCTACACA GATTGGGAAA AAGCGGCTG  720

ACGCATTGAT CAGGCAATCA AGTAGAAGC TAGGAATCCA TTAGTTGCAG CCTATCCAA  780

AGTTGGTGTA CATATGGAAA AACTGATTGT TTCTGAGAAA CAAAATATAT CAACTGGGG  840

TGGAAAAACA GTATCTGCGG CTATGTCCAC TGGTAATACC GCAGCGATTA CGGCAGGAA  900

TGATGCGACC GCCGGGGCAT CTTTACTTGG ACCTTCTGGA AGTGTGACGG CTCATTTTT  960

TTATACAGGG TCTAGTACAT CTACAATTGA AATAGTTCA AGCAATAATT GGAGTAAA   1020

TCTGGGAATC GATACGGGGC AATCTGCTTA TTTAAATGCC AATGTACGAT ATA        1073
```

(2) INFORMATION FOR SEQ ID NO: 40:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 196J4

(xi) SEQUENCE DESCRIPTION: SEQ ID NO: 40:

```
Gly Leu Ile Gly Tyr Tyr Phe Gln Asp Gln Lys Phe Gln Gln Leu Al
  1               5                  10                  15

Leu Met Ala His Arg Gln Ala Ser Asn Leu Asn Ile Pro Lys Asn Gl
             20                  25                  30

Val Lys Gln Leu Leu Ser Glu Asp Gln His Ile Gln Ser Val Ar
         35                  40                  45

Trp Ile Gly Tyr Ile Lys Ser Pro Gln Thr Gly Asp Tyr Ile Leu Se
     50                  55                  60

Thr Ser Ala Asp Arg His Val Val Ile Glu Leu Asp Gly Lys Thr Il
 65                  70                  75                  80

Leu Asn Gln Ser Ser Met Thr Ala Pro Ile Gln Leu Glu Lys Asp Ly
             85                  90                  95

Leu Tyr Lys Ile Arg Ile Glu Tyr Val Pro Glu Asp Thr Lys Gly Gl
            100                 105                 110

Glu Asn Leu Phe Asp Phe Gln Leu Asn Trp Ser Ile Ser Gly Asp Ly
            115                 120                 125

Val Glu Pro Ile Pro Glu Asn Ala Phe Leu Leu Pro Asp Phe Ser Hi
            130                 135                 140

Lys Gln Asp Gln Glu Lys Ile Ile Pro Glu Ala Ser Leu Phe Gln Gl
145                 150                 155                 160

Gln Glu Asp Ala Asn Lys Val Ser Arg Asn Lys Arg Ser Ile Ala Th
                165                 170                 175

Gly Ser Leu Tyr Asp Thr Asp Asp Ala Ile Tyr Asp Glu Trp Gl
            180                 185                 190

Thr Glu Gly Tyr Thr Ile Gln Arg Gln Ile Ala Val Lys Trp Asp As
            195                 200                 205
```

```
Ser Met Lys Glu Arg Gly Tyr Thr Lys Tyr Val Ser Asn Pro Tyr As
    210                 215                 220

Ser His Thr Val Gly Asp Pro Tyr Thr Asp Trp Glu Lys Ala Ala Gl
225                 230                 235                 240

Arg Ile Asp Gln Ala Ile Lys Val Glu Ala Arg Asn Pro Leu Val Al
                245                 250                 255

Ala Tyr Pro Thr Val Gly Val His Met Glu Lys Leu Ile Val Ser Gl
            260                 265                 270

Lys Gln Asn Ile Ser Thr Gly Val Gly Lys Thr Val Ser Ala Ala Me
        275                 280                 285

Ser Thr Gly Asn Thr Ala Ala Ile Thr Ala Gly Ile Asp Ala Thr Al
    290                 295                 300

Gly Ala Ser Leu Leu Gly Pro Ser Gly Ser Val Thr Ala His Phe Se
305                 310                 315                 320

Tyr Thr Gly Ser Ser Thr Ser Thr Ile Glu Asn Ser Ser Ser Asn As
                325                 330                 335

Trp Ser Lys Asp Leu Gly Ile Asp Thr Gly Gln Ser Ala Tyr Leu As
            340                 345                 350

Ala Asn Val Arg Tyr
            355
```

(2) INFORMATION FOR SEQ ID NO: 41:

(i) SEQUENCE CHARACTERISTICS:
        (A) LENGTH: 1046 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 197T1

(xi) SEQUENCE DESCRIPTION: SEQ ID NO: 41:

```
TGGATTAATT GGGTATTATT TTAAAGGAAA AGATTTTAAT AATCTTACTA TATTTGCTCC60

AACACGTGAG AATACTCTTA TTTATGATTT AGAAACAGCG AATTCTTTAT TAGATAAGC120

ACAACAAACC TATCAATCTA TTCGTTGGAT CGGTTTAATA AAAAGCAAAA AAGCTGGAG180

TTTTACCTTT CAATTATCGG ATGATGAGCA TGCTATTATA GAAATCGATG GAAAGTTA240

TTCGCAAAAA GGCCAAAAGA AACAAGTTGT TCATTTAGAA AAAGATAAAT TAGTTCCCA300

CAAAATTGAA TATCAATCTG ATAAAGCGTT AAACCCAGAC AGTCAAATGT TTAAAGAAT360

GAAATTATTT AAAATAAATA GTCAAAAACA ATCTCAGCAA GTGCAACAAG ACGAATTGA420

AAATCCTGAA TTTGGTAAAG AAAAAACTCA ACATATTTA AGAAAGCAT CGAAAAGCA480

CTTGTTTAGC AATAAAAGTA AACGAGATAT AGATGAAGAT ATAGATGAGG ATACAGATA540

AGATGGAGAT GCCATTCCTG ATGTATGGGA AGAAAATGGG TATACCATCA AGGAAGAG600

AGCTGTTAAA TGGGACGAAG GATTAGCTGA TAAGGGATAT AAAAAGTTTG TTTCCAATC660

TTTTAGACAG CACACTGCTG GTGACCCCTA TAGTGACTAT GAAAAGGCAT CAAAAGATT720

GGATTTATCT AATGCAAAAG AAACATTTAA TCCATTGGTG GCTGCTTTTC CAAGTGTCA780

TGTTAGCTTG GAAAATGTCA CCATATCAAA AGATGAAAAT AAAACTGCTG AAATTGCGT840

TACTTCATCG AATAATTGGT CCTATACAAA TACAGAGGGG GCATCTATTG AAGCTGGAA900

TGGACCAGAA GGTTTGTTGT CTTTTGGAGT AAGTGCCAAT TATCAACATT CTGAAACAG960

GGCCAAAGAG TGGGGTACAA CTAAGGGAGA CGCAACACAA TATAATACAG CTTCAGCA1020
```

-continued

```
        ATATCTAAAT GCCAATGTAC GATATA                                1046
```

(2) INFORMATION FOR SEQ ID NO: 42:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 197T1

(xi) SEQUENCE DESCRIPTION: SEQ ID NO: 42:

```
Gly Leu Ile Gly Tyr Tyr Phe Lys Gly Lys Asp Phe Asn Asn Leu Th
1               5                   10                  15

Ile Phe Ala Pro Thr Arg Glu Asn Thr Leu Ile Tyr Asp Leu Glu Th
            20                  25                  30

Ala Asn Ser Leu Leu Asp Lys Gln Gln Gln Thr Tyr Gln Ser Ile Ar
        35                  40                  45

Trp Ile Gly Leu Ile Lys Ser Lys Lys Ala Gly Asp Phe Thr Phe Gl
    50                  55                  60

Leu Ser Asp Asp Glu His Ala Ile Ile Glu Ile Asp Gly Lys Val Il
65                  70                  75                  80

Ser Gln Lys Gly Gln Lys Gln Val Val His Leu Glu Lys Asp Ly
                85                  90                  95

Leu Val Pro Ile Lys Ile Glu Tyr Gln Ser Asp Lys Ala Leu Asn Pr
            100                 105                 110

Asp Ser Gln Met Phe Lys Glu Leu Lys Leu Phe Lys Ile Asn Ser Gl
        115                 120                 125

Lys Gln Ser Gln Gln Val Gln Gln Asp Glu Leu Arg Asn Pro Glu Ph
    130                 135                 140

Gly Lys Glu Lys Thr Gln Thr Tyr Leu Lys Lys Ala Ser Lys Ser Se
145                 150                 155                 160

Leu Phe Ser Asn Lys Ser Lys Arg Asp Ile Asp Glu Asp Ile Asp Gl
                165                 170                 175

Asp Thr Asp Thr Asp Gly Asp Ala Ile Pro Asp Val Trp Glu Glu As
            180                 185                 190

Gly Tyr Thr Ile Lys Gly Arg Val Ala Val Lys Trp Asp Glu Gly Le
        195                 200                 205

Ala Asp Lys Gly Tyr Lys Lys Phe Val Ser Asn Pro Phe Arg Gln Hi
    210                 215                 220

Thr Ala Gly Asp Pro Tyr Ser Asp Tyr Glu Lys Ala Ser Lys Asp Le
225                 230                 235                 240

Asp Leu Ser Asn Ala Lys Glu Thr Phe Asn Pro Leu Val Ala Ala Ph
                245                 250                 255

Pro Ser Val Asn Val Ser Leu Glu Asn Val Thr Ile Ser Lys Asp Gl
            260                 265                 270

Asn Lys Thr Ala Glu Ile Ala Ser Thr Ser Ser Asn Asn Trp Ser Ty
        275                 280                 285

Thr Asn Thr Glu Gly Ala Ser Ile Glu Ala Gly Ile Gly Pro Glu Gl
    290                 295                 300

Leu Leu Ser Phe Gly Val Ser Ala Asn Tyr Gln His Ser Glu Thr Va
305                 310                 315                 320
```

```
        Ala Lys Glu Trp Gly Thr Thr Lys Gly Asp Ala Thr Gln Tyr Asn Th
                        325                 330                 335

Ala Ser Ala Gly Tyr Leu Asn Ala Asn Val Arg Tyr
                        340                 345
```

(2) INFORMATION FOR SEQ ID NO: 43:

(i) SEQUENCE CHARACTERISTICS:
      (A) LENGTH: 1002 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (C) INDIVIDUAL ISOLATE: 197U2

(xi) SEQUENCE DESCRIPTION: SEQ ID NO: 43:

```
TGGGTTAATT GGGTATTATT TTACGGATGA GCAGCATAAG GAAGTAGCTT TTAYTCAATT  60

AGGTGAAAAA AMTACATTAG CAGATTCAGC GAAAATGAAG AAAAACGACA AAAAGATTC  120

TTCAGCGCAA TGGATTGGWA ATATACAGGT ACCTCAAACA GGGGAATATA CGTTTTCCA  180

CTCTTCTGAT AAAGATACTA TTTTAAAACT CAATGGGGAA ACGATTATTC AAAAATCTA  240

TATGGAGAAA CCCATATATT TAGAAAAAGA TAAAGTATAC GAAATTCAAA TCGAGCATA  300

CAACCCGAAT AGTGAGAAAA CTTTACGATT ATCTTGGAAA ATGGGGGGCA CCAATTCAG  360

GCTCATCCCA GAAAAATACA TTCTGTCTCC CGATTTTTCT AAAATAGCAG ATCAAGAAA  420

TGARAAAAAA GACGCATCGA GACATTTATT ATTTACTAAG GATGAATTGA AAGATTCTG  480

TAAGGACCTT ATCCCAGATG AATTTGAAAA AAATGGGTAT ACATTCAATG GGATTCAAA  540

TGTTCCTTGG GATGAATCTC TTCAAGAACA GGGCTTTAAA AAATATATTT CCAATCCAT  600

TCAATCGCGT ACAGCGCAGG ATCCATATAC AGATTTTGAA AAAGTAACCG GATATATGC  660

TGCCGAAACA CAACTGGAAA CGCGTGACCC TTTAGTTGCG GCTTATCCGG CTGTAGGG   720

TACGATGGAA CAGTTTATTT TCTCTAAAAA TGATAATGTG CAGGAATCTA ATGGTGGAG  780

AACTTCAAAA AGTATGACAG AAAGTTCTGA AACGACTTAC TCTGTTGAGA TAGGAGGGA  840

ATTTACATTG AATCCATTCG CACTGGCGGA AATTTCTCCT AAATATTCTC ACAGTTGGA  900

AAATGGAGCA TCTACAACAG AGGGAGAAAG TACTTCCTGG AGCTCACAAA TTGGTATTA  960

CACGGCTGAA CGCGCGTTTT TTAAATGCCA ATATTCGATA TA                   1002
```

(2) INFORMATION FOR SEQ ID NO: 44:

(i) SEQUENCE CHARACTERISTICS:
      (A) LENGTH: 333 amino acids
      (B) TYPE: amino acid
      (C) STRANDEDNESS: single
      (D) TOPOLOGY: linear (ii) MOLECULE TYPE: peptide (vi) ORIGINAL SOURCE:
      (C) INDIVIDUAL ISOLATE: 197U2

(xi) SEQUENCE DESCRIPTION: SEQ ID NO: 44:

```
        Gly Leu Ile Gly Tyr Tyr Phe Thr Asp Glu Gln His Lys Glu Val Al
        1               5                   10                  15

Phe Xaa Gln Leu Gly Glu Lys Xaa Thr Leu Ala Asp Ser Ala Lys Me
                        20                  25                  30

Lys Lys Asn Asp Lys Lys Ile Leu Ser Ala Gln Trp Ile Xaa Asn Il
```

|  |  |  |  | 35 |  |  |  | 40 |  |  |  | 45 |  |
|---|---|---|---|---|---|---|---|---|---|---|---|---|---|
| Gln | Val | Pro | Gln | Thr | Gly | Glu | Tyr | Thr | Phe | Ser | Thr | Ser | Asp Ly |
|  |  |  | 50 |  |  |  | 55 |  |  |  | 60 |  |  |
| Asp | Thr | Ile | Leu | Lys | Leu | Asn | Gly | Glu | Thr | Ile | Ile | Gln | Lys Ser As |
| 65 |  |  |  | 70 |  |  |  | 75 |  |  |  |  | 80 |
| Met | Glu | Lys | Pro | Ile | Tyr | Leu | Glu | Lys | Asp | Lys | Val | Tyr | Glu Ile Gl |
|  |  |  |  | 85 |  |  |  | 90 |  |  |  | 95 |  |
| Ile | Glu | His | Asn | Asn | Pro | Asn | Ser | Glu | Lys | Thr | Leu | Arg | Leu Ser Tr |
|  |  |  | 100 |  |  |  | 105 |  |  |  | 110 |  |  |
| Lys | Met | Gly | Gly | Thr | Asn | Ser | Glu | Leu | Ile | Pro | Glu | Lys | Tyr Ile Le |
|  |  | 115 |  |  |  | 120 |  |  |  | 125 |  |  |  |
| Ser | Pro | Asp | Phe | Ser | Lys | Ile | Ala | Asp | Gln | Glu | Asn | Xaa | Lys Lys As |
|  | 130 |  |  |  | 135 |  |  |  | 140 |  |  |  |  |
| Ala | Ser | Arg | His | Leu | Leu | Phe | Thr | Lys | Asp | Glu | Leu | Lys | Asp Ser As |
| 145 |  |  |  | 150 |  |  |  | 155 |  |  |  |  | 160 |
| Lys | Asp | Leu | Ile | Pro | Asp | Glu | Phe | Glu | Lys | Asn | Gly | Tyr | Thr Phe As |
|  |  |  |  | 165 |  |  |  | 170 |  |  |  | 175 |  |
| Gly | Ile | Gln | Ile | Val | Pro | Trp | Asp | Glu | Ser | Leu | Gln | Glu | Gln Gly Ph |
|  |  |  | 180 |  |  |  | 185 |  |  |  | 190 |  |  |
| Lys | Lys | Tyr | Ile | Ser | Asn | Pro | Tyr | Gln | Ser | Arg | Thr | Ala | Gln Asp Pr |
|  |  | 195 |  |  |  | 200 |  |  |  | 205 |  |  |  |
| Tyr | Thr | Asp | Phe | Glu | Lys | Val | Thr | Gly | Tyr | Met | Pro | Ala | Glu Thr Gl |
|  | 210 |  |  |  | 215 |  |  |  | 220 |  |  |  |  |
| Leu | Glu | Thr | Arg | Asp | Pro | Leu | Val | Ala | Ala | Tyr | Pro | Ala | Val Gly Va |
| 225 |  |  |  | 230 |  |  |  | 235 |  |  |  |  | 240 |
| Thr | Met | Glu | Gln | Phe | Ile | Phe | Ser | Lys | Asn | Asp | Asn | Val | Gln Glu Se |
|  |  |  |  | 245 |  |  |  | 250 |  |  |  | 255 |  |
| Asn | Gly | Gly | Gly | Thr | Ser | Lys | Ser | Met | Thr | Glu | Ser | Ser | Glu Thr Th |
|  |  |  | 260 |  |  |  | 265 |  |  |  | 270 |  |  |
| Tyr | Ser | Val | Glu | Ile | Gly | Gly | Lys | Phe | Thr | Leu | Asn | Pro | Phe Ala Le |
|  |  | 275 |  |  |  | 280 |  |  |  | 285 |  |  |  |
| Ala | Glu | Ile | Ser | Pro | Lys | Tyr | Ser | His | Ser | Trp | Lys | Asn | Gly Ala Se |
|  | 290 |  |  |  | 295 |  |  |  | 300 |  |  |  |  |
| Thr | Thr | Glu | Gly | Glu | Ser | Thr | Ser | Trp | Ser | Ser | Gln | Ile | Gly Ile As |
| 305 |  |  |  | 310 |  |  |  | 315 |  |  |  |  | 320 |
| Thr | Ala | Glu | Arg | Ala | Phe | Phe | Lys | Cys | Gln | Tyr | Ser | Ile |  |
|  |  |  |  | 325 |  |  |  | 330 |  |  |  |  |  |

(2) INFORMATION FOR SEQ ID NO: 45:

(i) SEQUENCE CHARACTERISTICS:
    (A) LENGTH: 1073 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (C) INDIVIDUAL ISOLATE: 202E1

(xi) SEQUENCE DESCRIPTION: SEQ ID NO: 45:

TGGGTTAATT GGGTACTATT TTCAGGATCA AAAGTTTCAA CAACTCGCTT TGATGGCACA 60

TAGACAAGCT TCAGATTTAG AAATACCTAA AAATGAAGTG AAGGATATAT TATCTAAAG 120

TCAACAACAT ATTCAATCAG TGAGATGGAG GGGGTATATT AAGCCACCTC AAACAGGAG 180

CTATATATTG TCAACCTCAT CCGACCAACA GGTCGTGATT GAACTCGATG GAAAAAACA 240

-continued

```
TGTCAATCAA ACTTCTATGA CAGAACCAAT TCAACTCGAA AAAGATAAAC TCTATAAAA 300

TAGAATTGAA TATGTCCCAG GAGATACAAA AGGACAAGAG AGCCTCCTTG ACTTTCAAC 360

TAACTGGTCA ATTTCAGGAG ATACGGTGGA ACCAATTCCG GAGAATGCAT TTCTGTTAC 420

AGACTTTTCT CATCAACAAG ATCAAGAGAA ACTCATCCCT GAAATCAGTC TATTTCAGG 480

ACAAGGAGAT GAGAAAAAAG TATCTCGTAG TAAGAGGTCT TTAGCTACAA ACCCTCTCC 540

TGATACAGAT GATGATGGTA TTTATGATGA ATGGGAAACG GAAGGATACA CAATACAGG 600

ACAACTAGCG GTGAAATGGG ACGATTCTAT GAAGGAGCGA GGTTATACTA AGTATGTGT 660

TAACCCTTAC AAGGCTCATA CAGTAGGAGA TCCCTACACA GATTGGGAAA AAGCGGCTG 720

CCGTATCGAT AACGCTGTCA AAGCAGAAGC TAGGAATCCT TTAGTCGCGG CCTATCCAA 780

TGTTGGTGTA CATATGGAAA GACTAATTGT CTCCGAAAAA CAAAATATAT CAACAGGAC 840

TGGAAAAACC GTATCTGTGT CTATGTCCGC AAGCAATACC GCAGCGATTA CGGCAGGAA 900

TAATGCAACA GCCGGTGCCT CTTTACTTGG GCCATCTGGA AACGTCACGG CTCATTTTT 960

TTATACAGGA TCTAGTACAT CCACTGTTGA AAATAGCTCA AGTAATAATT GGAGTCAA 1020

TCTTGGAATC GATACGGGAC AATCTGCGTA TTTAAATGCC AATGTAAGAT ATA        1073
```

(2) INFORMATION FOR SEQ ID NO: 46:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 202E1

(xi) SEQUENCE DESCRIPTION: SEQ ID NO: 46:

```
    Gly Leu Ile Gly Tyr Tyr Phe Gln Asp Gln Lys Phe Gln Gln Leu Al
    1               5                   10                  15

Leu Met Ala His Arg Gln Ala Ser Asp Leu Glu Ile Pro Lys Asn Gl
                    20                  25                  30

Val Lys Asp Ile Leu Ser Lys Asp Gln Gln His Ile Gln Ser Val Ar
                35                  40                  45

Trp Arg Gly Tyr Ile Lys Pro Pro Gln Thr Gly Asp Tyr Ile Leu Se
        50                  55                      60

Thr Ser Ser Asp Gln Gln Val Ile Glu Leu Asp Gly Lys Asn Il
    65                  70                  75                  80

Val Asn Gln Thr Ser Met Thr Glu Pro Ile Gln Leu Glu Lys Asp Ly
                    85                  90                  95

Leu Tyr Lys Ile Arg Ile Glu Tyr Val Pro Gly Asp Thr Lys Gly Gl
                100                 105                 110

Glu Ser Leu Leu Asp Phe Gln Leu Asn Trp Ser Ile Ser Gly Asp Th
                115                 120                 125

Val Glu Pro Ile Pro Glu Asn Ala Phe Leu Leu Pro Asp Phe Ser Hi
                130                 135                 140

Gln Gln Asp Gln Glu Lys Leu Ile Pro Gly Ile Ser Leu Phe Gln Gl
    145                 150                 155                 160

Gln Gly Asp Glu Lys Lys Val Ser Arg Ser Lys Arg Ser Leu Ala Th
                    165                 170                 175

Asn Pro Leu Leu Asp Thr Asp Asp Gly Ile Tyr Asp Glu Trp Gl
```

```
                    180                 185                 190
        Thr Glu Gly Tyr Thr Ile Gln Gly Gln Leu Ala Val Lys Trp Asp As
                195                 200                 205
        Ser Met Lys Glu Arg Gly Tyr Thr Lys Tyr Val Ser Asn Pro Tyr Ly
            210                 215                 220
        Ala His Thr Val Gly Asp Pro Tyr Thr Asp Trp Glu Lys Ala Ala Gl
        225                 230                 235                 240
        Arg Ile Asp Asn Ala Val Lys Ala Glu Ala Arg Asn Pro Leu Val Al
                        245                 250                 255
        Ala Tyr Pro Thr Val Gly Val His Met Glu Arg Leu Ile Val Ser Gl
                    260                 265                 270
        Lys Gln Asn Ile Ser Thr Gly Leu Gly Lys Thr Val Ser Val Ser Me
                275                 280                 285
        Ser Ala Ser Asn Thr Ala Ala Ile Thr Ala Gly Ile Asn Ala Thr Al
            290                 295                 300
        Gly Ala Ser Leu Leu Gly Pro Ser Gly Asn Val Thr Ala His Phe Se
        305                 310                 315                 320
        Tyr Thr Gly Ser Ser Thr Ser Thr Val Glu Asn Ser Ser Ser Asn As
                        325                 330                 335
        Trp Ser Gln Asp Leu Gly Ile Asp Thr Gly Gln Ser Ala Tyr Leu As
                    340                 345                 350
        Ala Asn Val Arg Tyr
                    355
```

(2) INFORMATION FOR SEQ ID NO: 47:

(i) SEQUENCE CHARACTERISTICS:
        (A) LENGTH: 967 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: KB33

(xi) SEQUENCE DESCRIPTION: SEQ ID NO: 47:

```
TGGATTACTT GGGTACTATT TTGAAGAACC AAACTTTAAT GACCTTCTAT TAATCACACA 60

AAAAAACAAC AGTAATTTAT CTCTAGAAAA AGAACATATT TCATCGTTAT CTAGTATTA 120

AAATAAAGGC ATTCAATCTG CTAGATGGTT AGGTTTTTTA AAACCAAAGC AAACGGATG 180

ATATGTTTTT TTTAGTCCTT CCAACCATGA AATCATGATT CAAATCGATA ACAAAATTA 240

TGTAATGGGT AGAAAAATTA TGTTAGAAGA AGGAAAGGTA TATCCAATTC GAATTGAAT 300

CCGCTTTGAA AAAACAAATA ATCTAGATAT AAACTGCGAA CTACTTTGGA CGCATTCTG 360

TACAAAAGAA ATCATTTCTC AAAACTGTTT GCTGGCACCT GATTATCATA ATACAGAAT 420

TTACCCAAAA ACAAATTTAT TTGGGGATGT ATCTACTACG ACTAGTGATA CTGATAATG 480

TGGAATACCA GATGACTGGG AAATTAATGG TTATACGTTT GATGGTACAA ATATAATTC 540

ATGGAATCCT GCTTATGAAG GGTTATATAC TAAATATATT TCTAACCCTA ACAAGCAA 600

TACAGTAGGT GATCCATATA CAGATTTAGA GAACGTMCAA AGCTAAAKGG ATCAAAGAA 660

CARGAAAYCC TTKTAGCAGA AGCTWATCCG AAAAATTGGA BTTAGCATGG AAGAATTAC 720

CRTCTCTKTA WAARTGKTGA TKTWTTCAAA TGCTCAAGAA AATKACTACT TACTTCTAG 780

AGRACAGAAG GCACTTCASG TAGYGCAGGC ATTGAGGGAG GAGCAGAAGG AAAAAAACC 840
```

ACAGGATTGG TTTCAGCCTC CTTTTCGCAT TCATCTTCAA CAACAAACAC AACGGAACA 900

ATGAATGGAA CAATGATTCA TCTTGATACA GGAGAATCAG CGTATTTAAA TGCCAATGT 960

AGATATA 967

(2) INFORMATION FOR SEQ ID NO: 48:

(i) SEQUENCE CHARACTERISTICS:
      (A) LENGTH: 972 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (C) INDIVIDUAL ISOLATE: KB38

(xi) SEQUENCE DESCRIPTION: SEQ ID NO: 48:

TGGATTACTT GGGTATTATT TTGAAGAACC AAACTTTAAT AACCTTCTAT TAATCACACA 60

AAAAAACAAC AGTAATTTAT CTCTAGAAAA AGAACATATT TCATCGTTAT CTAGTATTA 120

AAATAAAGGC ATTCAATCTG CTAGATGGTT AGGTTTTTTA AAACCAGAGC AAACGGATG 180

ATATGTTTTT TTTAGTCCTT CCAACCATGA AATTATGATT CAAATCGATA ACAAAATTA 240

TGTAATGGGT AGAAAAATTA TGTTAGAAAA AGGAAAGGTA TATCCAATTC GAATTGAAT 300

CCGCTTTGAA AAAACAAATA ATATAGATAT AAACTGCGAA CTACTTTGGA CGCACTCTG 360

TACAAAAGAA ATCATTTCTC AAAACTTTTT GCTGGCACCT GATTATAACA ATACAGAAT 420

TTATCCAAAA ACAAATTTAT TTGGAGATGT ATCTACTACG ACTWAGTGAT ACTGATAAT 480

ATGGAATACC AGATGACTGG GAAATTAATG GTTATACCTT TGATGGTACA AATATAATT 540

AGTGGAATTC TGCTTATGAA GGGTTATATA CTAAATATGT TTCTAATCCT AAACAAGCA 600

GTACAGTAGG TGATCCATAT ACAGATTTAG AGAAAGTAAC AGCTCAAATG GATCGAGCA 660

CCTCTCTAGA AGCAAGGAAT CCTTTAGTAG CAGCTTATCC AAAAATTGGA GTTAGCATG 720

AAGAATTACT CATCTCTTTA AATGTTGATT TTTCAAATGC TCAAGAAAAT ACTACTTCT 780

CTAGTAGAAC AGAAGGCACT TCACGTAGCG CAGGCATTGA GGGAGGAGCA GAAGGAAAA 840

AACCTACAGG ATTGGTTTCA GCCTCCTTTT CGCATTCATC TTCAACAACA AACACAACG 900

AACAAATGAA TGGAACAATG ATTCATCTTG ATACAGGAGA ATCAGCGTAT TTAAATGCC 960

ATGTAAGATA TA 972

(2) INFORMATION FOR SEQ ID NO: 49:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 49:

CTTGAYTTTA AARATGATRT A 21

(2) INFORMATION FOR SEQ ID NO: 50:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 50:

AATRGCSWAT AAATAMGCAC C                                        21

(2) INFORMATION FOR SEQ ID NO: 51:

(i) SEQUENCE CHARACTERISTICS:
       (A) LENGTH: 1341 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (C) INDIVIDUAL ISOLATE: PS177C8

(xi) SEQUENCE DESCRIPTION: SEQ ID NO: 51:

ATGTTTATGG TTTCTAAAAA ATTACAAGTA GTTACTAAAA CTGTATTGCT TAGTACAGTT60

TTCTCTATAT CTTTATTAAA TAATGAAGTG ATAAAAGCTG AACAATTAAA TATAAATTC120

CAAAGTAAAT ATACTAACTT GCAAAATCTA AAAATCACTG ACAAGGTAGA GGATTTTAA180

GAAGATAAGG AAAAAGCGAA AGAATGGGGG AAAGAAAAAG AAAAAGAGTG GAAACTAAC240

GCTACTGAAA AAGGAAAAAT GAATAATTTT TTAGATAATA AAAATGATAT AAAGACAAA300

TATAAAGAAA TTACTTTTTC TATGGCAGGC TCATTTGAAG ATGAAATAAA AGATTTAAA360

GAAATTGATA AGATGTTTGA TAAAACCAAT CTATCAAATT CTATTATCAC CTATAAAAA420

GTGGAACCGA CAACAATTGG ATTTAATAAA TCTTTAACAG AAGGTAATAC GATTAATTC480

GATGCAATGG CACAGTTTAA AGAACAATTT TTAGATAGGG ATATTAAGTT TGATAGTTA540

CTAGATACGC ATTTAACTGC TCAACAAGTT TCCAGTAAAA AAAGAGTTAT TTTGAAGGT600

ACGGTTCCGA GTGGGAAAGG TTCTACTACT CCAACAAAAG CAGGTGTCAT TTTAAATAA660

AGTGAATACA AAATGCTCAT TGATAATGGG TATATGGTCC ATGTAGATAA GGTATCAAA720

GTGGTGAAAA AAGGGGTGGA GTGCTTACAA ATTGAAGGGA CTTTAAAAAA GAGTCTTGA780

TTTAAAAATG ATATAAATGC TGAAGCGCAT AGCTGGGGTA TGAAGAATTA TGAAGAGTG840

GCTAAAGATT TAACCGATTC GCAAAGGGAA GCTTTAGATG GGTATGCTAG GCAAGATTA900

AAAGAAATCA ATAATTATTT AAGAAATCAA GGCGGAAGTG GAAATGAAAA ACTAGATGC960

CAAATAAAAA ATATTTCTGA TGCTTTAGGG AAGAAACCAA TACCGGAAAA TATTACTG1020

TATAGATGGT GTGGCATGCC GGAATTTGGT TATCAAATTA GTGATCCGTT ACCTTCTT1080

AAAGATTTTG AAGAACAATT TTTAAATACA ATCAAAGAAG ACAAAGGATA TATGAGTA1140

AGCTTATCGA GTGAACGTCT TGCAGCTTTT GGATCTAGAA AAATTATATT ACGATTAC1200

GTTCCGAAAG GAAGTACGGG TGCGTATTTA AGTGCCATTG GTGGATTTGC AAGTGAAA1260

GAGATCCTAC TTGATAAAGA TAGTAAATAT CATATTGATA AGTAACAGA GGTAATTA1320

AAGGTGTTAA GCGATATGTA G                                      1341

(2) INFORMATION FOR SEQ ID NO: 52:

(i) SEQUENCE CHARACTERISTICS:
       (A) LENGTH: 446 amino acids
       (B) TYPE: amino acid
       (C) STRANDEDNESS: single
       (D) TOPOLOGY: linear (ii) MOLECULE TYPE: peptide -continued (vi) ORIGINAL SOURCE:
    (C) INDIVIDUAL ISOLATE: PS177C8

(xi) SEQUENCE DESCRIPTION: SEQ ID NO: 52:

Met Phe Met Val Ser Lys Lys Leu Gln Val Val Thr Lys Thr Val Le
1               5                   10                  15

Leu Ser Thr Val Phe Ser Ile Ser Leu Leu Asn Asn Glu Val Ile Ly
            20                  25                  30

Ala Glu Gln Leu Asn Ile Asn Ser Gln Ser Lys Tyr Thr Asn Leu Gl
        35                  40                  45

Asn Leu Lys Ile Thr Asp Lys Val Glu Asp Phe Lys Glu Asp Lys Gl
    50                  55                  60

Lys Ala Lys Glu Trp Gly Lys Glu Lys Glu Trp Lys Leu Th
65                  70                  75              80

Ala Thr Glu Lys Gly Lys Met Asn Asn Phe Leu Asp Asn Lys Asn As
                85                  90                  95

Ile Lys Thr Asn Tyr Lys Glu Ile Thr Phe Ser Met Ala Gly Ser Ph
            100                 105                 110

Glu Asp Glu Ile Lys Asp Leu Lys Glu Ile Asp Lys Met Phe Asp Ly
        115                 120                 125

Thr Asn Leu Ser Asn Ser Ile Ile Thr Tyr Lys Asn Val Glu Pro Th
    130                 135                 140

Thr Ile Gly Phe Asn Lys Ser Leu Thr Glu Gly Asn Thr Ile Asn Se
145                 150                 155                 160

Asp Ala Met Ala Gln Phe Lys Glu Gln Phe Leu Asp Arg Asp Ile Ly
                165                 170                 175

Phe Asp Ser Tyr Leu Asp Thr His Leu Thr Ala Gln Val Ser Se
            180                 185                 190

Lys Glu Arg Val Ile Leu Lys Val Thr Val Pro Ser Gly Lys Gly Se
        195                 200                 205

Thr Thr Pro Thr Lys Ala Gly Val Ile Leu Asn Asn Ser Glu Tyr Ly
    210                 215                 220

Met Leu Ile Asp Asn Gly Tyr Met Val His Val Asp Lys Val Ser Ly
225                 230                 235                 240

Val Val Lys Lys Gly Val Glu Cys Leu Gln Ile Glu Gly Thr Leu Ly
                245                 250                 255

Lys Ser Leu Asp Phe Lys Asn Asp Ile Asn Ala Glu Ala His Ser Tr
            260                 265                 270

Gly Met Lys Asn Tyr Glu Glu Trp Ala Lys Asp Leu Thr Asp Ser Gl
        275                 280                 285

Arg Glu Ala Leu Asp Gly Tyr Ala Arg Gln Asp Tyr Lys Glu Ile As
    290                 295                 300

Asn Tyr Leu Arg Asn Gln Gly Gly Ser Gly Asn Glu Lys Leu Asp Al
305                 310                 315                 320

Gln Ile Lys Asn Ile Ser Asp Ala Leu Gly Lys Lys Pro Ile Pro Gl
                325                 330                 335

Asn Ile Thr Val Tyr Arg Trp Cys Gly Met Pro Glu Phe Gly Tyr Gl
            340                 345                 350

Ile Ser Asp Pro Leu Pro Ser Leu Lys Asp Phe Glu Glu Gln Phe Le
        355                 360                 365

Asn Thr Ile Lys Glu Asp Lys Gly Tyr Met Ser Thr Ser Leu Ser Se
    370                 375                 380

Glu Arg Leu Ala Ala Phe Gly Ser Arg Lys Ile Ile Leu Arg Leu Gl

```
            385                 390                 395                 400
        Val Pro Lys Gly Ser Thr Gly Ala Tyr Leu Ser Ala Ile Gly Gly Ph
                        405                 410                 415

Ala Ser Glu Lys Glu Ile Leu Leu Asp Lys Asp Ser Lys Tyr His Il
                        420                 425                 430

Asp Lys Val Thr Glu Val Ile Ile Lys Val Leu Ser Asp Met
                        435                 440                 445
```

(2) INFORMATION FOR SEQ ID NO: 53:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 53:

GGATTCGTTA TCAGAAA                                           17

(2) INFORMATION FOR SEQ ID NO: 54:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 54:

CTGTYGCTAA CAATGTC                                           17

(2) INFORMATION FOR SEQ ID NO: 55:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 55:

```
        Ala Asp Glu Pro Phe Asn Ala Asp
        1                 5
```

(2) INFORMATION FOR SEQ ID NO: 56:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 56:

GCTGATGAAC CATTTAATGC C                                    21

(2) INFORMATION FOR SEQ ID NO: 57:

(i) SEQUENCE CHARACTERISTICS:
      (A) LENGTH: 8 amino acids
      (B) TYPE: amino acid
      (C) STRANDEDNESS: single (D) TOPOLOGY: linear (ii) MOLECULE TYPE: peptide (xi) SEQUENCE DESCRIPTION: SEQ ID NO: 57:

Leu Phe Lys Val Asp Thr Lys Gln
        1               5

(2) INFORMATION FOR SEQ ID NO: 58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

CTCTTTAAAG TAGATACTAA GC                                              22

(2) INFORMATION FOR SEQ ID NO: 59:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

Pro Asp Glu Asn Leu Ser Asn Ile Glu
        1               5

(2) INFORMATION FOR SEQ ID NO: 60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

GATGAGAACT TATCAAATAG TATC                                            24

(2) INFORMATION FOR SEQ ID NO: 61:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

Ala Asn Ser Leu Leu Asp Lys Gln Gln Gln Thr Tyr
        1               5                   10

(2) INFORMATION FOR SEQ ID NO: 62:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

CGAATTCTTT ATTAGATAAG CAACAACAAA CCT                              33

(2) INFORMATION FOR SEQ ID NO: 63:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 63:

Val Ile Ser Gln Lys Gly Gln Lys
            1               5

(2) INFORMATION FOR SEQ ID NO: 64:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 64:

GTTATTTCGC AAAAAGGCCA AAAG                                        24

(2) INFORMATION FOR SEQ ID NO: 65:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 65:

Glu Tyr Gln Ser Asp Lys Ala Leu Asn Pro Asp
            1               5                   10

(2) INFORMATION FOR SEQ ID NO: 66:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 66:

GAATATCAAT CTGATAAAGC GTTAAACCCA G                                31

(2) INFORMATION FOR SEQ ID NO: 67:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 67:

Ser Ser Leu Phe Ser Asn Lys Ser Lys
1               5

(2) INFORMATION FOR SEQ ID NO: 68:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 68:

GCAGCYTGTT TAGCAATAAA AGT    23

(2) INFORMATION FOR SEQ ID NO: 69:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 69:

Ile Lys Gly Arg Val Ala Val Lys
1               5

(2) INFORMATION FOR SEQ ID NO: 70:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 70:

CAAAGGAAGA GTAGCTGTTA    20

(2) INFORMATION FOR SEQ ID NO: 71:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 71:

Val Asn Val Ser Leu Glu Asn Val Thr
1               5

(2) INFORMATION FOR SEQ ID NO: 72:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 72:

CAATGTTAGC TTGGAAAATG TCACC                                         25

(2) INFORMATION FOR SEQ ID NO: 73:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 73:

Thr Ala Phe Ile Gln Val Gly Glu
      1               5

(2) INFORMATION FOR SEQ ID NO: 74:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 74:

AGCATTTATT CAAGTAGGAG                                               20

(2) INFORMATION FOR SEQ ID NO: 75:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 75:

Tyr Leu Leu Ser Thr Ser Ser
      1               5

(2) INFORMATION FOR SEQ ID NO: 76:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 76:

TCTACTTTCC ACGTCCTCT                                                19

(2) INFORMATION FOR SEQ ID NO: 77:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 77:

```
    Gln Ile Gln Pro Gln Gln Arg
    1               5
```

(2) INFORMATION FOR SEQ ID NO: 78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 78:

```
    CAGATACAAC CGCAACAGC                                        19
```

(2) INFORMATION FOR SEQ ID NO: 79:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

```
    Pro Gln Gln Arg Ser Thr Gln Ser
    1               5
```

(2) INFORMATION FOR SEQ ID NO: 80:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 80:

```
    CCGCAACAGC GTTCAACTCA ATC                                   23
```

(2) INFORMATION FOR SEQ ID NO: 81:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

```
    Asp Gly Ala Ile Val Ala Trp
    1               5
```

(2) INFORMATION FOR SEQ ID NO: 82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 82:

```
    GACGGTGCGA TTGTTGCCTG G                                     21
```

(2) INFORMATION FOR SEQ ID NO: 83:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Glu Gly Asp Ser Gly Thr Val
       1            5

(2) INFORMATION FOR SEQ ID NO: 84:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 84:

GAAGGAGACT CAGGTACTG                                      19

(2) INFORMATION FOR SEQ ID NO: 85:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Thr Val Thr Asn Thr Ser
       1            5

(2) INFORMATION FOR SEQ ID NO: 86:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 86:

CCGTAACCAA TACAAGCAC                                      19

(2) INFORMATION FOR SEQ ID NO: 87:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Ser Ser Gln Leu Ala Tyr Asn Pro Ser
       1            5

(2) INFORMATION FOR SEQ ID NO: 88:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 88:

CTTCACAATT AGCGTATAAT CCTTC                                25

(2) INFORMATION FOR SEQ ID NO: 89:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 89:

Glu Gln His Lys Glu Val Ala
    1               5

(2) INFORMATION FOR SEQ ID NO: 90:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 90:

GAGCAGCATA AGGAAGTAG                                      19

(2) INFORMATION FOR SEQ ID NO: 91:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 91:

Phe Asn Gly Ile Gln Ile Val Pro
    1               5

(2) INFORMATION FOR SEQ ID NO: 92:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 92:

CATTCAATGG GATTCAAATT GTTCC                                25

(2) INFORMATION FOR SEQ ID NO: 93:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 93:

Val Gln Glu Ser Asn Gly Gly Gly
            1               5

(2) INFORMATION FOR SEQ ID NO: 94:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 94:

GTGCAGGAAT CTAATGGTGG AGG                                    23

(2) INFORMATION FOR SEQ ID NO: 95:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 95:

Glu Ile Gly Gly Lys Phe Thr Leu Asn
            1               5

(2) INFORMATION FOR SEQ ID NO: 96:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 96:

GATAGGAGGG AAATTTACAT TG                                     22

(2) INFORMATION FOR SEQ ID NO: 97:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 97:

CGAATTGAAT GCCGCTTTG                                         19

(2) INFORMATION FOR SEQ ID NO: 98:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

CTCAAAACTK TTTGCTGGCA CC                                          22

(2) INFORMATION FOR SEQ ID NO: 99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

GGATCRAGCA ACCTCTCTAG                                             20

(2) INFORMATION FOR SEQ ID NO: 100:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

ACTACTTACT TCTAGTAG                                               18

(2) INFORMATION FOR SEQ ID NO: 101:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 101:

Ser Asp Gln Gln Val Val Ile Glu
        1               5

(2) INFORMATION FOR SEQ ID NO: 102:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 102:

CCGAYCRACA KGTCRTRATT G                                           21

(2) INFORMATION FOR SEQ ID NO: 103:

(i) SEQUENCE CHARACTERISTICS:
        (A) LENGTH: 7 amino acids
        (B) TYPE: amino acid
        (C) STRANDEDNESS: single
```

```
        (D) TOPOLOGY: linear (ii) MOLECULE TYPE: peptide (xi) SEQUENCE DESCRIPTION: SEQ ID NO: 103:

Asn Gln Thr Ser Met Thr Glu
          1               5

(2) INFORMATION FOR SEQ ID NO: 104:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 104:

TCARDCTTCT ATGACAGMAC C                                         21

(2) INFORMATION FOR SEQ ID NO: 105:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

Gln Asp Gln Glu Lys Ile Ile Pro
          1               5

(2) INFORMATION FOR SEQ ID NO: 106:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 106:

CAAGATCAAG ARAARMTYAT YCCT                                      24

(2) INFORMATION FOR SEQ ID NO: 107:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

Ser His Lys Gln Asp Gln Glu
          1               5

(2) INFORMATION FOR SEQ ID NO: 108:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
    (ii) MOLECULE TYPE: DNA (genomic)

(xi) SEQUENCE DESCRIPTION: SEQ ID NO: 108:

CTCRTMAACA AGATCAAG                                              18

(2) INFORMATION FOR SEQ ID NO: 109:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

Ser Gly Ser Val Thr Ala His
        1               5

(2) INFORMATION FOR SEQ ID NO: 110:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 110:

CTGGAARYGT SACGGCTC                                              18

(2) INFORMATION FOR SEQ ID NO: 111:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 111:

GCTTAGTATC TACTTTAAAG AG                                         22

(2) INFORMATION FOR SEQ ID NO: 112:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 112:

GATACTATTT GATAAGTTCT CATC                                       24

(2) INFORMATION FOR SEQ ID NO: 113:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 113:

CTTTTGGCCT TTTTGCGAAA TAAC                                      24

(2) INFORMATION FOR SEQ ID NO: 114:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 114:

CTGGGTTTAA CGCTTTATCA GATTGATATT C                              31

(2) INFORMATION FOR SEQ ID NO: 115:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 115:

ACTTTTATTG CTAAACARGC TGC                                       23

(2) INFORMATION FOR SEQ ID NO: 116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 116:

TAACAGCTAC TCTTCCTTTG                                           20

(2) INFORMATION FOR SEQ ID NO: 117:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 117:

GGTGACATTT TCCAAGCTAA CATTG                                     25

(2) INFORMATION FOR SEQ ID NO: 118:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 118:

AGAGGACGTG GAAAGTAGA                                            19

(2) INFORMATION FOR SEQ ID NO: 119:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 119:

GCTGTTGCGG TTGTATCTG                                 19

(2) INFORMATION FOR SEQ ID NO: 120:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 120:

GATTGAGTTG AACGCTGTTG CGG                          23

(2) INFORMATION FOR SEQ ID NO: 121:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 121:

CCAGGCAACA ATCGCACCGT C                            21

(2) INFORMATION FOR SEQ ID NO: 122:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 122:

CAGTACCTGA GTCTCCTTC                                 19

(2) INFORMATION FOR SEQ ID NO: 123:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 123:

GTGCTTGTAT TGGTTACGG                                 19

(2) INFORMATION FOR SEQ ID NO: 124:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 124:

GAAGGATTAT ACGCTAATTG TGAAG                                       25

(2) INFORMATION FOR SEQ ID NO: 125:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 125:

GGAACAATTT GAATCCCATT GAATG                                       25

(2) INFORMATION FOR SEQ ID NO: 126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 126:

CCTCCACCAT TAGATTCCTG CAC                                         23

(2) INFORMATION FOR SEQ ID NO: 127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 127:

CAATGTAAAT TTCCCTCCTA TC                                          22

(2) INFORMATION FOR SEQ ID NO: 128:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 128:

GGTGCCAGCA AAMAGTTTTG AG                                          22

(2) INFORMATION FOR SEQ ID NO: 129:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO: 129:

CTAGAGAGGT TGCTYGATCC                                           20

(2) INFORMATION FOR SEQ ID NO: 130:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 130:

CTACTAGAAG TAAGTAGT                                             18

(2) INFORMATION FOR SEQ ID NO: 131:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 131:

GGTKCTGTCA TAGAAGHYTG A                                         21

(2) INFORMATION FOR SEQ ID NO: 132:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 132:

AGGRATRAKY TTYTCTTGAT CTTG                                      24

(2) INFORMATION FOR SEQ ID NO: 133:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 133:

CTTGATCTTG TTKAYGAG                                             18

(2) INFORMATION FOR SEQ ID NO: 134:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 134:
```

GAGCCGTSAC RYTTCCAG                                                        18

(2) INFORMATION FOR SEQ ID NO: 135:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 135:

CCAGTCCAAT GAACCTCTTA C                                                21

(2) INFORMATION FOR SEQ ID NO: 136:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 136:

AGGGAACAAA CCTTCCCAAC C                                                21

(2) INFORMATION FOR SEQ ID NO: 137:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 137:

CARMTAKTAA MTAGGGATAG                                                  20

(2) INFORMATION FOR SEQ ID NO: 138:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 138:

AGYTTCTATC GAAGCTGGGR ST                                               22

(2) INFORMATION FOR SEQ ID NO: 139:

(i) SEQUENCE CHARACTERISTICS:
        (A) LENGTH: 1035 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 139:

GGGTTAATTG GGTATTATTT TAAAGGGAAA GATTTTAATA ATCTGACTAT GTTTGCACCA60

ACCATAAATA ATACGCTTAT TTATGATCGG CAAACAGCAG ATACACTATT AAATAAGCA120

-continued

```
CAACAAGAGT TCAATTCTAT TCGATGGATT GGTTTAATAC AAAGTAAAGA AACAGGTGA    180

TTTACATTCC AATTATCAGA TGATAAAAAT GCCATCATTG AAATAGATGG AAAAGTTGT    240

TCTCGTAGAG GAGAAGATAA ACAAACTATC CATTTAGAAA AAGGAAAGAT GGTTCCAAT    300

AAAATTGAGT ACCAGTCCAA TGAACCTCTT ACTGTAGATA GTAAAGTATT TAACGATCT    360

AAACTATTTA AAATAGATGG TCATAATCAA TCGCATCAAA TACAGCAAGA TGATTTGAA    420

ATCCTGAATT TAATAAAAAG GAAACGAAAG AGCTTTTATC AAAACAGCA AAAAGAACC    480

TTTCTCTTCA AAACGGGGTT GAGAAGCGAT GAGGATGATG ATCTAGGATA CAGATGGTG    540

TAGCATTCCT GGATAATTGG GAAATGAATG GATATACCAT TCAAACGAAA AATGGCAGT    600

AAATGGGATG ATTCATTTGC AGAAAAAGGA TATACAAAAT TTGTTTCGAA TCCATATGA    660

GCCCATACAG CAGGAGATCC TTATACCGAT TATGAAAAG CAGCAAAAGA TATTCCTTT    720

TCGAACGCAA AAGAAGCCTT TAATCCTCTT GTAGCTGCTT TTCCATCTGT CAATGTAGG    780

TTAGAAAAAG TAGTAATTTC TAAAAATGAG GATATGAGTC AGGGTGTATC ATCCAGCAC    840

TCGAATAGTG CCTCTAATAC AAATTCAATT GGTGTTACCG TAGATGCTGG TTGGGAAGG    900

TTGTTCCCTA AATTTGGTAT TTCAACTAAT TATCAAAACA CATGGACCAC TGCACAAGA    960

TGGGGCTCTT CTAAAGAAGA TTCTACCCAT ATAAATGGAG CACAATCAGC CTTTTTAA    1020

GCAAATGTAC GATAT                                                   1035
```

(2) INFORMATION FOR SEQ ID NO: 140:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 140:

```
Gly Leu Ile Gly Tyr Tyr Phe Lys Gly Lys Asp Phe Asn Asn Leu Th
 1               5                  10                  15

Met Phe Ala Pro Thr Ile Asn Asn Thr Leu Ile Tyr Asp Arg Gln Th
            20                  25                  30

Ala Asp Thr Leu Leu Asn Lys Gln Gln Gln Glu Phe Asn Ser Ile Ar
        35                  40                  45

Trp Ile Gly Leu Ile Gln Ser Lys Glu Thr Gly Asp Phe Thr Phe Gl
    50                  55                  60

Leu Ser Asp Asp Lys Asn Ala Ile Ile Glu Ile Asp Gly Lys Val Va
65                  70                  75                  80

Ser Arg Arg Gly Glu Asp Lys Gln Thr Ile His Leu Glu Lys Gly Ly
                85                  90                  95

Met Val Pro Ile Lys Ile Glu Tyr Gln Ser Asn Glu Pro Leu Thr Va
            100                 105                 110

Asp Ser Lys Val Phe Asn Asp Leu Lys Leu Phe Lys Ile Asp Gly Hi
        115                 120                 125

Asn Gln Ser His Gln Ile Gln Gln Asp Asp Leu Lys Ile Leu Asn Le
    130                 135                 140

Ile Lys Arg Lys Arg Lys Ser Phe Tyr Gln Lys Gln Lys Glu Pr
145                 150                 155                 160

Phe Leu Phe Lys Thr Gly Leu Arg Ser Asp Glu Asp Asp Leu Gl
                165                 170                 175
```

```
            Tyr Arg Trp Xaa Xaa His Ser Trp Ile Ile Gly Lys Xaa Met Asp Il
                        180                 185                 190

Pro Phe Lys Arg Lys Met Ala Val Lys Trp Asp Asp Ser Phe Ala Gl
                    195                 200                 205

Lys Gly Tyr Thr Lys Phe Val Ser Asn Pro Tyr Glu Ala His Thr Al
                210                 215                 220

Gly Asp Pro Tyr Thr Asp Tyr Glu Lys Ala Ala Lys Asp Ile Pro Le
            225                 230                 235                 240

Ser Asn Ala Lys Glu Ala Phe Asn Pro Leu Val Ala Ala Phe Pro Se
                        245                 250                 255

Val Asn Val Gly Leu Glu Lys Val Val Ile Ser Lys Asn Glu Asp Me
                    260                 265                 270

Ser Gln Gly Val Ser Ser Ser Thr Ser Asn Ser Ala Ser Asn Thr As
                275                 280                 285

Ser Ile Gly Val Thr Val Asp Ala Gly Trp Glu Gly Leu Phe Pro Ly
            290                 295                 300

Phe Gly Ile Ser Thr Asn Tyr Gln Asn Thr Trp Thr Thr Ala Gln Gl
            305                 310                 315                 320

Trp Gly Ser Ser Lys Glu Asp Ser Thr His Ile Asn Gly Ala Gln Se
                        325                 330                 335

Ala Phe Leu Asn Ala Asn Val Arg Tyr
                        340                 345
```

(2) INFORMATION FOR SEQ ID NO: 141:

(i) SEQUENCE CHARACTERISTICS:
        (A) LENGTH: 1037 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 141:

```
GGGTTAATTG GGTATTATTT TAAAGGGAAA GATTTTAATA ATCTGACTAT GTTTGCACCA  60

ACCATAAATA ATACGCTTAT TTATGATCGG CAAACAGCAG ATACACTATT AAATAAGCA 120

CAACAAGAGT TCAATTCTAT TCGATGGATT GGTTTAATAC AAAGTAAAGA AACAGGTGA 180

TTTACATTCC AATTATCAGA TGATAAAAAT GCCATCATTG AAATAGATGG AAAAGTTGT 240

TCTCGTAGAG GAGAAGATAA ACAAACTATC CATTTAGAAA AAGGAAAGAT GGTTCCAAT 300

AAAATTGAGT ACCAGTCCAA TGAACCTCTT ACTGTAGATA GTAAAGTATT TAACGATCT 360

AAACTATTTA AAATAGATGG TCATAATCAA TCGCATCAAA TACAGCAAGA TGATTTGAA 420

AATCCTGAAT TTAATAAAAA AGAAACGAAA GAGCTTTTAT CAAAAACAGC AAAAAGRAA 480

CTTTTCTCTT CAAACGRRGT KGAGAAGCGA TGAGGATGAT RATCYTAGAT ACAGGTGGK 540

ATAGCATTCC YKGATAATTG GGGAAATGAA WGGRTATACC ATTCAACSGA AAAATGGSA 600

TCAAATGGGA TGATTCATTT GCGGAAAAAG GATATACAAA ATTTGTTTCG AATCCATAT 660

AAGCCCATAC AGCAGGAGAT CCTTATACCG ATTATGAAAA AGCAGCAAAA GATATTCCT 720

TATCGAACGC AAAAGAAGCC TTTAATCCTC TTGTAGCTGC TTTTCCATCT GTCAATGTA 780

GATTAGAAAA AGTAGTAATT TCTAAAAATG AGGATATGAG TCAGGGTGTA TCATCCAGC 840

CTTCGAATAG TGCCTCTAAT ACAAATTCAA TTGGTGTTAC CGTAGATGCT GGTTGGGAA 900

GTTTGTTCCC TAAATTTGGT ATTTCAACTA ATTATCAAAA CACATGGACC ACTGCACAA 960

AATGGGGCTC TTCTAAAGAA GATTCTACCC ATATAAATGG AGCACAATCA GCCTTTTTT1020
```

```
    ATGCAAATGT ACGATAT                                            1037

(2) INFORMATION FOR SEQ ID NO: 142:

(i) SEQUENCE CHARACTERISTICS:
        (A) LENGTH: 1048 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 142:

TGGGTTAATT GGGTATTATT TTAAAGGGCA AGAGTTTAAT CATCTTACTT TGTTCGCACC60

AACACGTGAT AATACCCTTA TTTATGATCA ACAAACAGCG AATTCCTTAT TAGATACCA120

GCAACAAGAA TATCAATCTA TTCGCTGGAT TGGTTTAATT CAAAGTAAAG AAACGGGTG180

TTTCACATTT AACTTATCAG ATGATCAACA TGCAATTATA GAAATCGATG GCAAAATCA240

TTCGCATAAA GGACAGAATA ACAAGTTGT TCACTTAGAA AAAGGAAAGT TAGTCCCGA300

AAAAATTGAG TATCAATCAG ATCAACTATT AAATAGGGAT AGTAACATCT TTAAAGAGT360

TAAATTATTC AAAGTAGATA GTCAGCAACA CGCTCACCAA GTTCAACTAG ACGAATTAA420

AAACCCTGCG TTTAATAAAA AGGAAACACA ACAATCTTAA GAAAAAGCAT CCAAAAACA480

TCTTTTTACA CCAGGGACAT TAAAAGGAAG ATACTGATGA TGATGATAAG GATAACAGG540

TGGGAGATTC TATTCCTGGA CCTTTTGGGG GAAGAAAATG GGTATACCAA TCCCAAAAT600

AAATAGCTGG TCCAAGTGGG ATGTTCATTC GCCGCGAAAG GGTATACAAA TTTGTTTCT660

AATCCACTTG ATAGTCATAC AGTTGGAGAT CCCTATACGG ATTATGAAAA AGCAGCAAG720

GATTTAGACT TGGCCCAATG CAAAGAAAC ATTTAACCCA TTAGTAGCTG CTTTTCCAA780

TGTGAATGTG AATTTGGAAA AAGTCATTTT ATCTAAAGAT GAAAATCTAT CCAATAGTG840

AGAGTCACAT TCCTCCACCA ACTGGTCTTA TACGAATACA GAAGGAGCTT CTATCGAAG900

TGGGGCTAAA CCAGAGGGTC CTACTTTTGG AGTGAGTGCT ACTTATCAAC ACTCTGAAA960

AGTTGCAAAA GAATGGGGAA CATCTACAGG AAATACCTCG CAATTTAATA CAGCTTCA1020

AGGATATTTA AATGCAAATG TACGATAT                                  1048

(2) INFORMATION FOR SEQ ID NO: 143:

(i) SEQUENCE CHARACTERISTICS:
        (A) LENGTH: 1175 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 143:

ACCTCTAGAT GCANGCTCGA GCGGCCGCCA GTGTGATGGA TATCTGCAGA ATTCGGATTA60

CTTGGGTATT ATTTTAAAGG GAAAGAGTTT AATCATCTTA CTTTGTTCGC ACCAACACG120

GATAATACCC TTATTTATGA TCAACAAACA GCGAATTCCT TATTAGATAC CAAACAACA180

GAATATCAAT CTATTCGCTG GATTGGTTTG ATTCAAAGTA AAGAAACAGG TGATTTCAC240

TTTAACTTAT CTGATGATCA AAATGCAATT ATAGAAATAG ATGGCAAAAT CATTTCGCA300

AAAGGACAGA ATAAACAAGT TGTTCACTTA GAAAAAGGAA AGTTAGTCCC GATAAAAAT360

GAGTATCAAT CAGATCAGAT ATTAACTAGG GATAGTAACA TCTTTAAAGA GTTCAATTA420
```

```
TCAAAGTAGA TAGTCAAGCA ACACTCTCAC CAAAGTTCAA CTTAGGNCNG AATTAAGNA    480

CCCTNGGATT TTAANTTNAA AAAAAGGAAC CCNCANCATT CTTTAGGAAA AAGCAGCAA    540

AACCAAATCC TTTTTTACCA CAGGATATTG AAAAGGAGAT ACGGGNTNGA TGATGGATT    600

ATACCGGGAT ACCAGTTGGG GNTTCTANTC CCTGACCTTT GGGGAAAGAA AATNGGTAT    660

CCNATCCCAA AANTTAAGCC AGCTGTCCAG GTGGGATGAT TCAATTCGCC CGCGAAAGG    720

TATACCAAAA TTTGTTTCTT AATCCACTTG AGAGTCATAC AGTTGGAGAT CCCTATACG    780

ATTATGAAAA AGCAGCAAGA GATTTAGACT TGGCCAATGC AAAAGAAACA TTTAACCCA    840

TAGTAGCTGC TTTTCCAAGT GTGAATGTGA ATTTGGAAAA AGTAATATTA TCCCCAGAT    900

AGAATTTATC TAACAGTGTA GAATCTCATT CGTCTACAAA TTGGTCTTAT ACGAATACT    960

AAGGAGCTTC TATCGAAGCT GGGGGTGGTC CATTAGGTAT TTCATTTGGA GTGAGTGC    1020

ATTATCAACA CTCTGAAACA GTTGCAAAAG AATGGGAAC ATCTACAGGA AATACCTC    1080

AATTTAATAC AGCTTCAGCA GGATATTTAA ATGCCAATGG TCGATNTAAG CCGAATNC    1140

NCACACTGNC GGCCGTTAGT AGTGGCACCG AGCCC                              1175
```

(2) INFORMATION FOR SEQ ID NO: 144:

(i) SEQUENCE CHARACTERISTICS:
        (A) LENGTH: 1030 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 144:

```
GGRTTAMTTG GGTATTATTT TAAAGGGAAA GATTTTAATG ATCTTACTGT ATTTGCACCA    60

ACGCGTGGGA ATACTCTTGT ATATGATCAA CAAACAGCAA ATACATTACT AAATCAAAA   120

CAACAAGACT TTCAGTCTAT TCGTTGGGTT GGTTTAATTC AAAGTAAAGA AGCAGGCGA   180

TTTACATTTA ACTTATCAGA TGATGAACAT ACGATGATAG AAATCGATGG GAAAGTTAT   240

TCTAATAAAG GGAAAGAAAA ACAAGTTGTC CATTTAGAAA AAGGACAGTT CGTTTCTAT   300

AAAATAGAAT ATCAAGCTGA TGAACCATTT AATGCGGATA GTCAAACCTT TAAAAATTT   360

AAACTCYTTA AAGTAGATAC TAAGCAACAG TCCCAGCAAA TTCAACTAGA TGAATTAAG   420

AACCCTGRAA TTTAATAAAA AAGAAACACA AGAATTTCTA ACAAAAGCAA CAAAAACAA   480

CCTTATTACT CAAAAAGTGA AGAGTACTAG GGATGAAGAC ACGGATACAG ATGGAGATT   540

TATTCCAGAC ATTTGGGAAG AAAATGGGTA TACCATCCAA AATAAGATTG CCGTCAAAT   600

GGATGATTCA TTAGCAAGTA AAGGATATAC GAAATTTGTT TCAAACCCAC TAGATACTC   660

CACGGTTGGA GATCCTTATA CAGATTATGA AAAAGCAGCA AGGGATTTAG ATTTGTCAA   720

TGCAAAAGAA ACATTTAACC CATTAGTTGC GGCTTTTCCA AGTGTGAATG TGAGTATGG   780

AAAAGTGATA TTGTCTCCAG ATGAGAACTT ATCAAATAGT ATCGAGTCTC ATTCATCTA   840

GAATTGGTCG TATACGAATA CAGAAGGGGC TTCTATTGAA GCTGGTGGGG GAGCATTAG   900

CCTATCTTTT GGTGTAAGTG CAAACTATCA ACATTCTGAA ACAGTTGGGT ATGAATGGG   960

AACATCTACG GGAAATACTT CGCAATTTAA TACAGCTTCA GCGGGGTATT TAAATGCC   1020

TRTAMGATAT                                                        1030
```